United States Patent [19]

Saikawa et al.

[11] 4,110,327
[45] Aug. 29, 1978

[54] 2,3 DIKETO-PIPERAZINO CARBONYLAMINO ALKANOIC ACIDS AND DERIVATIVES

[75] Inventors: Isamu Saikawa; Shuntaro Takano, both of Toyama; Chosaku Yoshida, Takaoka; Okuta Takashima, Toyama; Kaishu Momonoi, Shinminato; Seietsu Kuroda, Toyama; Miwako Komatsu, Toyama; Takashi Yasuda, Toyama; Yutaka Kodama, Toyama, all of Japan

[73] Assignee: Toyama Chemical Co., Ltd., Tokyo, Japan

[21] Appl. No.: 732,860

[22] Filed: Oct. 15, 1976

Related U.S. Application Data

[62] Division of Ser. No. 571,479, Apr. 24, 1975.

[30] Foreign Application Priority Data

| May 9, 1974 | [JP] | Japan | 49-50663 |
| May 13, 1974 | [JP] | Japan | 49-52254 |
| May 31, 1974 | [JP] | Japan | 49-60787 |
| Aug. 13, 1974 | [JP] | Japan | 49-91996 |
| Sep. 26, 1974 | [JP] | Japan | 49-109954 |
| Dec. 13, 1974 | [JP] | Japan | 49-142499 |
| Mar. 27, 1975 | [JP] | Japan | 50-37027 |

[51] Int. Cl.$^2$ .............. C07D 241/08; C07D 401/12; C07D 401/14; C07D 413/12
[52] U.S. Cl. .............. 544/385; 544/121; 544/22; 544/119; 544/28; 260/239.1; 544/357; 544/238; 544/295; 544/364; 544/360; 544/369; 544/370; 544/371; 544/363; 544/372; 544/379; 544/367; 544/283; 544/368; 544/384; 544/231
[58] Field of Search .............. 260/268 C, 247.2 A, 260/256.4 R; 544/121, 22

[56] References Cited

U.S. PATENT DOCUMENTS

| 3,433,784 | 3/1969 | Long et al. | 260/239.1 |
| 3,939,150 | 2/1976 | Murakami et al. | 260/239.1 |
| 3,959,258 | 5/1976 | Konig et al. | 260/239.1 |
| 3,983,105 | 9/1976 | Konig et al. | 260/239.1 |

*Primary Examiner*—Jose Tovar
*Attorney, Agent, or Firm*—Oblon, Fisher, Spivak, McClelland & Maier

[57] ABSTRACT

Novel penicillins and cephalosporins and non-toxic salts thereof, which contain a mono- or di-oxo- or thioxo-piperazino(thio)carbonylamino group in molecule. These compounds are valuable antibacterial compounds for use in mammals including man. This disclosure relates to such compounds and a process for the preparation thereof.

8 Claims, No Drawings

2,3 DIKETO-PIPERAZINO CARBONYLAMINO ALKANOIC ACIDS AND DERIVATIVES

This is a division, of application Ser. No. 571,479, filed Apr. 24, 1975.

This invention relates to novel penicillins and cephalosporins and to a process for producing the same.

The compounds of the present invention have various characteristics including a broad antibacterial spectrum against Gram-positive and Gram-negative bacteria, and effective antibacterial activity particularly against *Pseudomonas aeruginosa*, *Klebsiella pneumoniae* and *Proteus* species. Furthermore, the compounds of the present invention possess high resistance to β-lactamase produced from bacteria, and effective antibacterial activity even against clinical isolates of bacteria which are significant at present from the clinical standpoint. Accordingly, the compounds of the present invention are quite effective as therapeutic drugs for human and animal infectious diseases derived from the above-mentioned pathogenic microorganisms.

It has heretofore been known that 6-acylamino penicillanic acids and 7-acylaminocephalosporanic acids having an amino group at the α-position of the acyl group show strong antibacterial activity not only against Gram-positive bacteria but also against Gram-negative bacteria. However, there are the disadvantages that the known compounds described above show substantially no effective antibacterial activity against not only *Pseudomonas aeruginosa*, *Klebsiella pneumoniae* and *Proteus* species, which have been known as causes for clinically serious infectious diseases but also resistant bacteria which are frequently isolated at present from many clinical hospitals. And they tend to be hydrolyzed with β-lactamase produced from many drug-resistant bacteria.

With an aim to obtain penicillins and cephalosporins having no disadvantages mentioned above, the present inventors conducted extensive studies to find that novel compounds of formula (I) which appears hereinafter, which are prepared by bonding the moiety,

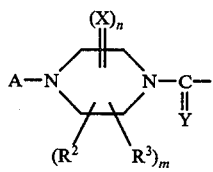

wherein A, X, Y, $R^2$, $R^3$, n and m are as mentioned hereinafter, to the amino group in the acyl group of penicillins and cephalosporins, can sufficiently satisfy the above-mentioned aim and have extremely valuable therapeutic effects.

It is an object of this invention to provide novel penicillins and cephalosporins containing a mono- or di-oxo- or thioxo-piperazino(thio)carbonylamino group in molecule.

It is another object of this invention to provide novel penicillins and cephalosporins having a broad antibacterial spectrum.

It is a further object of the invention to provide novel penicillins and cephalosporins having high resistance to β-lactamase produced from bacteria.

It is a still further object of the invention to provide novel penicillins and cephalosporins having effective antibacterial activity against clinical isolates of bacteria.

It is a still further object of the invention to provide a process for producing the novel penicillins and cephalosporins.

It is a still further object of the invention to provide a pharmaceutical composition containing the novel penicillins or cephalosporins as active ingredient.

Other objects and advantages of this invention will become apparent from the following description.

The compounds of the present invention are penicillins and cephalosporins represented by the general formula (I),

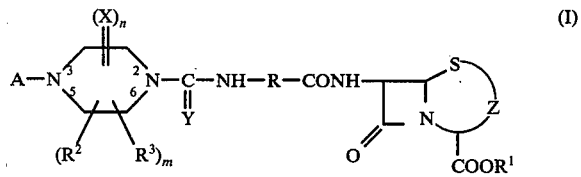

wherein R represents an amino acid residue; $R^1$ represents a hydrogen atom, a blocking group or a salt-forming cation; n represents 1 or 2; nX's, which may be the same or different, represent individually an oxygen or sulfur atom, and are linked in any combination at the 2-, 3- and 5-positions of the piperazine ring; m represents 4-n; each pair of $R^2$ and $R^3$ are linked to the same carbon atom, and m pairs of $R^2$ and $R^3$, which may be the same atom, or different, represent individually a hydrogen atom, a halogen atom, a carbonyl group, or a substituted or unsubstituted alkyl, cycloalkyl, aryl, acyl, aralkyl, alkoxycarbonylalkyl, acyloxyalkyl, alkoxy, alkoxycarbonyl, cycloalkyloxycarbonyl, aralkoxycarbonyl, aryloxycarbonyl, amino or carbamoyl group; any pair of $R^2$ and $R^3$ together with a common carbon atom may form a cycloalkyl ring; A represents a hydrogen atom, a hydroxy group, a nitro group, a cyano group, or an unsubstituted or substituted alkyl, alkenyl, alkynyl, alkadienyl, cycloalkyl, cycloalkenyl, cycloalkadienyl, aryl, acyl, aralkyl, acyloxyalkyl, alkoxy, cycloalkyloxy, aryloxy, alkoxycarbonyl, cycloalkyloxycarbonyl, aryloxycarbonyl, aralkoxycarbonyl, alkylsulfonyl, cycloalkylsulfonyl, arylsulfonyl, carbamoyl, thiocarbamoyl, acylcarbamoyl, acylthiocarbamoyl, alkylsulfonylcarbamoyl, arylsulfonylcarbamoyl, alkylsulfonylthiocarbamoyl, arylsulfonylthiocarbamoyl, sulfamoyl, alkoxycarbonylthioalkyl, alkoxythiocarbonylthioalkyl, amino or heterocyclic group; Y represents an oxygen or sulfur atom; and >Z represents

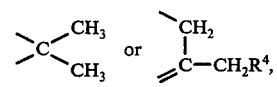

where $R^4$ represents a hydrogen atom, a halogen atom, a hydroxy group, a cyano group, an azido group, a quaternary ammonium group, or an organic group linked through O, N or S.

In the above-mentioned general formula (I), R represents an amino acid residue. Examples of such amino acid residue include residues of amino acids derived from various aliphatic, araliphatic, aromatic alicyclic and heterocyclic compounds, which amino acids may have the amino group at a position such as α-, β- or γ-position to the carboxyl group. Preferable as said R is an α-amino acid residue represented by the formula

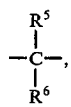

wherein $R^5$ is an alkyl group such as methyl, ethyl, propyl, butyl, pentyl, hexyl, heptyl, octyl or the like; a cycloalkyl group such as cyclopentyl, cyclohexyl, cycloheptyl or the like; a cycloalkenyl group such as cyclopentyl, cyclohexenyl, or the like; a cycloalkadienyl group such as cyclopentadienyl, cyclohexadienyl or the like; an aryl group such as phenyl, naphthyl or the like; an aralkyl group such as benzyl, phenetyl or the like; an aryloxy group such as phenoxy, naphthoxy or the like; an alkylthioalkyl group such as methylthiomethyl, ethylthiomethyl, methylthioethyl, ethylthioethyl or the like; or a heterocyclic group such as furyl, thienyl, oxazolyl, thiazolyl, isoxazolyl, isothiazolyl, imidazolyl, pyrazolyl, pyridyl, pyrazyl, pyrimidinyl, pyridazinyl, quinolyl, isoquinolyl, quinazolinyl, indolyl, indazolyl, 1,3,4-oxadiazolyl, 1,2,4-oxadiazolyl, 1,3,4-thiadiazolyl, 1,2,4-thiadiazolyl or the like; each group represented by said $R^5$ may be substituted by various groups, for example, halogen, hydroxy, nitro, alkyl, alkoxy, alkylthio, acyl, alkylsulfonylamino or the like; $R^6$ represents a hydrogen atom; and $R^5$ and $R^6$ together with a common carbon atom may form a cycloalkyl ring such as cyclohexyl, cycloheptyl or the like; a cycloalkenyl ring such as cyclopentenyl, cyclohexenyl, or the like; or a cycloalkadienyl ring such as cyclopentadienyl, cyclohexadienyl, or the like.

In the general formula (I), $R^1$ is a hydrogen atom, a blocking group or a salt-forming cation. The blocking group may be any of those which have heretofore been used in the field of penicillin or cephalosporin type compounds. Concretely, the blocking group includes (1) ester-forming groups capable of being removed by catalytic reduction, chemical reduction or hydrolysis under mild conditions e.g arylsulfonylalkyl groups such as toluene-sulfonylethyl, etc.; substituted or unsubstituted aralkyl groups such as benzyl, 4-nitrobenzyl, diphenylmethyl, trityl, 3,5-di(tert-butyl)-4-hydroxybenzyl, etc.; substituted or unsubstituted alkyl groups such as tert.-butyl, trichloroethyl, etc.; phenacyl group; alkoxyalkyl groups such as methoxymethyl, etc.; and unsubstituted or alkyl-substituted cyclic aminoalkyl groups such as piperidinoethyl, 4-methylpiperidinoethyl, morpholinoethyl, pyrrolidinoethyl, etc.; (2) ester-forming groups capable of being easily removed owing to enzymes in a living body, e.g. acyloxyalkyl groups such as pivaloyloxymethyl, etc.; phthalide group; and indanyl group; (3) silicon-containing groups, phosphorus-containing groups and tin-containing groups which are capable of being easily removed by treating with $H_2O$ or an alcohol, such as

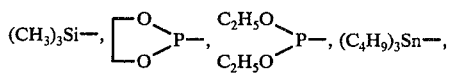

or the like. The examples of the blocking groups mentioned in above (1), (2) and (3) are merely typical, and other examples are disclosed in U.S. Pat. Nos. 3,499,909; 3,573,296 and 3,641,018 and DOS 2,301,014; 2,253,287 and 2,337,105 and may be used in this invention. The saltforming cation includes cations which have heretofore been known in the field of penicillin or cephalosporin type compounds, and preferable are those capable of forming non-toxic salts. The salts include alkali metal salts such as sodium salt, potassium salt, etc.; alkaline earth metal salts such as calcium salt, magnesium salt, etc.; ammonium salt; and salts with nitrogen-containing organic bases such as procaine, dibenzylamine, N-benzyl$\beta$-phenethylamine, 1-ephenamine, N,N-dibenzylethylenediamine, etc. In addition to the above cations, there may be used cations capable of forming the salts with other nitrogen-containing organic bases, such as trimethylamine, triethylamine, tributylamine, pyridine, dimethylaniline, N-methylpiperidine, N-methylmorpholine, diethylamine, dicyclohexylamine, etc. Furthermore, the cation includes quaternary ammonium groups formed at the 3-position of cephem ring, such as pyridinium, quinolinium, isoquinolinium, pyrimidinium, and the like. In this case, a betaine structure is formed in the molecule.

In the general formula (I), m pairs of $R^2$ and $R^3$, which may be the same or different, represent individually, a hydrogen atom; a halogen atom such as fluorine, chlorine, bromine, etc.; a carboxyl group; an alkyl group such as methyl, ethyl, propyl, butyl, pentyl, hexyl, heptyl, octyl, etc.; a cycloalkyl group such as cyclopentyl, cyclohexyl, cycloheptyl, etc.; an aryl group such as phenyl, naphthyl, etc.; an acyl group such as acetyl, propionyl, butyryl, benzoyl, etc.; an aralkyl group such as benzyl, phenethyl, etc.; an alkoxycarbonylalkyl group such as methoxycarbonylmethyl, ethoxycarbonylmethyl, etc.; an acyloxyalkyl group such as acetyloxymethyl, propionyloxymethyl, pivaloyloxymethyl, benzoyloxymethyl, etc.; an alkoxy group such as methoxy, ethoxy, propoxy, butoxy, etc.; an alkoxycarbonyl group such as methoxycarbonyl, ethoxycarbonyl, propoxycarbonyl, etc.; a cycloalkyloxycarbonyl group such as cyclopentyloxycarbonyl, cyclohexyloxycarbonyl, cycloheptyloxycarbonyl, etc.; an aralkoxycarbonyl group such as benzyloxycarbonyl, phenethoxycarbonyl, etc.; an aryloxycarbonyl group such as phenoxycarbonyl, naphthoxycarbonyl, etc.; an amino group such as amino, N-alkylamino (e.g. N-methylamino, N-ethylamino, N-propylamino, N-butylamino, etc.), N,N-dialkylamino (e.g. N,N-dimethylamino, N,N-diethylamino, N,N-dibutylamino, etc.), N-acylamino (e.g. N-acetylamino, N-propionylamino, N-butyrylamino, N-benzoylamino, etc.), and cyclic amino (e.g. pyrrolidino, piperidino, morpholino, etc.); and a carbamoyl group such as carbamoyl, N-methylaminocarbonyl, N-ethylaminocarbonyl, N,N-dimethylaminocarbonyl, N,N-diethylaminocarbonyl, etc. Further, $R^2$ and $R^3$ together with a common carbon atom may form a cycloalkyl ring such as a cyclopentyl, cyclohexyl or cycloheptyl group. Each of the groups mentioned above for said $R^2$ and $R^3$ may be substituted by various substituents, for example, halogen atoms, or alkyl, alkoxy, alkylthio, acyl or nitro groups.

In the general formula (I), A represents a hydrogen atom; a hydroxy group; a nitro group; a cyano group; an alkyl group such as methyl, ethyl, propyl, isopropyl, butyl, pentyl, hexyl, heptyl, octyl, dodecyl, or the like; an alkenyl group such as vinyl, propenyl, butenyl, or the like; an alkynyl group such as propargyl, or the like; an alkadienyl group such as 1,3-butadienyl, 1,3-pentadienyl, or the like; a cycloalkyl group such as cyclopentyl, cyclohexyl, cycloheptyl, or the like; a cycloalkenyl group such as cyclopentenyl, cyclohexenyl, or the like; a cycloalkadienyl group such as cyclopentadienyl, cyclohexadienyl, or the like; an aryl group such as phenyl, naphthyl, or the like; an acyl group such as formyl, acetyl, propionyl, isovaleryl, caproyl, enanthoyl, capryloyl, palmitoyl, stearoyl, acryloyl, cyclohexanecarbonyl, benzoyl, phenylglycyl, furoyl, thenoyl, or the like; an aralkyl group such as benzyl, phenethyl, or the like; an acyloxyalkyl group such as acetyloxyethyl, pivaloyloxymethyl, benzoyloxymethyl, or the like; an alkoxy group such as methoxy, ethoxy, propoxy, butoxy, or the like; a cycloalkyloxy group such as cyclopentyloxy, cyclohexyloxy, cycloheptyloxy, or the like; an aryloxy group such as phenoxy, naphthoxy, or the like; an alkoxycarbonyl group such as methoxycarbonyl, ethoxycarbonyl, propoxycarbonyl, butoxycarbonyl, or the like; a cycloalkyloxycarbonyl group such as cyclopentyloxycarbonyl, cyclohexyloxycarbonyl, cycloheptyloxycarbonyl, or the like; an aryloxycarbonyl group such as phenoxycarbonyl, (1- or 2-)naphthoxycarbonyl, or the like; an aralkoxycarbonyl group such as benzyloxycarbonyl, phenethoxycarbonyl, or the like; an alkylsulfonyl group such as methanesulfonyl, ethanesulfonyl, propanesulfonyl, butanesulfonyl, or the like; a cycloalkylsulfonyl group such as cyclopentanesulfonyl, cyclohexanesulfonyl, or the like; an arylsulfonyl group such as benzenesulfonyl, (1- or 2-)naphthalenesulfonyl, or the like; a carbamoyl group such as carbamoyl, N-alkylaminocarbonyl (e.g. N-methylaminocarbonyl, N-ethylaminocarbonyl, N-propylaminocarbonyl, N-butylaminocarbonyl, or the like), N-arylaminocarbonyl (e.g. N-phenylaminocarbonyl, or the like), N,N-dialkylaminocarbonyl (e.g. N,N-dimethylaminocarbonyl, N,N-diethylaminocarbonyl, or the like), cyclic amino carbonyl (e.g. pyrrolidinocarbonyl, piperidinocarbonyl, morpholinocarbonyl, or the like); a thiocarbamoyl group such as thiocarbamoyl, N-alkylaminothiocarbonyl (e.g. N-methylaminothiocarbonyl, N-ethylaminothiocarbonyl, N-propylaminothiocarbonyl, or the like), N-arylaminothiocarbonyl (e.g. N-phenylaminothiocarbonyl, or the like), N,N-dialkylaminothiocarbonyl (e.g. N,N-dimethylaminothiocarbonyl, N,N-diethylaminothiocarbonyl, or the like), or cyclic aminothiocarbonyl (e.g. pyrrolidinothiocarbonyl, piperidinothiocarbonyl, morpholinothiocarbonyl, or the like); an acylcarbamoyl group such as N-acetylcarbamoyl, N-propionylcarbamoyl, N-butyrylcarbamoyl, N-benzoylcarbamoyl, N-furoylcarbamoyl, N-thenoylcarbamoyl, or the like; an acylthiocarbamoyl group such as N-acetylthiocarbamoyl, N-propionylthiocarbamoyl, N-butyrylthiocarbamoyl, N-benzoylthiocarbamoyl, N-naphthoylthiocarbamoyl, N-furoylthiocarbamoyl, N-thenoylthiocarbamoyl, or the like); an alkylsulfonylcarbamoyl group such as methanesulfonylaminocarbonyl, ethanesulfonylaminocarbonyl, butanesulfonylaminocarbonyl, or the like; an arylsulfonylcarbamoyl group such as benzenesulfonylaminocarbonyl, (1- or 2-)naphthalenesulfonylaminocarbonyl, or the like; an alkylsulfonylthiocarbamoyl group such as methanesulfonylaminothiocarbonyl, ethanesulfonylaminothiocarbonyl, butanesulfonylaminothiocarbonyl, or the like; an arylsulfonylthiocarbamoyl group such as benzenesulfonylaminothiocarbonyl, naphthalenesulfonylaminothiocarbonyl, or the like; a sulfamoyl group such as sulfamoyl, N-methylsulfamoyl, N-ethylsulfamoyl, N-propylsulfamoyl, N-butylsulfamoyl, N,N-dimethylsulfamoyl, N,N-diethylsulfamoyl, N,N-dipropylsulfamoyl, N,N-dibutylsulfamoyl, N-phenylsulfamoyl, N-benzylsulfamoyl, N-cyclopentylsulfamoyl, N-cyclohexylsulfamoyl, or the like; an alkoxycarbonylthioalkyl group such as methoxycarbonylthiomethyl, ethoxycarbonylthiomethyl, propoxycarbonylthiomethyl, butoxycarbonylthiomethyl, methoxycarbonylthioethyl, or the like; an alkoxythiocarbonylthioalkyl group such as methoxythiocarbonylthiomethyl, ethoxythiocarbonylthiomethyl, propoxythiocarbonylthiomethyl, butoxythiocarbonylthiomethyl, methoxythiocarbonylthioethyl, or the like; an amino group such as amino, N-alkylamino (e.g. N-methylamino, N-ethylamino, N-propylamino, N-butylamino, or the like), N,N-dialkylamino (e.g. N,N-dimethylamino, n,N-diethylamino, n,N-dibutylamino, or the like), N-acylamino (e.g. N-acetylamino, N-propionylamino, N-butyrylamino, N-benzoylamino, or the like), or cyclic amino (e.g. pyrrolidino, piperidino, morpholino, or the like); or a heterocyclic group such as thiazolyl, pyridyl, pyridazyl, pyrazyl, thiadiazolyl, triazolyl, tetrazolyl, quinolyl, or the like. Each of the groups mentioned above for A in formula (I) may be substituted by any of such substituents as, for example, halogen atoms, hydroxyl groups, alkyl groups, alkoxy groups, alkylthio groups, nitro groups, cyano groups, amino groups (e.g. dialkylamino, cyclic amino, etc.), carboxyl groups, acyl groups, etc.

The quaternary ammonium groups for $R^4$ include pyridinium, quinolinium, isoquinolinium and pyrimidinium. Further, the organic group which is linked through O, N or S for $R^4$ includes alkoxy groups such as methoxy, ethoxy, propoxy, etc.; aryloxy groups such as phenoxy, naphthoxy, etc.; aralkoxy groups such as benzyloxy, phenethoxy, etc.; acyloxy groups such as acetyloxy, propionyloxy, butyryloxy, benzoyloxy, naphthoyloxy, cyclopentanecarbonyloxy, cyclohexanecarbonyloxy, furoyloxy, thenoyloxy, etc.; carbamoyloxy groups such as carbamoyloxy, N-methylaminocarbonyloxy, N,N-dimethylaminocarbonyloxy, N-acetylaminocarbonyloxy, phenylaminocarbonyloxy, benzylaminocarbonyloxy, cyclohexylaminocarbonyloxy, etc.; guanidino groups such as guanidino, N-methylguanidino, etc.; amino groups such as amino, N-alkylamino (e.g. N-methylamino, N-ethylamino, N-propylamino, N-butylamino, N-cyclohexylamino, N-phenylamino, etc.), N,N-dialkylamino (e.g. N,N-dimethylamino, N,N-diethylamino, N,N-dibutylamino, etc.), and cyclic amino (e.g. pyrrolidino, piperidino, morpholino, etc.); alkylthio groups such as methylthio, ethylthio, propylthio, etc.; arylthio groups such as phenylthio, (1- or 2-)-naphthylthio, etc.; aralkylthio groups such as benzylthio, phenethylthio, etc.; acylthio groups such as acetylthio, propionylthio, butyrylthio, benzoylthio, (1- or 2-)naphthoylthio, cyclopentanecarbonylthio, cyclohexanecarbonylthio, furoylthio, thenoylthio, isothiazolecarbonylthio, isoxazolecarbonylthio, thiadiazolecarbonylthio, triazolecarbonylthio, etc.; thiocarbamoylthio groups such as thiocarbamoylthio, N-methyl-thiocarbamoylthio, N,N-diethylthiocarbamoylthio, 1-piperidino-thiocarbonylthio, 1-morpholinothiocarbonylthio, 4-methyl-1-piperazinothiocarbonylthio, etc.; alkoxythiocarbonylthio groups such as methoxythiocarbonylthio, ethoxythiocarbonylthio, propoxythiocarbonylthio, butoxythiocarbonylthio, etc.; aryloxythiocarbonylthio groups such as phenoxythiocarbonylthio, etc.; cycloalkyloxythiocarbonylthio groups such as cyclohexyloxythiocarbonylthio, etc.; amidinothio groups such as amidinothio, N-methylamidinothio, N,N'-dimethylamidinothio, etc.; and heterocycle thio groups such as oxazolylthio, thiazolylthio, isoxazolylthio, isothiazolylthio, imidazolylthio, pyrazolylthio, pyridylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzothiazolylthio, triazolopyridylthio, purinylthio, pyridine-1-oxide-2-ylthio, pyridazine-1-oxide-6-ylthio, etc. Each of the groups mentioned above for $R^4$ may be substituted by any of such substituents as, for example, halogen atoms, alkyl groups, alkoxy groups, alkylthio groups, nitro groups, cyano groups, acylamino groups, acyl groups, carboxyl groups, carbamoyl groups, etc.

The above-mentioned compounds of formula (I) of the present invention have their optical isomers, and all of D-isomers, L-isomers and racemic compounds thereof are involved in the scope of the present invention.

In the present invention, preferable compounds of the general formula (I) are as follows:

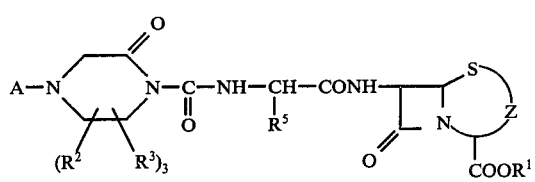
(Ia)

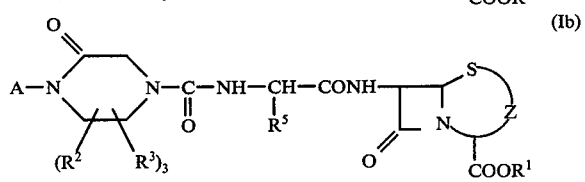
(Ib)

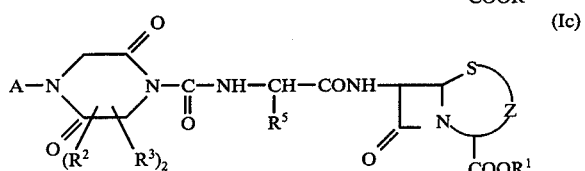
(Ic)

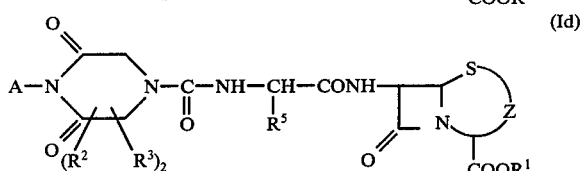
(Id)

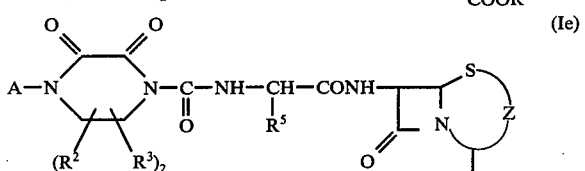
(Ie)

wherein $R^1$, $R^2$, $R^3$, A, $R^5$ and >Z are as defined above.

The compounds of formula (I) of the present invention are produced according to either the process (1), (2) or (3) described below.

PROCESS (1):

A process comprising reacting a compound represented by the general formula (II),

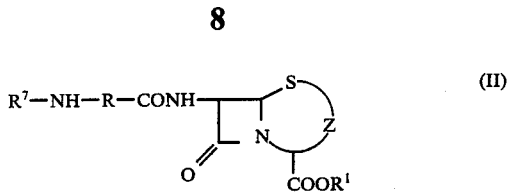
(II)

with a reactive derivative in the

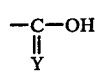

group (hereinafter referred to as "(thio)carboxyl group") of a compound represented by the general formula (III),

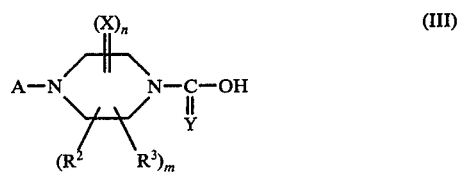
(III)

PROCESS (2):

A process comprising reacting a compound represented by the general formula (IV),

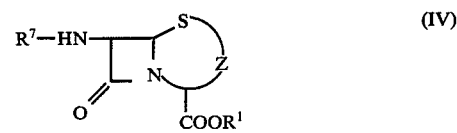
(IV)

with a compound represented by the general formula (V),

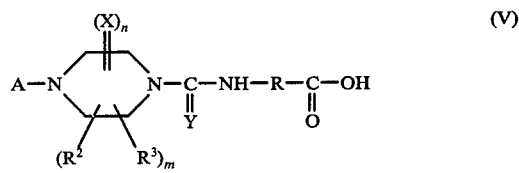
(V)

or with a reactive derivative in the

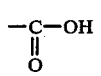

group (hereinafter referred to as "carboxyl group") of the compound of formula (V).

PROCESS (3)

A process comprising reacting a compound represented by the general formula (VI),

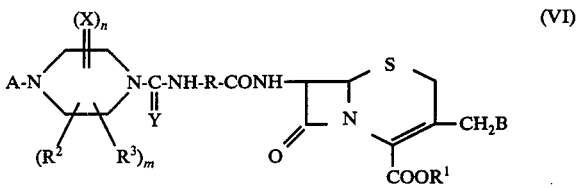
(VI)

with a compound represented by the general formula (VII), $$R^8M \quad (VII)$$

or with a tertiary amine.

In the above-mentioned formulas (II) to (VI), R, $R^1$, $R^2$, $R^3$, $R^4$, X, m, n, A, Y and >Z are as defined above; and $R^7$ represents a hydrogen atom, a silicon-containing group or a phosphorus-containing group, these silicon-containing and phosphorus-containing groups having the same meanings as mentioned above for $R^1$.

In the aforesaid formula (VI), B represents a substituent capable of being easily replaced by a nucleophilic reagent, and includes, for example, halogen atoms such as chlorine, bromine, etc.; lower alkanoyloxy groups such as formyloxy, acetoxy, propionyloxy, butyryloxy, pivaloyloxy, etc.; arylcarbonyloxy groups such as benzoyloxy, naphthoyloxy, etc.; arylcarbonylthio groups such as benzoylthio, naphthoylthio etc.; carbamoyloxy groups; heteroaromatic amine N-oxide thio groups having a thio group on the carbon atom adjacent to the N-oxide group in the molecule, such as pyridine-1-oxide-2-ylthio, pyridazine-1-oxide-6-ylthio, etc. Each of the groups mentioned above for B may be substituted by any of such substituents as, for example, halogen atoms, nitro groups alkyl groups, alkoxy groups, alkylthio groups, acyl groups, etc.

In formula (VII), $R^8$ represents a cyano group, an azido group or an organic group linked through O, N or S, and this organic group is the same as mentioned above for $R^4$.

In the formula (VII), M represents a hydrogen atom, an alkali metal or an alkaline earth metal. The tertiary amine used in the process (3) includes pyridine, quinoline, isoquinoline, pyrimidine, etc. These tertiary amines may be substituted by various substituents such as halogen, lower alkyl, carbamoyl and the like.

As the compound (II), there may be used any of D-isomer, L-isomer or racemic compound.

As the reactive derivative of the (thio)-carboxyl group of the compound of formula (III), there is used a reactive derivative of a carboxylic acid which is ordinarily employed for the synthesis of acid amide compounds. Examples of the reactive derivative are acid halides, acid azides, acid cyanides, mixed acid anhydrides, active esters, active amides, etc. Particularly preferable examples thereof are acid halides such as acid chlorides, acid bromides, etc., and active esters such as cyanomethyl ester, trichloromethyl ester, etc.

The reactive derivative of the (thio)carboxyl group of the compound of formula (III) can be easily obtained by reacting, for example, an oxopiperazine or thioxopiperazine of formula (VIII) synthesized according to the process of the literature references described below, with phosgene, thiophosgene, trichloromethyl ester of chloroformic acid, or the like,

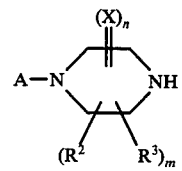

(VIII)

wherein A, X, $R^2$, $R^3$, m and n are as defined previously.
Literature references:
V. G. Granik, Khim-Farm. Zh., I(4), 16–19 (1967) (Russ);
Samuel R. Aspinall, J. An. Chem. Soc., 62, 1202–4 (1940);
Kuniyoshi MASUZAWA, Pharm. Bull. (Japan), 38 2078–2081 (1966);
Arthur P. Phillips, Ger. 1135472, Aug. 30 (1962);
J. L. Riebsomer, J. Org. Chem., 15 68–73 (1950);
Jongkees, Rec. trav. Chim., 27 305;
Patric T. Izzo, J. Am. Chem. Soc., 81 4668–4670 (1959); and
B. H. Chase & A. M. Downes, J. Chem. Soc., 3874–3877 (1953).

Concrete examples of the compound of formula (VIII) and the reactive derivative of (thio)carboxyl group of the compound of formula (III) are as set forth in Table 1 and Table 2, respectively, but it is needless to say that these are not limitative.

Table 1

| Compound | m.p. (recrystallization solvent | IR (cm$^{-1}$) |
|---|---|---|
| (piperazine-2-one, HN-NH with C=O) | 136° C (dioxane) | $\nu_{C=O}$ 1640 $\nu_{NH}$ 3450 – 3250 |
| (3-methyl-piperazine-2-one) | b.p. 143° C/1 mmHg oily material | $\nu_{C=O}$ 1650 $\nu_{NH}$ 3300 – 3200 |
| (5-methyl-piperazine-2-one) | b.p. 122 – 125° C/2 mmHg 140 – 141° C (IPA) | $\nu_{C=O}$ 1650 – 1630 $\nu_{NH}$ 3260, 3170 |

Table 1-continued

Structure (VIII):
- Piperazine ring with AN— on left, —NH on right, (X)$_n$ on top, (R$^2$ R$^3$)$_m$ on bottom

| Compound | m.p. (recrystallization solvent) | IR (cm$^{-1}$) |
|---|---|---|
| 3,6-dimethyl-2,5-dioxopiperazine (O, CH$_3$ / HN, NH / CH$_3$, O) | 85–86° C (IPA – IPE) | $\nu_{C=O}$ 1660–1620 |
| 3-(ethoxycarbonylmethyl)-2-oxopiperazine with CH$_2$CO$_2$C$_2$H$_5$ | 105–106° C (AcOEt) | $\nu_{C=O}$ 1710, 1640; $\nu_{NH}$ 3300, 3190 |
| CH$_3$CON–piperazinone | 112–113° C (benzene) | $\nu_{C=O}$ 1645, 1625; $\nu_{NH}$ 3380, 3220 |
| ClCH$_2$CON–piperazinone | 129–130° C (IPA) | $\nu_{C=O}$ 1650, 1630; $\nu_{NH}$ 3270 |
| Cl$_2$CHCON–piperazinone | 134–135° C (IPA) | $\nu_{C=O}$ 1660–1630; $\nu_{NH}$ 3280 |
| CH$_3$(CH$_2$)$_{13}$CH$_2$CON–piperazinone | 96–97° C (CCl$_4$) | $\nu_{C=O}$ 1670, 1640; $\nu_{NH}$ 3200 |
| CH$_3$(CH$_2$)$_5$CH$_2$CON–piperazinone | 80–81° C (IPE) | $\nu_{C=O}$ 1660, 1620; $\nu_{NH}$ 3250 |
| CH$_3$(CH$_2$)$_4$CH$_2$CON–piperazinone | 83–84° C (IPE) | $\nu_{C=O}$ 1660, 1620; $\nu_{NH}$ 3250 |
| CH$_3$(CH$_2$)$_3$CH$_2$CON–piperazinone | 99–100° C (CCl$_4$) | $\nu_{C=O}$ 1660, 1620; $\nu_{NH}$ 3250 |
| Cyclohexyl-CON–piperazinone | 203–205° C (IPA) | $\nu_{C=O}$ 1670, 1620; $\nu_{NH}$ 3250 |
| Phenyl-CON–piperazinone | 91–93° C (IPA) | $\nu_{C=O}$ 1640, 1600; $\nu_{NH}$ 3250 |
| 4-Cl-phenyl-CON–piperazinone | 146–148° C (IPA) | $\nu_{C=O}$ 1650, 1620; $\nu_{NH}$ 3200 |
| 4-CH$_3$-phenyl-CON–piperazinone | 118–120° C (IPA) | $\nu_{C=O}$ 1660, 1620; $\nu_{NH}$ 3200 |

Table 1-continued (VIII)

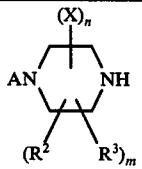

| Compound | m.p. (recrystallization solvent) | IR (cm$^{-1}$) |
|---|---|---|
| 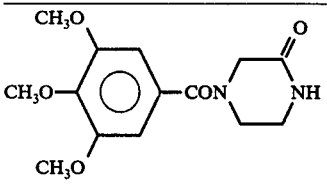 | 182 – 185° C (IPA) | $\nu_{C=O}$ 1670, 1600<br>$\nu_{NH}$ 3200 |
| 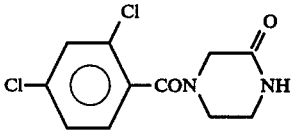 | Oily material | $\nu_{C=O}$ 1650, 1620<br>$\nu_{NH}$ 3200 |
| 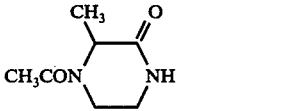 | 124 – 126° C (⌬) | $\nu_{C=O}$ 1650, 1630<br>$\nu_{NH}$ 3225 |
| 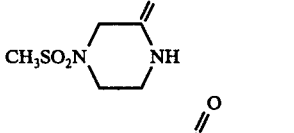 | 167 – 168° C (EtOH) | $\nu_{C=O}$ 1680<br>$\nu_{NH}$ 3200<br>$\nu_{SO_2N}$ <1310, 1140 |
| 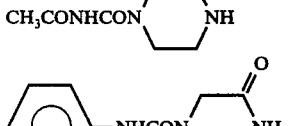 | 176 – 179° C (⌬) | $\nu_{C=O}$ 1680, 1650, 1620<br>$\nu_{NH}$ 3300 |
| 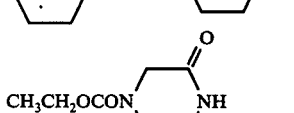 | 85 – 88° C (AcOEt) | $\nu_{C=O}$ 1660, 1640<br>$\nu_{NH}$ 3300, 3200 |
| 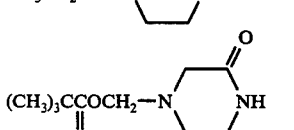 | 81 – 82° C (dioxane) | $\nu_{C=O}$ 1690 – 1650<br>$\nu_{NH}$ 3200, 3050 |
| 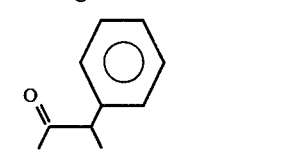 | 189 – 190° C (IPA) | $\nu_{C=O}$ 1650, 1620<br>$\nu_{NH}$ 3250 |
| 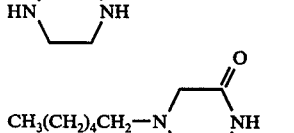 | 136 – 138° C (Acetone) | $\nu_{C=O}$ 1660<br>$\nu_{NH}$ 3200 |
| 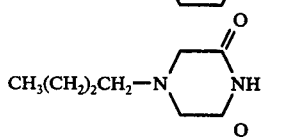 | Oily material | $\nu_{C=O}$ 1650 – 1630<br>$\nu_{NH}$ 3270 |
| 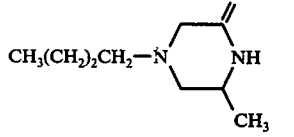 | Oily material | $\nu_{NH}$ 3250<br>$\nu_{C=O}$ 1650 – 1630 |
|  | Oily material | $\nu_{C=O}$ 1650 – 1620 |

Table 1-continued (VIII)

Structure (VIII): piperazine-type ring with (X)$_n$ substituent, AN— and —NH on nitrogens, (R$^2$) and (R$^3$)$_m$ on carbons.

| Compound | m.p. (recrystallization solvent) | IR (cm$^{-1}$) |
|---|---|---|
| CH$_3$(CH$_2$)$_6$CH$_2$—N(C=O)—piperazinone-NH | Oily material | $\nu_{NH}$ 3270<br>$\nu_{C=O}$ 1650 – 1630<br>Hydrochloride<br>$\nu_{C=O}$ 1680<br>$\nu_{NH}$ 3200, 3080 |
| CH$_3$CON—piperazinone with CH$_3$ substituent, NH | Oily material | $\nu_{C=O}$ 1680<br>$\nu_{NH}$ 3300 |
| Ph—NHCON—piperazinone-NH | Oily material | $\nu_{C=O}$ 1720, 1640<br>$\nu_{NH}$ 3300 |
| CH$_3$N—piperazinone-NH | b.p. 104° C/4 mmHg | $\nu_{C=O}$ 1620<br>$\nu_{NH}$ 3275 |
| CH$_3$CH$_2$—N—piperazinone-NH | Oily material | $\nu_{C=O}$ 1610<br>$\nu_{NH}$ 3250 |
| CH$_3$(CH$_2$)$_2$CH$_2$—N—piperazinone-NH | Oily material | $\nu_{C=O}$ 1610<br>$\nu_{NH}$ 3250 |
| (CH$_3$)$_2$CH—N—piperazinone-NH | Oily material | $\nu_{C=O}$ 1610<br>$\nu_{NH}$ 3400 – 3200 |
| CH$_3$(CH$_2$)$_3$CH$_2$—N—piperazinone-NH | Oily material | $\nu_{C=O}$ 1620<br>$\nu_{NH}$ 3270 |
| (CH$_3$)$_2$CHCH$_2$CH$_2$—N—piperazinone-NH | Oily material | $\nu_{C=O}$ 1620<br>$\nu_{NH}$ 3270 |
| CH$_3$(CH$_2$)$_4$CH$_2$—N—piperazinone-NH | Oily material | $\nu_{C=O}$ 1620<br>$\nu_{NH}$ 3270 |
| CH$_3$(CH$_2$)$_5$CH$_2$—N—piperazinone-NH | Oily material | $\nu_{C=O}$ 1620<br>$\nu_{NH}$ 3270 |
| CH$_3$(CH$_2$)$_6$CH$_2$—N—piperazinone-NH | Oily material | $\nu_{C=O}$ 1620<br>$\nu_{NH}$ 3270 |
| CH$_3$(CH$_2$)$_{10}$CH$_2$—N—piperazinone-NH | Oily material | $\nu_{C=O}$ 1620<br>$\nu_{NH}$ 3270 |
| cyclopropyl-N—piperazinone-NH | Oily material | $\nu_{C=O}$ 1620<br>$\nu_{NH}$ 3300 |

Table 1-continued $$\text{(VIII)}$$

Structure: piperazine-type ring with AN—, NH, $(X)_n$, $(R^2\ R^3)_m$

| Compound | m.p. (recrystallization solvent) | IR (cm$^{-1}$) |
|---|---|---|
| $CH_3(CH_2)_2CH_2$—N(C=O)(CH-CH₃)—CH₂—NH (3-methyl piperazinone, butyl) | Oily material | $\nu_{C=O}$ 1630, $\nu_{NH}$ 3300 |
| $CH_3(CH_2)_2CH_2$—N(C=O)—CH₂—NH—CH(CH₃) (6-methyl, butyl) | Oily material | $\nu_{C=O}$ 1630, $\nu_{NH}$ 3300 |
| $CH_3(CH_2)_2CH_2$—N(C=O)—CH₂—NH—CH₂—CH(CH₃) (5-methyl, butyl) | Oily material | $\nu_{C=O}$ 1630, $\nu_{NH}$ 3200 |
| C$_6$H$_5$—CH$_2$—N(C=O)—CH₂—NH (benzyl) | 157–158° C (dioxane) | $\nu_{C=O}$ 1630, $\nu_{NH}$ 3300 |
| H$_2$NCO—N(C=O)(CH-CH₃)—CH₂—NH | Oily material | $\nu_{C=O}$ 1700, $\nu_{NH}$ 3400–3250 |
| HOCH$_2$CH$_2$—N(C=O)—CH₂—NH | b.p. 183–185° C/2 mmHg | $\nu_{C=O}$ 1620 |
| CH$_2$=CHCH$_2$—N(C=O)—CH₂—NH | Oily material | $\nu_{C=O}$ 1650, $\nu_{NH}$ 3300 |
| CH$_2$=CHCH(CH$_3$)—N(C=O)—CH₂—NH | Oily material | $\nu_{C=O}$ 1620, $\nu_{NH}$ 3300 |
| CH$_2$=C(CH$_3$)CH$_2$—N(C=O)—CH₂—NH | Oily material | $\nu_{C=O}$ 1640, $\nu_{NH}$ 3300 |
| CH(CH$_3$)=CHCH$_2$—N(C=O)—CH₂—NH | Oily material | $\nu_{C=O}$ 1660, $\nu_{NH}$ 3350 |
| Morpholino-NCH$_2$—N(C=O)—CH₂—NH | Oily material | $\nu_{C=O}$ 1630, $\nu_{NH}$ 3300 |
| CH$_3$CO—N(C=O)—CH₂—NH—C=O (2,5-dioxo, acetyl) | 184–185° C (EtOH) | $\nu_{C=O}$ 1690–1650, $\nu_{NH}$ 3190, 3050 |

Table 1-continued (VIII)

structure: piperazine ring with AN substituent, (X)$_n$, NH, (R$^2$), (R$^3$)$_m$

| Compound | m.p. (recrystallization solvent) | IR (cm$^{-1}$) |
|---|---|---|
| C$_6$H$_5$-CON- piperazine-2,5-dione | 177 – 178° C (EtOH) | $\nu_{C=O}$ 1680 – 1650<br>$\nu_{NH}$ 3190, 3050 |
| CH$_3$-N- piperazine-2,3,5-trione derivative | 142 – 143° C (IPA) | $\nu_{C=O}$ 1680 – 1620<br>$\nu_{NH}$ 3200 |
| C$_6$H$_5$-CH$_2$-N- piperazine-2,5-dione | 209° C (IPA) | $\nu_{C=O}$ 1660 – 1630<br>$\nu_{NH}$ 3230 |
| CH$_3$-N- piperazine-2,3-dione | 158°C (IPA) | $\nu_{C=O}$ 1695, 1660<br>$\nu_{NH}$ 3220 |
| CH$_3$COOCH$_2$CH$_2$-N- piperazine-2,3-dione | Oily material | $\nu_{C=O}$ 1730 – 1650<br>$\nu_{NH}$ 3300 – 3200 |
| CH$_3$CH$_2$-N- piperazine-2,3-dione | 124° C (dioxane) | $\nu_{C=O}$ 1680, 1650<br>$\nu_{NH}$ 3250 |
| CH$_3$CH$_2$CH$_2$-N- piperazine-2,3-dione | 98 – 100° C (dioxane) | $\nu_{C=O}$ 1680, 1650<br>$\nu_{NH}$ 3200, 3100 |
| CH$_3$(CH$_2$)$_2$CH$_2$-N- piperazine-2,3-dione | 111 – 113° C (CCl$_4$) | $\nu_{C=O}$ 1695, 1670<br>$\nu_{NH}$ 3240, 3150 |
| (CH$_3$)$_2$CH-N- piperazine-2,3-dione | 166 – 167° C (dioxane) | $\nu_{C=O}$ 1650<br>$\nu_{NH}$ 3300 – 3200 |
| CH$_3$(CH$_2$)$_3$CH$_2$-N- piperazine-2,3-dione | 104 – 106° C (IPE) | $\nu_{C=O}$ 1700, 1660<br>$\nu_{NH}$ 3200, 3100 |
| CH$_3$(CH$_2$)$_4$CH$_2$-N- piperazine-2,3-dione | 111 – 115° C (IPE) | $\nu_{C=O}$ 1700, 1660<br>$\nu_{NH}$ 3200, 3100 |
| CH$_3$(CH$_2$)$_5$CH$_2$-N- piperazine-2,3-dione | 112 – 115° C (IPE) | $\nu_{C=O}$ 1700, 1660<br>$\nu_{NH}$ 3200, 3100 |
| CH$_3$(CH$_2$)$_6$CH$_2$-N- piperazine-2,3-dione | 116 – 120° C (IPE) | $\nu_{C=O}$ 1700, 1660<br>$\nu_{NH}$ 3225, 3100 |

Table 1-continued
(VIII)
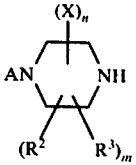
| Compound | m.p. (recrystallization solvent) | IR (cm$^{-1}$) |
|---|---|---|
| 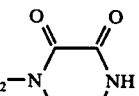 | 136 – 137° C (Acetone) | $\nu_{C=O}$ 1680, 1655<br>$\nu_{NH}$ 3200, 3100 |
| 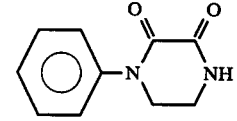 | 202 – 204° C (IPA) | $\nu_{C=O}$ 1690, 1645<br>$\nu_{NH}$ 3260 |
|  | 128 – 129° C (EtOH) | $\nu_{C=O}$ 1700 – 1650<br>$\nu_{NH}$ 3200 – 3100 |
| 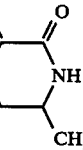 | 127 – 128° C (AcOEt) | $\nu_{C=O}$ 1660<br>$\nu_{NH}$ 3200, 3080 |
| 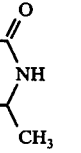 | 146 – 147° C (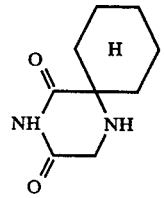) | $\nu_{C=O}$ 1660<br>$\nu_{NH}$ 3200, 3100 |
| 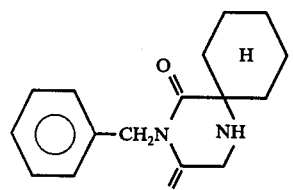 | 183 – 185° C (EtOH) | $\nu_{C=O}$ 1720, 1660<br>$\nu_{NH}$ 3320, 3175, 3050 |
| 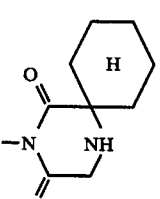 | 96 – 99° C (IPA-n-Hexane) | $\nu_{C=O}$ 1720, 1660<br>$\nu_{NH}$ 3330 |
| 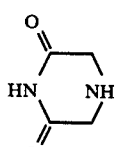 | 143 – 146° C (IPA) | $\nu_{C=O}$ 1765, 1720 1680<br>$\nu_{NH}$ 3350 |
| | 210 – 212° C (MeOH) | $\nu_{C=O}$ 1680<br>$\nu_{NH}$ 3380, 3290, 3070 |

Table 1-continued
(VIII)
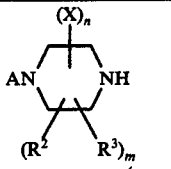
| Compound | m.p. (recrystallization solvent) | IR (cm$^{-1}$) |
|---|---|---|
| 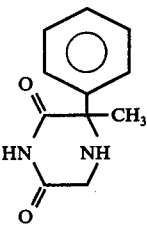 | 132 – 133°C (EtOH) | $\nu_{C=O}$ 1715, 1685<br>$\nu_{NH}$ 3275, 3170 |
| 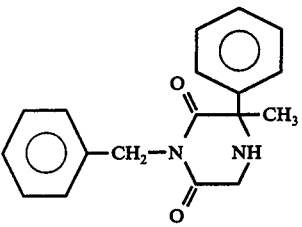 | 98 – 100° C (IPA) | $\nu_{C=O}$ 1715, 1665<br>$\nu_{NH}$ 3360 |
Note:
IPA = (CH$_3$)$_2$CHOH
IPE = (CH$_3$)$_2$CHOCH(CH$_3$)$_2$
AcOEt = CH$_3$COOCH$_2$CH$_3$
EtOH = CH$_3$CH$_2$OH
Table 2
Reactive derivatives of (III)
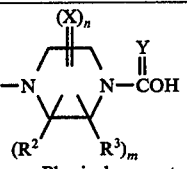
| Compound | Physical property | I.R. (cm$^{-1}$) |
|---|---|---|
| 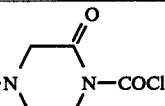 | Oily material | $\nu_{C=O}$ 1790, 1710, 1640 |
| 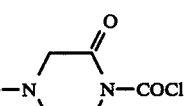 | " | $\nu_{C=O}$ 1790, 1730 – 1650 |
| 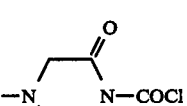 | " | $\nu_{C=O}$ 1790, 1730 – 1650 |
| 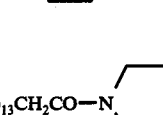 | " | $\nu_{C=O}$ 1740, 1660, 1640 |
| 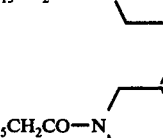 | " | $\nu_{C=O}$ 1740, 1680 – 1640 |

Table 2-continued

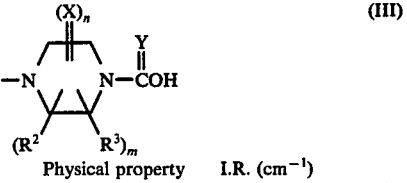

| Compound | Physical property | I.R. (cm$^{-1}$) |
|---|---|---|
| CH$_3$(CH$_2$)$_4$CH$_2$CO–N⌐N–COCl (3-oxo) | " | $\nu_{C=O}$ 1740, 1680–1640 |
| CH$_3$(CH$_2$)$_3$CH$_2$CO–N⌐N–COCl (3-oxo) | " | $\nu_{C=O}$ 1790, 1710, 1640 |
| Cyclohexyl-CO–N⌐N–COCl (3-oxo) | " | $\nu_{C=O}$ 1790, 1730, 1640 |
| C$_6$H$_5$-CO–N⌐N–COCl (3-oxo) | " | $\nu_{C=O}$ 1740, 1660, 1630 |
| 4-Cl-C$_6$H$_4$-CO–N⌐N–COCl (3-oxo) | " | $\nu_{C=O}$ 1740, 1640 |
| 4-CH$_3$-C$_6$H$_4$-CO–N⌐N–COCl (3-oxo) | " | $\nu_{C=O}$ 1730, 1650 |
| 3,4,5-(CH$_3$O)$_3$-C$_6$H$_2$-CO–N⌐N–COCl (3-oxo) | " | $\nu_{C=O}$ 1740, 1640 |
| 2,4-Cl$_2$-C$_6$H$_3$-CO–N⌐N–COCl (3-oxo) | " | $\nu_{C=O}$ 1720, 1640 |
| CH$_3$CO–N⌐N–COCl (3-oxo, 3-CH$_3$) | " | $\nu_{C=O}$ 1790, 1710, 1640 |
| CH$_3$SO$_2$–N⌐N–COCl (3-oxo) | " | $\nu_{C=O}$ 1790, 1700 $\nu_{SO2}$ 1320, 1140 |
| CH$_3$CONHCO–N⌐N–COCl (3-oxo) | " | $\nu_{C=O}$ 1790, 1720–1660 |

Table 2-continued

| Compound | Physical property | I.R. (cm$^{-1}$) |
|---|---|---|
| ⟨phenyl⟩-NHCO-N(piperazinone)-COCl | " | $\nu_{C=O}$ 1740, 1720, 1650 |
| CH$_3$CH$_2$OCO-N(piperazinone)-COCl | " | $\nu_{C=O}$ 1750, 1720, 1640 |
| (CH$_3$)$_3$CCOOCH$_2$-N(piperazinone)-COCl | " | $\nu_{C=O}$ 1740 – 1720, 1670 |
| CH$_3$(CH$_2$)$_4$CH$_2$-N(piperazinone)-COCl | " | $\nu_{C=O}$ 1790, 1720 |
| CH$_3$(CH$_2$)$_2$CH$_2$-N(piperazinone)-COCl | " | $\nu_{C=O}$ 1790, 1720 |
| CH$_3$(CH$_2$)$_2$CH$_2$-N(piperazinone with CH$_3$)-COCl | " | $\nu_{C=O}$ 1790, 1720 |
| CH$_3$(CH$_2$)$_6$CH$_2$-N(piperazinone)-COCl | " | $\nu_{C=O}$ 1790, 1720 |
| HN(piperazinone)-COCl | m.p. 115 – 116° C (decomp.) (from benzene) | $\nu_{C=O}$ 1720, 1660 |
| HN(piperazinone with 2 CH$_3$)-COCl | Crystal | $\nu_{C=O}$ 1730, 1670 |
| HN(piperazinone with CH$_3$)-COCl | " | $\nu_{C=O}$ 1720, 1660 |
| HN(piperazinone with CH$_2$COOCH$_2$CH$_3$)-COCl | m.p. 59 – 60° C (from IPE) | $\nu_{C=O}$ 1710 – 1730, 1660 |

Table 2-continued
Reactive derivatives of formula (III):
$$A-N\underset{(R^2\ R^3)_m}{\overset{(X)_n}{\diagup\!\!\!\diagdown}}N-\underset{Y}{\overset{\|}{C}}OH$$
| Compound | Physical property | I.R. (cm$^{-1}$) |
|---|---|---|
| 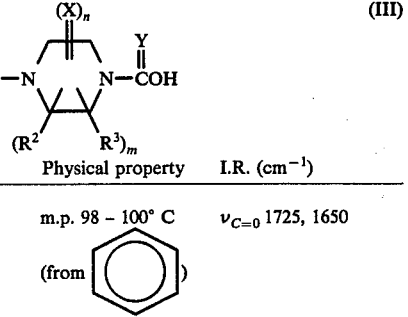 | m.p. 98 – 100° C (from 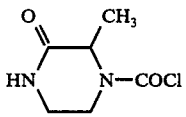) | $\nu_{C=0}$ 1725, 1650 |
| 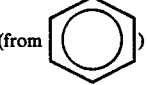 | Oily material | $\nu_{C=0}$ 1720, 1690 |
| 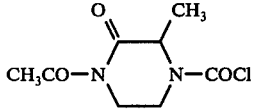 | " | $\nu_{C=0}$ 1790, 1740 – 1700 |
| 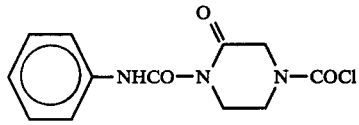 | " | $\nu_{C=0}$ 1710, 1630 |
| 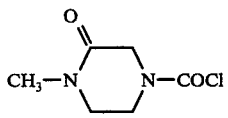 | " | $\nu_{C=0}$ 1730, 1650 |
| 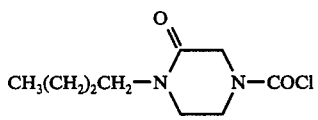 | " | $\nu_{C=0}$ 1730, 1650 |
| 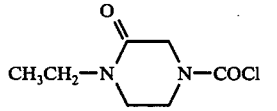 | " | $\nu_{C=0}$ 1720, 1640 |
| 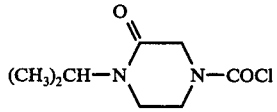 | " | $\nu_{C=0}$ 1730, 1640 |
| 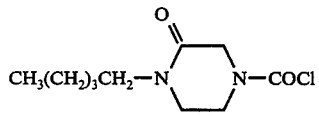 | " | $\nu_{C=0}$ 1720, 1640 |
| 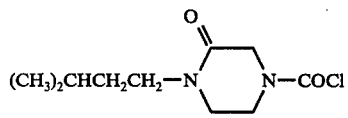 | " | $\nu_{C=0}$ 1730, 1640 |
| 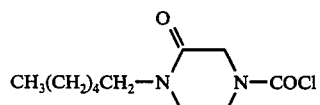 | " | $\nu_{C=0}$ 1730, 1640 |
| 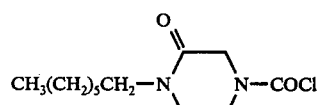 | " | $\nu_{C=0}$ 1720, 1640 |

Table 2-continued $$\text{Reactive derivatives of } A-N\underset{(R^2\ \ R^3)_m}{\overset{(X)_n}{\underset{\displaystyle \diagup \diagdown}{\phantom{XX}}}}N-\overset{Y}{\underset{\displaystyle \|}{C}}OH \qquad (III)$$

| Compound | Physical property | I.R. (cm$^{-1}$) |
|---|---|---|
| CH$_3$(CH$_2$)$_{10}$CH$_2$–N⟨piperazinone⟩N–COCl | " | $\nu_{C=O}$ 1720, 1640 |
| (cyclopentyl-H)–N⟨piperazinone⟩N–COCl | " | $\nu_{C=O}$ 1730, 1640 |
| CH$_3$(CH$_2$)$_2$CH$_2$–N⟨piperazinone, CH$_3$⟩N–COCl | " | $\nu_{C=O}$ 1730, 1640 |
| CH$_3$(CH$_2$)$_2$CH$_2$–N⟨piperazinone, CH$_3$⟩N–COCl | " | $\nu_{C=O}$ 1720, 1640 |
| CH$_3$(CH$_2$)$_2$CH$_2$–N⟨piperazinone⟩N–COCl with CH$_3$ | " | $\nu_{C=O}$ 1730, 1650 |
| HN⟨phenyl-piperazinone⟩N–COCl | m.p. 105 – 107° C | $\nu_{C=O}$ 1730, 1650 |
| C$_6$H$_5$–CH$_2$–N⟨piperazinone⟩N–COCl | Oily material | $\nu_{C=O}$ 1720, 1645 |
| H$_2$NCO–N⟨piperazinone, CH$_3$⟩N–COCl | " | $\nu_{C=O}$ 1700 – 1740 |
| HOCH$_2$CH$_2$–N⟨piperazinone⟩N–COCl | " | $\nu_{C=O}$ 1730, 1660 – 1630 |
| CH$_2$=CHCH$_2$–N⟨piperazinone⟩N–COCl | " | $\nu_{C=O}$ 1720, 1640 |

Table 2-continued

Reactive derivatives of (III)

$$A-N\underset{(R^2\ \ R^3)_m}{\overset{(X)_n}{\diagdown\diagup}}N-\overset{Y}{\underset{\|}{C}}OH$$

| Compound | Physical property | I.R. (cm$^{-1}$) |
|---|---|---|
| CH$_2$=CHCH(CH$_3$)—N(piperazinone)—COCl | " | $\nu_{C=O}$ 1730, 1650 |
| CH$_2$=C(CH$_3$)CH$_2$—N(piperazinone)—COCl | " | $\nu_{C=O}$ 1730, 1650 |
| CH$_3$CH=CHCH$_2$—N(piperazinone)—COCl (trans-) | " | $\nu_{C=O}$ 1730, 1650 |
| morpholino-CH$_2$—N(piperazinone)—COCl | m.p. 150° C (decomp.) | $\nu_{C=O}$ 1670, 1720 |
| CH$_3$CO—N(2,5-dioxopiperazine)—COCl | Oily material | $\nu_{C=O}$ 1790, 1720 – 1670 |
| C$_6$H$_5$CO—N(2,5-dioxopiperazine)—COCl | " | $\nu_{C=O}$ 1790, 1710, 1670 |
| CH$_3$—N(2,5-dioxopiperazine)—COCl | " | $\nu_{C=O}$ 1790, 1710 – 1660 |
| C$_6$H$_5$CH$_2$—N(2,5-dioxopiperazine)—COCl | " | $\nu_{C=O}$ 1790, 1710 – 1660 |
| CH$_3$—N(2,3-dioxopiperazine)—COCl | m.p. 94 – 95° C (decomp.) (from CH$_2$Cl$_2$—Et$_2$O) | $\nu_{C=O}$ 1790, 1680 |
| CH$_3$COOCH$_2$CH$_2$—N(2,3-dioxopiperazine)—COCl | Oily material | $\nu_{C=O}$ 1790, 1720, 1670 |
| CH$_3$CH$_2$—N(2,3-dioxopiperazine)—COCl | m.p. 95 – 96° C (decomp.) (from AcOBu) | $\nu_{C=O}$ 1780, 1660 |

Table 2-continued

Reactive derivatives of $$A-N\underset{(R^2)\quad R^3{}_m}{\overset{(X)_n}{\underset{\phantom{X}}{\bigcirc}}}N-\overset{Y}{\underset{\|}{C}}OH \qquad (III)$$

| Compound | Physical property | I.R. (cm⁻¹) |
|---|---|---|
| CH₃CH₂CH₂—N(piperazine-2,3-dione)—COCl | Oily material | $\nu_{C=O}$ 1780, 1710 – 1640 |
| CH₃(CH₂)₂CH₂—N(piperazine-2,3-dione)—COCl | " | $\nu_{C=O}$ 1780, 1660 |
| (CH₃)₂CH—N(piperazine-2,3-dione)—COCl | m.p. 130 –131° C (decomp.) | $\nu_{C=O}$ 1780, 1660 |
| CH₃(CH₂)₃CH₂—N(piperazine-2,3-dione)—COCl | Oily material | $\nu_{C=O}$ 1790, 1720 – 1665 |
| CH₃(CH₂)₄CH₂—N(piperazine-2,3-dione)—COCl | " | $\nu_{C=O}$ 1780, 1720 – 1640 |
| CH₃(CH₂)₅CH₂—N(piperazine-2,3-dione)—COCl | " | $\nu_{C=O}$ 1780, 1720 – 1640 |
| CH₃(CH₂)₆CH₂—N(piperazine-2,3-dione)—COCl | " | $\nu_{C=O}$ 1780, 1720 – 1640 |
| CH₂=CHCH₂—N(piperazine-2,3-dione)—COCl | Crystal | $\nu_{C=O}$ 1775, 1660 – 1620 |
| C₆H₅—N(piperazine-2,3-dione)—COCl | " | $\nu_{C=O}$ 1785, 1720 – 1650 |
| ClCH₂CH₂—N(piperazine-2,3-dione)—COCl | Oily material | $\nu_{C=O}$ 1790, 1720, 1680 |
| CH₃CH₂—N(piperazine-2,3-dione with CH₃ substituent)—COCl | m.p. 65 – 70° C (decomp.) | $\nu_{C=O}$ 1785, 1680 |

Table 2-continued

Reactive derivatives of (III)

$$A-N\underset{(R^2}{\overset{(X)_n}{\diagdown}}\underset{R^3)_m}{\overset{Y}{\diagup}}N-\overset{\overset{Y}{\|}}{C}OH$$

| Compound | Physical property | I.R. (cm$^{-1}$) |
|---|---|---|
| 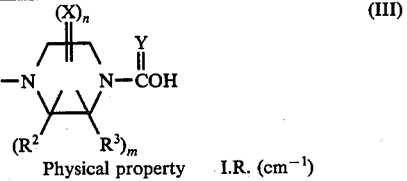 | m.p. 100 – 101° C (decomp.) | $\nu_{C=O}$ 1725, 1675 |
| 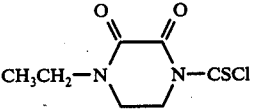 | m.p. 180 – 181° C | $\nu_{C=O}$ 1740, 1695 |
| 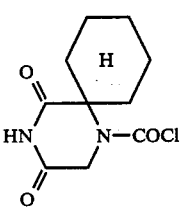 | m.p. 160 – 165° C | $\nu_{C=O}$ 1740, 1670 |
| 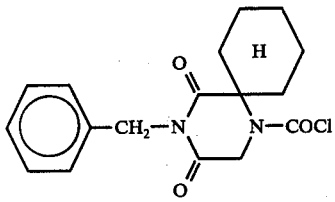 | Oily material | $\nu_{C=O}$ 1800, 1750, 1710 |
| 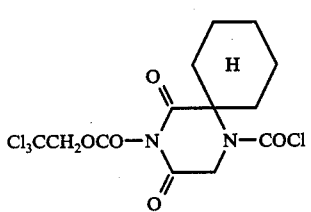 | m.p. 185 – 187° C (decomp.) | $\nu_{C=O}$ 1730, 1690 |
| 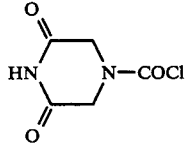 | Oily material | $\nu_{C=O}$ 1750, 1710 – 1685 |
| 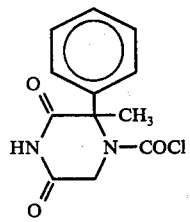 | " | $\nu_{C=O}$ 1735, 1725, 1710, 1675 |
| 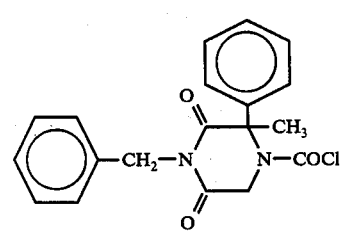 | | |

Note:
Et$_2$O = CH$_3$CH$_2$OCH$_2$CH$_3$
AcOBu = CH$_3$COO(CH$_2$)$_3$CH$_3$

The compound represented by the general formula (V) can be easily obtained by reacting, for example, a salt with an alkali metal, an alkaline earth metal or a nitrogen-containing organic base of an amino acid (IX)

(any of D-isomer, L-isomer and racemic compound) represented by the general formula (IX).

$$H_2N-R-COOH \qquad (IX)$$

wherein R is as defined previously, with a reactive derivative in the (thio)carboxyl group of a compound represented by the general formula (III) in a solvent inert to the reaction in the presence of an acid-binding agent. Preferable examples of the compound of formula (V) are D-isomers, L-isomers and racemic compounds of the following compounds, though it is needless to say that the examples are not limitative:

α-(4-Acetyl-2-oxo-1-piperazinocarbonylamino)-phenylacetic acid
α-(4-Chloroacetyl-2-oxo-1-piperazinocarbonylamino)-phenylacetic acid
α-(4-Dichloroacetyl-2-oxo-1-piperazinocarbonylamino)phenylacetic acid
α-(4-Palmitoyl-2-oxo-1-piperazinocarbonylamino)-phenylacetic acid
α-(4-Caproyl-2-oxo-1-piperazinocarbonylamino)-phenylacetic acid
α-(4-Capryloyl-2-oxo-1-piperazinocarbonylamino)-phenylacetic acid
α-(4-Enanthoyl-2-oxo-1-piperazinocarbonylamino)-phenylacetic acid
α-(4-Cyclohexanecarbonyl-2-oxo-1-piperazinocarbonylamino)phenylacetic acid
α-(4-Benzoyl-2-oxo-1-piperazinocarbonylamino)-phenylacetic acid
α-(4-p-chlorobenzoyl-2-oxo-1-piperazinocarbonylamino)phenylacetic acid
α-(4-p-Methoxybenzoyl-2-oxo-1-piperazinocarbonylamino)phenylacetic acid
α-[4-(3,4,5-Trimethoxybenzoyl)-2-oxo-1-piperazinocarbonylamino]phenylacetic acid
α-[4-(2,4-Dichlorobenzoyl)-2-oxo-1-piperazinocarbonylamino]phenylacetic acid
α-(4-Acetyl-3-methyl-2-oxo-1-piperazinocarbonylamino)phenylacetic acid
α-(4-Methanesulfonyl-2-oxo-1-piperazinocarbonylamino)phenylacetic acid
α-(4-Acetylaminocarbonyl-2-oxo-1-piperazinocarbonylamino)phenylacetic acid
α-(4-Phenylaminocarbonyl-2-oxo-1-piperazinocarbonylamino)phenylacetic acid
α-(4-Ethoxycarbonyl-2-oxo-1-piperazinocarbonylamino)phenylacetic acid
α-(4-Pivaloyloxymethyl-2-oxo-1-piperazinocarbonylamino)phenylacetic acid
α-(4-n-Hexyl-2-oxo-1-piperazinocarbonylamino)-phenylacetic acid
α-(4-n-Butyl-2-oxo-1-piperazinocarbonylamino)-phenylacetic acid
α-(4-n-Butyl-6-methyl-2-oxo-1-piperazinocarbonylamino)phenylacetic acid
α-(4-n-Octyl-2-oxo-1-piperazinocarbonylamino)-phenylacetic acid
α-(3-Oxo-1-piperazinocarbonylamino)phenylacetic acid
α-(2,5-Dimethyl-3-oxo-1-piperazinocarbonylamino)-phenylacetic acid
α-(5-Methyl-3-oxo-1-piperazinocarbonylamino)-phenylacetic acid
α-(2-Ethoxycarbonylmethyl-3-oxo-1-piperazinocarbonylamino)phenylacetic acid
α-(2-Methyl-3-oxo-1-piperazinocarbonylamino)-phenylacetic acid
α-(4-Acetyl-2-methyl-3-oxo-1-piperazinocarbonylamino)phenylacetic acid,
α-(4-Phenylaminocarbonyl-3-oxo-1-piperazinocarbonylamino)phenylacetic acid
α-(4-Methyl-3-oxo-1piperazinocarbonylamino)-phenylacetic acid
α-(4-n-Butyl-3-oxo-1-piperazinocarbonylamino)-phenylacetic acid
α-(4-Ethyl-3-oxo-1-piperazinocarbonylamino)-phenylacetic acid
α-(4-Isopropyl-3-oxo-1-piperazinocarbonylamino)-phenylacetic acid
α-(4-n-Pentyl-3-oxo-1-piperazinocarbonylamino)-phenylacetic acid
α-(4-iso-Pentyl-3-oxo-1-piperazinocarbonylamino)-phenylacetic acid
α-(4-n-Hexyl-3-oxo-1-piperazinocarbonylamino)-phenylacetic acid
α-(4-n-Heptyl-3-oxo-1-piperazinocarbonylamino)-phenylacetic acid
α-(4-n-Octyl-3-oxo-1-piperazinocarbonylamino)-phenylacetic acid
α-(4-n-Dodecyl-3-oxo-1-piperazinocarbonylamino)-phenylacetic acid
α-(4-Cyclopentyl-3-oxo-1-piperazinocarbonylamino)-phenylacetic acid
α-(2-Methyl-4-n-butyl-3-oxo-1-piperazinocarbonylamino)phenylacetic acid
α-(4-n-Butyl-5-methyl-3-oxo-1-piperazinocarbonylamino)phenylacetic acid
α-(4-n-Butyl-6-methyl-3-oxo-1-piperazinocarbonylamino)phenylacetic acid
α-(2-Phenyl-3-oxo-1-piperazinocarbonylamino)-phenylacetic acid
α-(4-Benzyl-3-oxo-1-piperazinocarbonylamino)-phenylacetic acid
α-(4-Carbamoyl-2-methyl-3-oxo-1-piperazinocarbonylamino)phenylacetic acid
α-(4-β-Hydroxyethyl-3-oxo-1-piperainocarbonylamino)phenylacetic acid
α-(4-Allyl-3-oxo-1-piperazinocarbonylamino)-phenylacetic acid
α-(4-α-Methylallyl-3-oxo-1-piperazinocarbonylamino)phenylacetic acid
α-(4-β-Methylallyl-3-oxo-1-piperazinocarbonylamino)-phenylacetic acid
α-[4-(Trans-2-butenyl)-3-oxo-1-piperazinocarbonylamino]phenylacetic acid
α-(4-Morpholinomethyl-3-oxo-1-piperazinocarbonylamino)phenylacetic acid
α-(4-Ethyl-3-oxo-1-piperazinocarbonylamino)-propionic acid
α-(4-Acetyl-2,5-dioxo-1-piperazinocarbonylamino)-phenylacetic acid
α-(4-Benzoyl-2,5dioxo-1-piperazinocarbonylamino)-phenylacetic acid
α-(4-Methyl-2,5-dioxo-1-piperazinocarbonylamino)-phenylacetic acid
α-(4-Benzyl-2,5-dioxo-1-piperazinocarbonylamino)-phenylacetic acid
α-(4-Methyl-2,3-dioxo-1-piperazinocarbonylamino)-phenylacetic acid
α-(4-Acetoxyethyl-2,3-dioxo-1-piperazinocarbonylamino)phenylacetic acid
α-(4-Ethyl-2,3-dioxo-1-piperazinocarbonylamino)-phenylacetic acid α-(4-n-Propyl-2,3-dioxo-1-piperazinocarbonylamio)-phenylacetic acid
α-(4-n-Butyl-2,3-dioxo-1-piperazinocarbonylamino)-phenylacetic acid
α-(4-Isopropyl-2,3-dioxo-1-piperazinocarbonylamino)phenylacetic acid
α-(4-n-Pentyl-2,3-dioxo-1-piperazinocarbonylamino)-phenylacetic acid
α-(4-n-Hexyl-2,3-dioxo-1-piperazinocarbonylamino)-phenylacetic acid
α-(4-n-Heptyl-2,3-dioxo-1-piperazinocarbonylamino)phenylacetic acid
α-(4-n-Octyl-2,3-dioxo-1-piperazinocarbonylamino)-phenylacetic acid
α-(4-Allyl-2,3-dioxo-1-piperazinocarbonylamino)-phenylacetic acid
α-(4-Phenyl-2,3-dioxo-1-piperazinocarbonylamino)-phenylacetic acid
α-(4-β-Chloroethyl-2,3-dioxo-1-piperazinocarbonylamino)phenylacetic acid
α-(4-Pyrrolidinoethyl-2,3-dioxo-1-piperazinocarbonylamino)phenylacetic acid
α-(4-Methyl-2,3-dioxo-1-piperazinocarbonylamino)-p-hydroxyphenylacetic acid
α-(4-Ethyl-2,3-dioxo-1-piperazinocarbonylamino)-p-hydroxyphenylacetic acid
α-(6-Methyl-4-ethyl-2,3-dioxo-1-piperazinocarbonylamino)phenylacetic acid
α-(4,6-Dimethyl-2,3-dioxo-1-piperazinocarbonylamino)phenylacetic acid
α-(4-Ethyl-2,3-dioxo-1-piperazinothiocarbonlyamino)phenylacetic acid
α-(4-Methyl-2,3-dioxo-1-piperazinocarbonylamino)-1,4-cyclohexadienylacetic acid
α-(4-Ethyl-2,3-dioxo-1-piperazinocarbonylamoino)-1,4-cyclohexadienylacetic acid
α-(4-n-Propyl-2,3-dioxo-1-piperazinocarbonylamino)-1,4-cyclohexadienylacetic acid
α-(4-n-Butyl-2,3-dioxo-1-piperazinocarbonylamino-1,4-cyclohexadienylacetic acid
α-(4-Methyl-2,3-dioxo-1-piperazinocarbonylamino-2-thienylacetic acid
α-(4-Ethyl-2,3-dioxo-1-piperazinocarbonylamino)-2-thienylacetic acid
α-(4-n-Propyl-2,3-dioxo-1-piperazinocarbonylamino)-2-thienylacetic acid
α-(4-n-Butyl-2,3-dioxo-1-piperazinocarbonylamino)-2-thienylacetic acid
α-(2,2-Pentamethylene-3,5-dioxo-1-piperazinocarbonylamino)phenylacetic acid
α-(4-Benzyl-2,2-pentamethylene-3,5-dioxo-1-piperazinocarbonylamino)phenylacetic acid
α-(4-β,β,β-Trichloroethoxycarbonyl-2,2-pentamethylene-3,5-dioxo-1-piperazinocarbonylamino)-phenylacetic acid
α-(3,5-Dioxo-1-piperazinocarbonylamino)phenylacetic acid
α-(2-Methyl-2-phenyl-3,5-dioxo-1-piperazinocarbonylamino)phenylacetic acid
α-(4-Benzyl-2-methyl-3,5-dioxo-1-piperazinocarbonylamino)phenylacetic acid
α-(4-Methyl-2,3-dioxo-1-piperazinocarbonylamino)-phenylacetic acid As the reactive derivative in the carbonyl group of the compound represented by the general formula (V), there is used a reactive derivative of a carboxylic acid which is ordinarily used in the synthesis of acid amides. Such reactive derivatives includes, for example, acid halides, acid anhydrides, mixed acid anhydrides with organic or organic acids, active acid amides, acid cyanides, active esters, etc. Particularly, acid chlorides, mixed acid anhydrides and active acid amides are preferable. Examples of the mixed acid anhdrides are mixed acid anhydrides with substituted acetic acids, alkyl carbonic acids, aryl carbonic acids and aralkyl carbonic acids; examples of the active esters are cyanomethyl esters, substituted phenyl esters, substituted benzyl esters, substituted thienyl esters, etc.; and examples of the active acid amides are N-acyl saccharins, N-acyl imidazoles, N-acyl benzoylamides, N,N-dicyclohexyl-N-acylureas, N-acyl sulfonamides, etc.

Compounds of formula (VI) can be obtained by, for example, process (1) or (2). Some of the compounds obtained by process (3) can further be used as the starting compounds in process (3). Any of D-, L- and racemic compounds of formula (VI) may be used.

The modes of practice of the processes (1), (2) and (3) are explained below.

The processes (1) and (2) may be carried out under substantially the same conditions. That is, the compound of formula (II) or (IV) is dissolved or suspended in at least one inert solvent selected from, for example, water, acetone, tetrahydrofuran, dioxane, acetonitrile, dimethylformamide, methanol, ethanol, methoxyethanol, diethyl ether, isopropyl ether, benzene, toluene, methylene chloride, chloroform, ethyl acetate, methyl isobutyl ketone and the like. The resulting solution or suspension is reacted with a reactive derivative of the comopound of formula (III), or with the compound of formula (V) or a reactive derivative in the carboxyl group of the compound of formula (V) in the presence or absence of a base at a temperature in the range from $-60°$ to $80°$ C., preferably from $-40°$ to $30°$ C. The reaction time is ordinarily 5 minutes to 5 hours. Examples of the base used in the above reaction are inorganic bases such as alkali hydroxides, alkali hydrogencarbonates, alkali carbonates, alkali acetates, etc.; tertiary amines such as trimethylamine, triethylamine, tributylamine, pyridine, N-methylpiperidine, N-methylmorpholine, lutidine, collidine, etc.; and secondary amines such as dicyclohexylamine, diethylamine, etc. When the compound of formula (V) is used in the form of a free acid or salt in the process (2), the reaction of the process (2) may be effected in the presence of a dehydrating condensing agent such as N,N-dicyclohexyl carbodiimide, N-cyclohexyl-N'-morpholinoethyl carbodiimide, N,N'-diethyl carbodiimide, N.N'-carbonyl (2-methylimidazole), a trialkyl ester of phosphorous acid, ethyl ester of polyphosphoric acid, phosphorus oxychloride, phosphorus trichloride, 2-chloro1,3,2-dioxaphospholane or oxazolyl chloride. The salt of the compound of formula (V) includes alkali metal salts, alkaline earth metal salts, ammonium salts, and salts with organic bases such as trimethylamine, dicyclohexylamine and the like.

The process (3) is carried out in the manner described below.

When B in the formula (VI) is a group other than a hetero aromatic N-oxide thio group having a thio group on the carbon atom adjacent to the N-oxide group in the molecule, the compound of formula (VI) is reacted with the compound of formula (VII) or a tertiary amine in at least one solvent selected from, for example, water, methanol, ethanol, propanol, isopropanol, butanol, acetone, methyl ethyl ketone, methyl isobutyl ketone, tetrahydrofuran, dioxane, acetonitrile, ethyl acetate, methoxyethanol, dimethoxyethane, dimethylformamide, dimethyl sulfoxide, dichloromethane, chloroform, a dichloroethane, and the like. The above-mentioned reaction is preferably effected in a strongly polar solvent such as water or the like. In this case, the pH of the reaction solution is advantageously maintained at 2 to 10, preferably 4 to 8. The desired pH may be attained by addition of a buffer solution such as sodium phosphate. The reaction conditions are not particularly limited, though the reaction is ordinarily conducted at 0° to 100° C. over a period of several hours to tens hours. When B in the formula (VI) is a hetero aromatic N-oxide thio group having a thio group on the carbon atom adjacent to the N-oxide group in the molecule, the compound of formula (VI) is reacted with the compound of formula (VII) in the above-mentioned solvent in the presence of a cupric compound. This reaction is particularly useful where an alcohol is used such as methyl alcohol, ethyl alcohol, propyl alcohol, isopropyl alcohol, n-butyl alcohol, benzyl alcohol, ethylene glycol or the like as the compound of formula (VII). In this case, the reaction proceeds smoothly by using an excess of the alcohol per se to allow it to act as the reaction medium, too. The cupric compound used in this process includes organic and inorganic ones, such as cupric chloride, bromide, fluoride, nitrate, sulfate, borate, phosphate, cyanide, formate, acetayte, propionate, citrate, tartarate, benzoate, salicylate and the like. The amount of the cupric compound used is preferably ½ mole per mole of the compound of formula (VI). The reaction temperature and the reaction time may be varied depending upon the kinds of compound of formula (VI), cupric compound and compound of formula (VII), though they are usually selected from the range of 0° to 100° C and the range of several minutes to several days, respectively.

The reaction conditions to be adopted in the processes (1), (2) and (3) are not limited to those mentioned above, and can be properly varied depending upon the kinds of reaction reagents.

Further, the non-toxic salts of the general formula (I), in which $R^1$ is a salt-forming cation, can be easily obtained according to an ordinary procedure from compounds of the general formula (I), in which $R^1$ is a hydrogen atom or a blocking group.

Thus, among the compounds of formula (I) of the present invention, the pencillins can be easily obtained according to any of the aforesaid processes (1) and (2), while the cephalosporins can be easily obtained according to either the aforesaid process (1), (2) or (3).

The present pencillins and cephalosporins include concretely the following compounds though are not restricted thereto. The following pencillins can be produced by any of the aforesaid processes (1) and (2), and the following cephalosporins can be produced by any of the aforesaid processes (19, (2) and )3).

Penicillins:

6-[D(—)-α-(4-acetyl-2-oxo-1-piperazinocarbonylamino)phenylacetamido]penicillanic acid,
6-[D(—)-α-(4-dichloroacetyl-2-oxo-1-piperazioncarbonylamino)phenylacetamido]penicillanic acid,
6[D(—)-α-(4-enanthoy-2-oxo-1-piperazinocarbonylamino)phenylacetamido]penicillanic acid,
6-[D(—)-α-(4-cyclohexanecarbonyl-2-oxo-1-piperazinocarbonylamino)phenylacetamido]-penicillanic acid,
6-[D(—)-α-(4-acetyl-3-methyl-2-oxo-1-piperazinocarbonylamino)phenylacetamido]-penicillanic acid,
6-[D(—)-α-(4-methanesulfonyl-2-oxo-1-piperazinocarbonylamino)phenylacetamido]-penicillanic acid,
6-[D(—)-α-(4-n-hepxyl-2-oxo-1-piperazinocarbonylamino)phenylacetamido]penicillanic acid,
6-[D(—)-α-(4-n-butyl-2-oxo-1-piperazinocarbonylamino)phenylacetamido]penicillanic acid,
6-[D(—)-α-(4-n-butyl-6-methyl-2-oxo-1-piperazinocarbonylamino)phenylacetamido]-penicillanic acid,
6-[D(—)-α-(4-n-octyl-2-oxo-1-piperazinocarbonylamino)phenylacetamido]penicillanic acid,
6-[D(—)-α-(4-pivaloyloxymethyl-2-oxo-1-piperazinocarbonylamino)phenylacetamido]-penicillanic acid,
6-[D(—)-α-(4-palmitoyl-2-oxo-1-piperazinocarbonylamino)phenylacetamido]penicillanic acid,
6-[D(—)-α-(4-capryloxy-2-oxo-1-piperazioncarbonylamino)phenylacetamido]penicillanic acid,
6-[D(—)-α-(4-caproyl-2-oxo-1-piperazinocarbonylamino)phenylacetamido]penicillanic acid,
6-[D(—)-α-(4-chloroacetyl-2-oxo-1-piperazinocarbonylamino)phenylacetamido]penicillanic acid,
6-[D(—)-α-(4-benzoyl-2-oxo-1-piperazinocarbonylamino)phenylacetamido]penicillanic acid,
6-[D(—)-α-(4-p-chlorobenzoyl-2-oxo-1-piperazinocarbonylamino)phenylacetamido]-penicillanic acid,
6-[D(—)-α-(4-p-methoxybenzoyl-2-oxo-1-piperazinocarbonylamino)phenylacetamido]-penicillanic acid,
6-{D(—)-α-[4-(3,4,5-trimethoxybenzoyl)-2-oxo-1-piperazinocarbonylamino]phenylacetamido}•penicillanic acid,
6-{D(—)-α-[4-(2,4-dichlorobenzoyl)-2-oxo-1-piperazinocarbonylamino]phenylacetamido}•penicillanic acid,
6-[D(—)-α-(4-acetylaminocarbonyl-2-oxo-1-piperazinocarbonylamino)phenylacetamido]-penicillanic acid,
6-[D(—)-α-(4-phenylaminocarbonyl-2-oxo-1-piperazinocarbonylamino)phenylacetamido]-penicillanic acid,
6-[D(—)-α-(4-ethoxycarbonyl-2-oxo-1-piperazinocarbonylamino)phenyolacetamido]-penicillanic acid,
6-[D(—)-α-(4-methyl-3-oxo-1-piperazinocarbonylamino)phenylacetamido]penicillanic acid,
6-[D(—)-α-(4-n-butyl-3-oxo-1-piperazinocarbonylamino)phenylacetamido]penicillanic acid,
6-[D(—)-α-(4-ethyl-3-oxo-1-piperazinocarbonylamino)phenylacetamido]penicillanic acid,
6-[D(—)-α-(4-isopropyl-3-oxo-1-piperazinocarbonylamino)phenylacetamido]penicillanic acid,
6-[D(—)-α-(4-n-pentyl-3-oxo-1-piperazinocarbonylamino)phenylacetamido]penicillanic acid,
6-[D(—)-α-(4-iso-pentyl-3-oxo-1-piperazinocarbonylamino)phenylacetamido]penicillanic acid,
6-[D(—)-α-(2-methyl-4-n-butyl-3-oxo-1-piperazinocarbonylamino)phenylacetamido]-penicillanic acid,
6-[D(—)-α-(4-n-butyl-5-methyl-3-oxo-1-piperazinocarbonylamino)phenylacetamido]-penicillanic acid, 6-[D(—)-α-(4-n-butyl-6-methyl-3-oxo-1-piperazinocarbonylamino)phenylacetamido]penicillanic acid,
6-[D(—)-α-(4-benzyl-3-oxo-1-piperazinocarbonylamino)phenylacetamido]penicillanic acid,
6-[D(—)-α-(4-β-hydroxyethyl-3-oxo-1-piperazinocarbonylamino)phenylacetamido]penicillanic acid,
6-[D(—)-α-(4-acetyl-2-methyl-3-oxo-1-piperazinocarbonylamino)phenylacetamido]penicillanic acid,
6-[D(—)-α-(4-carbamoyl-2-methyl-3-oxo-1-piperazinocarbonylamino)phenylacetamido]penicillanic acid,
6-[D(—)-α-(3-oxo-1-piperazinocarbonylamino)phenylacetamido]penicillanic acid,
6-[D(—)-α-(2,5-dimethyl-3-oxo-1-piperazinocarbonylamino)phenylacetamido]penicillanic acid,
6-[D(—)-α-(5-methyl-3-oxo-1-piperazinocarbonylamino)phenylacetamido]penicillanic acid,
6-[D(—)-α-(2-ethoxycarbonylmethyl-3-oxo-1-piperazinocarbonylamino)phenylacetamido]penicillanic acid,
6-[D(—)-α-(2-methyl-3-oxo-1-piperazinocarbonylamino)phenylacetamido]penicillanic acid,
6-[D(—)-α-(4-ethyl-3-oxo-1-piperazinocarbonylamino)propionamido]penicillanic acid,
6-[D(—)-α-(4-allyl-3-oxo-1-piperazinocarbonylamino)phenylacetamido]penicillanic acid,
6-[D(—)-α-(4-α-methylallyl-3-oxo-1-piperazinocarbonylamino)phenylacetamido]penicillanic acid,
6-[D(—)-α-(4-β-methylallyl-3-oxo-1-piperazinocarbonylamino)phenylacetamido]penicillanic acid,
6-{D(—)-α-[4-(trans-2-butenyl)-3-oxo-1-piperazinocarbonylamino]phenylacetamido}·penicillanic acid,
6-[D(—)-α-(4-n-hexyl-3-oxo-1-piperazinocarbonylamino)phenylacetamido]penicillanic acid,
6-[D(—)-α-(4-n-heptyl-3-oxo-1-piperazinocarbonylamino)phenylacetamido]penicillanic acid,
6-[D(—)-α-(4-n-octyl-3-oxo-1-piperazinocarbonylamino)phenylacetamido]penicillanic acid,
6-[D(—)-α-(4-n-dodecyl-3-oxo-1-piperazinocarbonylamino)phenylacetamido]penicillanic acid,
6-[D(—)-α-(4-cyclopentyl-3-oxo-1-piperazinocarbonylamino)phenylacetamido]penicillanic acid,
6-[D(—)-α-(4-phenylaminocarbonyl-3-oxo-1-piperazinocarbonylamino)phenylacetamido]penicillanic acid,
6-[D(—)-α-(2-phenyl-3-oxo-1-piperazinocarbonylamino)phenylacetamido]penicillanic acid,
6-[D(—)-α-(4-morpholinomethyl-3-oxo-1-piperazinocarbonylamino)phenylacetamido]penicillanic acid,
6-[D(—)-α-(4-acetyl-2,5-dioxo-1-piperazinocarbonylamino)phenylacetamido]penicillanic acid,
6-[D(—)-α-(4-benzoyl-2,5-dioxo-1-piperazinocarbonylamino)phenylacetamido]penicillanic acid,
6-[D(—)-α-(4-methyl-2,5-dioxo-1-piperazinocarbonylamino)phenylacetamido]penicillanic acid,
6-[D(—)-α-(4-benzyl-2,5-dioxo-1-piperazinocarbonylamino)phenylacetamido]penicillanic acid,
6-[D(—)-α-(4-ethyl-2,3-dioxo-1-piperazinocarbonylamino)phenylacetamido]penicillanic acid,
6-[D(—)-α-(4-methyl-2,3-dioxo-1-piperazinocarbonylamino)phenylacetamido]penicillanic acid,
6-[D(—)-α-(4-n-propyl-2,3-dioxo-1-piperazinocarbonylamino)phenylacetamido]penicillanic acid,
6-[D(—)-α-(4-n-butyl-2,3-dioxo-1-piperazinocarbonylamino)phenylacetamido]penicillanic acid,
6-[D(—)-α-(4-iso-propyl-2,3-dioxo-1-piperazinocarbonylamino)phenylacetamido]penicillanic acid,
6-[D(—)-α-(4-acetoxyethyl-2,3-dioxo-1-piperazinocarbonylamino)phenylacetamido]penicillanic acid,
6-[D(—)-α-(4-allyl-2,3-dioxo-1-piperazinocarbonylamino)phenylacetamido]penicillanic acid,
6-[D(—)-α-(4-phenyl-2,3-dioxo-1-piperazinocarbonylamino)phenylacetamido]penicillanic acid,
6-[D(—)-α-(4-β-chloroethyl-2,3-dioxo-1-piperazinocarbonylamino)phenylacetamido]penicillanic acid,
6-[D(—)-α-(6-methyl-4-ethyl-2,3-dioxo-1-piperazinocarbonylamino)phenylacetamido]penicillanic acid,
6-[D(—)-α-(4,6-dimethyl-2,3-dioxo-1-piperazinocarbonylamino)phenylacetamido]penicillanic acid,
6-[D(—)-α-(4-n-pentyl-2,3-dioxo-1-piperazinocarbonylamino)phenylacetamido]penicillanic acid,
6-[D(—)-α-(4-n-hexyl-2,3-dioxo-1-piperazinocarbonylamino)phenylacetamido]penicillanic acid,
6-[D(—)-α-(4-n-heptyl-2,3-dioxo-1-piperazinocarbonylamino)phenylacetamido]penicillanic acid,
6-[D(—)-α-(4-n-octyl-2,3-dioxo-1-piperazinocarbonylamino)phenylacetamido]penicillanic acid,
6-[(D(—)-α-(4-ethyl- 2,3-dioxo-1-piperazinothiocarbonylamino)phenylacetamido]pneicillanic acid.
6-[D(—)-α-(4-methyl-2,3-dioxo-1-piperazinocarbonylamino)-p-hydroxyphenylacetamido]penicillanic acid,
6-[D(—)-α-(4-ethyl-2,3-dioxo-1-piperazinocarbonylamino)-p-hydroxyphenylacetamido]penicllanic acid,
6-[D(—)-α-(4-methyl-2,3-dioxo-1-piperazinocarbonylamino)-1,4-cyclohexadienylacetamido]penicllanic acid,
6-[D(—)-α-(4-ethyl-2,3-dioxo-1-piperzinocarbonylamino)-1,4-cyclohexadienylacetamido]penicillanic acid,
6-(D(—)-α-(4-n-propyl-2,3-dioxo-1-piperazinoarbonylamino)-1,4-cyclohexadienylacetamido]penicillanic acid,
6-[D(—)-α-(4-n-butyl-2,3-dioxo-1-piperazinocarbonylamino)-1,4-cyclohexadienylacetamido]penicillanic acid,
6-[DL-α-(4-methyl-2,3-dioxo-1-piperazinocarbonylamino)-2-thienylacetamido]penicillanic acid,
6-[DL-α-(4-ethyl-2,3-dioxo-1-piperazinocarbonylamino)-2-thienylacetamido]penicillanic acid,
6-[DL-α-(4-n-propyl-2,3-dioxo-1-piperadinocarbonylamino)-2-thienylacetamido]penicillanic acid,
6-[DL-α-(4-n-butyl-2,3-dioxo-1-piperazinocarbonylamino)-2-thienylacetamido]penicillanic acid,
6-[D(—)-α-(2,2-pentamethylene-3,5-dioxo-1-piperazinocarbonylamino)phenylacetamido]penicillanic acid,
6-[D(—)-α-(3,5-dioxo-1-piperazinocarbonylamino)phenylacetamido]penicillanic acid,
6-[D(—) -α-(2-methyl-2-phenyl-3,5-dioxo-1-piperazinocarbonlamino)phenylacetamido]penicllanic acid,
6-D(—)-α-(4-benzyl-2,2-pentamethylene-3,5-dioxo-1-piperazinocarbonylamino)phenylacetamido]penicillanic acid, 6-[D(—)-α-(4-β,β,β-trichlorethoxycarbonyl-2,2-pentamethyllene-3,5-dioxo-1-piperazinocarbonylamino)-phenylacetamido]penicillanic acid, 6-[D(—) -α-(4-benzyl-2-methyl-2-phenyl-3,5-dioxo-1piperazinocarbonylamino)phenylacetamido]-penicillanic acid, pivaloyloxymethyl 6-[D(—)-α-(2-methyl-3-oxo-1-piperazinocarbonylamino)phenylacetamido]-penicillanate, phthalidyl 6-[D(—)-α-(4-methyl-2,3-dioxo-1-piperazinocarbonylamino)phenylacetamido]-penicillanate, phthalidyl 6-[D(—)-α-(4-ethyl-2,3-dioxo-1-piperazinocarbonylamino)phenylacetamido]-penicillanate, phthalidyl 6-[D(—)-α-(4-iso-propyl-2,3-dioxo-1-piperazinocarbonylamino)phenylacetamido]-penicillanate, phthalidyl 6-[D(—)-α-(4-N-butyl-2,3-dioxo-1-piperazinocarbonylamino)phenylacetamido]-penicillnate, methoxymethyl 6-[D(—)-α-(4-methyl-2,3-dioxo-1-piperazinocarbonylamino)phenylacetamido]-penicillanate, methoxymethyl 6-[D(—)-α-(4-ethyl-2,3-dioxo-1-piperazinocarbonylamino)phenylacetamido]-penicillante, methoxymethyl 6-[D(—)-α-(4-n-butyl-2,3-dioxo-1-piperazinocarbonylamino)phenylacetamido]-penicillanate, methoxymethyl 6-[D(—)-α-(4-iso-propyl-2,3-dioxo-1-piperazinocarbonylamino)phenylacetamido]-penicillnate, methoxymethyl 6-[D(—)-α-(4-n-octyl-2,3-dioxo-1-piperazinocarbonylamino)phenylacetamido]-penicillanate, pivaloyloxymethyl 6-[D(—)-α-(4-methyl-2,3-dioxo-1-piperazinocarbonylamino)phenylacetamido]-penicillnate, pivaloloxymethyl 6-[D(—)-α-(4-ethyl-2,3-dioxo-1 pivaloyloxymethyl 6-[D(—)-α-(4-n-octyl-2,3-dioxo-1piperazinocarbonylamino)phenylacetamido]-penicillanate, β-piperidinoethyl 6-[D(—)-α-(4-methyl-2,3-dioxo-1piperazinocarbonylamino)phenylacetamido]-penicillanate, β-piperidinoethyl 6-[D(—)-α-(4-n-octyl-2,3-dioxo-1piperazinocarbonylamino)phenylacetamido]-penicillanate, β-morpholinoethyl 6-[D(—)-α-(4-methyl-2,3-dioxo-1-piperazinocarbonylamino)phenylacetamido]pencillanate, etc.

β-morpholinoethyl 6-[D(—)-α-(4-n-octyl-2,3-dioxo-1piperzinocarbonylamino)phenylacetamido]pencillanate, etc.

CEPHALOSPORINS:

7-[D(—)-α-(4-methyl-2,3-dioxo-1-piperazinocarbonylamino)phenylacetamido]-3-methyl-$\Delta^3$-cephem-4-carboxylic acid, 7-[D(—)-α-(4-ethyl-2,3-dioxo-1-piperazinocarbonylamino)phenylacetamido]-3-methyl-$\Delta^3$-cephem-4-carboxylic acid, 7-[D(—)-α-(4-n-propyl-2,3-dioxo-1-piperazinocarbonylamino)phenylacetamido]-3-methyl-$\Delta^3$-cephem-4-carboxylic acid, 7-[D(—)-α-(4-n-butyl-2,3-dioxo-1-piperazinocarbonylamino)phenylacetamido]-3-methyl-$\Delta^3$-cephem-4-carboxylic acid, 7-[D(—)-α-(4-n-pentyl-2,3-dioxo-1-piperazinocarbonylamino)phenylacetamido]-3-methyl-$\Delta^3$-cephem-4-carboxylic acid, 7-[D(—)-α-(4-n-hexyl-2,3-dioxo-1-piperazinocarbonylamino)phenylacetamido]-3-methyl-$\Delta^3$-cephem-4-carboxylic acid, 7-[D(—) -α-(4-n-heptyl-2,3-dioxo-1-piperazinocarbonylamino)phenylacetamido]-3-methyl-$\Delta^3$-cephem-4-carboxylic acid, 7-[D(—)-α-(4-n-octyl-2,3-dioxo-1-piperazinocarbonylamino)phenylacetaido]-3-methyl-$\Delta^3$-cephem-4-carboxylic acid, 7-[D(—)-α-(4-methyl-2,3-dioxo-1-piperazinocarbonylamino)phenylacetamido]-3-acetoxymethyl-$\Delta^3$-cephem-4-carboxylic acid.

7-[D(—)-α-(4-n-propyl-2,3-dioxo-1-periazinocarbonylamino)phenylacetamido]-3-acetoxymethyl-$\Delta^3$-cephem-4-carboxylic acid, 7-[D(—)-α-(4-ethyl-2,3-dioxo-1-piperazinocarbonylamino)phenylacetamido]-3-acetoxymethyl-$\Delta^3$-cephem-4carboxylic acid, 7-[D(—)-α-(4-iso-propyl-2,3-dioxo-1-piperazinocarbonylamino)phenylacetamido]-3-acetoxymethyl-$\Delta^3$-cephem-4-carboxylic acid, 7-[D(—)-α-(4-ethyl-2,3-dioxo-1-piperazinothiocarbonylamino)phenylacetamido]-3-acetoxymethyl-$\Delta^3$-cephem-4carboxylic acid, 7-[D(—)-α-(4-methyl-2,3-dioxo-1-piperazinothiocarbonylamino)phenylacetamido]-3-acetoxymethyl-$\Delta^3$-cephem-4carboxylic acid, 7-[D(—)-α-(4-methyl:2,3-dioxo-1-piperazinocarbonylamino)phenylacetamido]-3-[2-(5-methyl-1,3,4-thiadiazolyl)-thiomethyl]-$\Delta^3$-cephem-4-carboxylic acid, 7-[D(—)-α-(4-ethyl-2,3-dioxo-1-piperazinocarbonylamino)phenylacetamido]-3-[2-(5-methyl-1,3,4-thiadiaolyl]-$\Delta^3$-cephem-4-carboxylic acid, 7-[D(—)-α-(4-n-propyl-2,3-diox-1-piperazinocarbonylamino)phenylacetamido]-3-[2-(5-methyl-1,3,4-thiadiazolyl)-triomethyl]-$\Delta^3$-cephem-4-carboxylic acid, 7-[D(—)-α-(4-n-butyl-2,3-dioxo-1-ipierazinocarbonylamino)phenylacetamido]-3-[2-(5-methyl-1,3,4-thiadiazolyl)-thiomethyl]-$\Delta^3$-cephem-4-carboxylic acid, 7-[D(—)-60 -(4-phenyl-2,3-dioxo-1-piperazinocarbonylamino)phenylacetamido]-3-[2-(5-methyl-1,3,4-thiadiazolyl)-thiomethyl]-$\Delta^3$-cephem-4-carboxylic acid, 7-[D(—)-α-(4-methyl-2,3-dioxo-1-piperazinocarbonyl)-thiomethyl]-$\Delta^3$-cephem-4-carboxylic acid, 7[D(—)-α-(4-ethyl-6-methyl-2,3-dioxo-1-piperazinocarbonylamino)phenylacetamido]-3-[5-(1m-methyl-1,2,3,4-tetrazolyl)-thiomethyl]-$\Delta^3$-cephem-4-carboxylic acid, 7-[D(—)-α-(4,6-dimethyl-2,3-dioxo-1-piperazinocarbonylamino)phenylacetamido]-3-[5-(1-methyl-1,2,3,4-tetrazolyl)-thiomethyl]-$\Delta^3$-cephem-4-carboxylic acid, 7-[D(—)-α-(4-phenyl-2,3-dioxo-1-piperazinocarbonylamino)phenylacetamido]-3-[5-[5-(1-methyl-1,2,3,4-tetrazolyl)-thiomethyl]-$\Delta^3$-cephem-4-carboxylic acid, 7-[D(—)-α-(4-methyl-2,3-dioxo-1-piperazinocarbonylamino)phenylacetamido]-3-[5-(1,3,4- thiadiazolyl)-thiomethyl]-Δ³-cephem-4-carboxylic acid,

7-[D(—)-α-(4-ethyl-2,3-dioxo-1-piperazinocarbonylamino)phenylacetamido]-3-[5-(1,3,4-thiadiazolyl)-thiomethyl]-Δ³-cephem-4-carboxylic acid, 7-[D(—)-α-(4-methyl-2,3-dioxo-1-piperazinocarbonylamino)phenylacetamido]-3-[2-(1-methyl-1,3,4-triazolyl)-thiomethyl] Δ³-cephem-4-carboxylic acid, 7-[D(—)-α-(4-ethyl-22,3-dioxo-1-piperazinocarbonylamino)phenylacetamido]-3-[2-(1-methyl-1,3,4-triazolyl)-thiomeethyl]-Δ³-cephem-4-carboxylic acid, 7-[D(—)-α-(4-phenyl-2,3-dioxo-1-piperazinocarbonylamino)phenylacetamido]-3-[2-[1-methyl-1,3,4-triazolyl)-thiomethyl]-Δ³-cephem-4-carboxylic acid, 7-[D(—)-α-(4-methyl-2,3-dioxo-1-piperazinocarbonylamino)propionamido ] -3-acetoxylmethyl-Δ³-cephem-4-carboxylic acid, 7[D(—)-α-(4-methyl-2,3-dioxo-1-piperazinocarbonylamido)-p-hydroxyphenylacetamido]-3-[5-(1-methyl-1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-azidomethyl-Δ³-cephem-4-carboxylic acid, 7-[D(—)-α-(4-ethyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4methyl-2,3-dioxo-1-piperazinocarbonylamino)phenylacetamido]-3-[2-(1,3,4-triazolyl)-triomethyl]-Δ³-cephem-4-carboxylic acid, 7-[D(—)-α-(4-methyl-2,3-dioxo-1-piperazinocarbonylamino)phenylacetamido]-3-[5-(1,2,3,4-tetrazolyl)-thiomethyl]-Δ³-cephem-4-carboxylic acid, 7-[D(—)-α-(4-ethyl-2,3-dioxo-1-piperazinocarbonylamino)phenylacetamido]-3-[5-(1,2,3,4-tetrazolyl)-thiomeethyl]-Δ³-cephem-4-carboxylic acid, 7-[D(—)-α-(4-methyl-2,3-dioxo-1-piperazinocarbonyl amino)phenylacetamido]-3-[2-(5-methyl-1,3,4-oxadiazolyl)-thiomethyl]-6³-cephem-4-carboxylic acid, 7-[D(—)-α-(4-methyl-2,3-dioxo-1-piperazinocarbonylamino)phenylacetamido]-3-[3-(2,6-dimethyl-5-oxo-2,5-dihydro 1,2,4-triazinylthiomethyl]-Δ³-cephem-4-carboxylic acid, 7-[D(—)-α-(4-ethyl-2,3-dioxo-1-piperazinocarbonylamino)phenylacetamido]-3-[2-(4-methyloxazolyl)-thiomethyl]-Δ³-cephem-4-carboxylic acid, 7-[D(—)-α-(4-methyl-2,3-dioxo-1-piperazinocarbonylamino)phenylacetamido]-3-[2-(4-methylthiazolyl)-thiomethyl]-Δ³cephem-4-carboxylic acid, 7-[D(—)-α-(4-ethyl-2,3-dioxo-1-piperazinocarbonylamino)phenylacetamido]-3-[2-(pyridyl-1-oxide)-thiomethyl]-Δ³-cephem-4-carboxylic acid, 7-[D(—)-α-(4-methyl-2,3-dioxo-1-piperazinocarbonylamino)phenylacetamido]-3-(2-thiazolinylthiomethylΔ³-cephem-4-carboxylic acid, 7-[D(31)-α-(4-methyl-2,3-dioxo-1-piperazinocarbonylamino)phenyoacetamido]-3-[2-(1methylimidazolyl)-thiomethyl]-Δ³-cephem-4-carboxylic acid, 7-[D(—)-α-(4-methyl-2,3-dioxo-1-piperzinocarbonylamino)phenylacetamido]-3-(2-pyrimidinyl-thiomethyl)-Δ³-cephem-4-carboxylic acid, 7-[D(—)-α-(4-ethyl-2,3-dioxo-1-piperainocarbonylamino)phenylacetamido]-3-[3-(6-methylpyridazinyl)-thiomethyl]-Δ³-cephem-4-carboxylic acid, 7-D(—)-α-(4-methyl-2,3-dioxo-1-piperazinocarbonylamino)phenylacetamido]-3-[1-(4-methylpiperazino)-thiocarbonylthiomethyl]-Δ³-cephem-4-carboxylic acid, 4-[D(—)-α-(4-methyl-2,3dioxo-1-piperazinocarbonylamino)phenylacetamido]-3-[5-(3-methylisoxazolyl)-carbonylthiomethyl]-Δ³-cephem-4-carboxylic acid, 7-[D(—)-α-(4-methyl-2,3-dioxo-1-piperazinocarbonylamino)phenykacetamido]-3-ethoxythiocarbonylthiomethylΔ³-cephem-4-carboxylic acid, 7-[D(—)-α-(4-ethoxycarbonyl-2-oxo-1piperazinocarbonylamino)phenylacetamido]-3-methyl-Δ³-cephem-4-carboxylic acid, 7-[D(—)-α-(4-n-hexyl-3-oxo-1-piperazinocarbonylamino)-phenylacetamido]-3-methyl-Δ³-cephem-4-carboxylic acid, 7-[D(—)-α-(4-acetyl-2-oxo-1-piperazinocarbonylamino)-phenylacetamido]-3-[2-(5-methyl-1,3,4-thiadiazolyl)-thiomethyl]-Δ³-cephem-4-carboxylic acid, 7-[D(—)-α-(4-methanesulfonyl-2-oxo-1-piperazino carbonylamino)phenylacetamido]-Δ³-cephem-4-carboxylic acid, 7-[D(—)-α-(4-methyl-2-oxo-1-piperazinocarbonylamino)-phenylacetamido]-3-[2-(5-methyl-1,3,4-thiadiazolyl)-thiomethyl]-Δ³-cephem-4-carboxylic acid, 7-[D(—)-α-(4-ethyl-2-oxo-1-piperazinocarbonylamino)-phenylacetamido]-3-[2-(5-methyl-1,3,4-thiadiazolyl)-thiomethyl]-Δ³-cephem-4-carboxylic acid, 7-[D(—)-α-(4-acetylaminocarbonyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-methyl-3-oxo-1-piperazinocarbonylamino)-phenylacetamido]-3-[2-(5-methyl-1,3,4-thiadiazolyl)-thiomethyl]-Δ³-cephem-4-carboxylic acid, 7-[D(—)-α-(4-ethyl-3-oxo-1-piperazinocarbonylamino)-phenylacetamido]-3-[1-(5-methyl-1,3,4-thiadiazolyl)-thiomethyl]-Δ³-cephem-4-carboxylic acid, 7-[D(—)-α-(3,5-dioxo-1-piperazinocarbonylamino)-phenylacetamido]-3-[2-(5-methyl-1,3,4-thiadiazolyl)-thiomethyl]-Δ³-cephem-4-carboxylic acid, 7-[D(—)-α-(4-acetyl-2,5-dioxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-acetyl-2-oxo-1-piperazinocarbonylamino)-phenylacetamido]-3-[5-(1-methyl-1,2,3,4-tetrazolyl)-thiomethyl]-Δ³-cephem-4-carboxylic acid, 7-[D(—)-α-(4-methanesulfonyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-ethyl-2-oxo-1-piperazinocarbonylamino)-phenylacetamido]-3-[5-(1-methyl-1,2,3,4-tetrazoyl)-thiomethyl]-Δ³-cephem-4-carboxylic acid, 7-[D(—)-α-(4-acetylaminocarbonyl-2-oxo-1-piperazinocarbonylamino)phenylacetamido]-3-[5-(1-methyl-1,2,3,4-tetrazolyl-thiomethyl]-Δ³-cephem-4-carboxylic acid, 7-[D(—)-α-(4-methyl-3-oxo-1-piperazinocarbonylamono)phenylacetamido]-3-[5-(1-methyl-1,2,3,4-tetrazolyl)-thiomethyl]-Δ³-cephem-4-carboxylic acid, 7-[D(—)-α-(4-ethyl-3-oxo-1-piperazinocarbonylamino)-phenylacetamido]-3-[5-(1-methyl-1,2,3,4-tetrazolyl)-thiomethyl]-Δ³-cephem-4-carboxylic acid, 7-[D(—)-α-(3,5-dioxo-1-piperazinocarbonylamino)-phenylacetamido]-3-[5-(1-methyl-1,2,3,4-tetrazolyl)-thiomethyl]-Δ³-cephem-4-carboxylic acid, 7-[D(—)-α-(4-acetyl-2,5-dioxo-1-piperazinocarbonylamino)phenylacetamido]-3-[5-(1-methyl-1,2,3,4-tetrazolyl)-thiomethyl]-Δ³-cephem-4-carboxylic acid, methoxymethyl 7-[D(—)-α-(4-methyl-2,3-dioxo-1-piperazinocarbonylamino)phenylacetamido]-3-methyl-Δ³-cephem-4-carboxylate, etc.

The susceptible test of typical compounds among the compounds of the present invention are shown below.

(1) The minimum inhibitory concentrations (MIC) of the compounds against different standard strains are shown in Tables 3 and 4.

The minimum inhibitory concentrations (MIC) was determined by the plate method disclosed in "Chemotherapy" (Japan), Vol. 16, (1968), pages 98 – 99. The culture medium used was a Heart infusion agar (pH 7.4). The number of the cells per plate used in the inoculum as $10^4$ ($10^6$ cells/ml).

Table 3

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| (Control) | (Sodium Ampicillin) | <1.57 | <1.57 | >200 | 50 | >200 |
| (Control) | (Sodium Carbenicillin) | <1.57 | <1.57 | 50 | >200 | <1.57 |
| (Control) | (Sodium Sulbenicillin) | 3.13 | 1.57 | 50 | >200 | 0.79 |
| 1 | | <1.57 | <1.57 | 25 | 12.5 | 3.13 |
| 2 | | <1.57 | <1.57 | 50 | 12.5 | 6.25 |
| 3 | | <1.57 | <1.57 | 100 | 3.13 | 3.13 |

Table 3-continued

| Compound No. | Compound | Staphylo- coccus aureus 209p | Escherichia coli NIHJ | Pseudomonas aeruginosa I.F.O. | Klebsiella pneumoniae | Proteus vulgaris 3027 |
|---|---|---|---|---|---|---|
| 4 | [structure] | <1.57 | <1.57 | 25 | 12.5 | 3.13 |
| 5 | [structure] | <1.57 | <1.57 | 25 | 12.5 | <1.57 |
| 6 | [structure] | 3.13 | 3.13 | 50 | 6.25 | 6.25 |
| 7 | [structure] | <1.57 | <1.57 | 200 | 12.5 | 6.25 |
| 8 | [structure] | <1.57 | <1.57 | 100 | 6.25 | 3.13 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 9 | 4-CH₃-C₆H₄-CON-piperidone-NCONHCH(C₆H₅)CONH-penicillin-COONa | <1.57 | 3.13 | 100 | 3.13 | 3.13 |
| 10 | 2,4-Cl₂-C₆H₃-CON-piperidone-NCONHCH(C₆H₅)CONH-penicillin-COONa | <1.57 | <1.57 | 100 | 6.25 | 3.13 |
| 11 | CH₃CONHCON-piperidone-NCONHCH(C₆H₅)CONH-penicillin-COONa | <1.57 | <1.57 | 50 | 50 | 6.25 |
| 12 | CH₃CH₂OCON-piperidone-NCONHCH(C₆H₅)CONH-penicillin-COONa | <1.57 | 3.13 | 50 | 6.25 | 12.5 |
| 13 | CH₃(CH₂)₂CH₂N-piperidone-NCONHCH(C₆H₅)CONH-penicillin-COONa | <1.57 | <1.57 | 25 | <1.57 | <1.57 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 14 | CH₃(CH₂)₂CH₂N–(piperidinone)–NCONHCHCONH–(penicillin)–C₆H₅, COONa | <1.57 | <1.57 | 25 | 3.13 | <1.57 |
| 15 | CH₃(CH₂)₂CH₂N–(methylpiperidinone)–NCONHCHCONH–(penicillin)–C₆H₅, COONa | <1.57 | 3.13 | 50 | 6.25 | 6.25 |
| 16 | CH₃(CH₂)₆CH₂N–(piperidinone)–NCONHCHCONH–(penicillin)–C₆H₅, COONa | <1.57 | <1.57 | 12.5 | 1.57 | <1.57 |
| 17 | CH₃N–(piperidinone)–NCONHCHCONH–(penicillin)–C₆H₅, COONa | <1.57 | <1.57 | 12.5 | 50 | 6.25 |
| 18 | CH₃(CH₂)₂CH₂N–(piperidinone)–NCONHCHCONH–(penicillin)–C₆H₅, COONa | <1.57 | <1.57 | 12.5 | 25 | 3.13 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 19 | CH₃CH₂N-[piperidone]-NCONHCHCONH-[penicillin]-Ph, COONa | <1.57 | <1.57 | 12.5 | 50 | 3.13 |
| 20 | (CH₃)₂CHN-[piperidone]-NCONHCHCONH-[penicillin]-Ph, COONa | 3.13 | <1.57 | 12.5 | 25 | 3.13 |
| 21 | (CH₃)₂CHCH₂CH₂N-[piperidone]-NCONHCHCONH-[penicillin]-Ph, COONa | <0.79 | 1.57 | 25 | 25 | 3.13 |
| 22 | CH₃(CH₂)₂CH₂N-[methylpiperidone]-NCONHCHCONH-[penicillin]-Ph, COONa | <1.57 | <1.57 | 50 | 12.5 | 6.25 |
| 23 | C₆H₅CH₂N-[piperidone]-NCONHCHCONH-[penicillin]-Ph, COONa | <1.57 | <1.57 | 25 | 6.25 | 3.13 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 24 | HOCH₂CH₂N—[ring]—NCONHCHCONH—[β-lactam]—S—C(CH₃)₂—COONa / phenyl | 3.13 | <1.57 | 50 | 50 | 25 |
| 25 | CH₂=CHCH₂N—[ring]—NCONHCHCONH—[β-lactam]—S—C(CH₃)₂—COONa / phenyl | <1.57 | <1.57 | 25 | 50 | 3.13 |
| 26 | CH₂=CCH₂N(CH₃)—[ring]—NCONHCHCONH—[β-lactam]—S—C(CH₃)₂—COONa / phenyl | <1.57 | <1.57 | 25 | 25 | 12.5 |
| 27 | CH₂=CCH₂N(CH₃)—[ring]—NCONHCHCONH—[β-lactam]—S—C(CH₃)₂—COONa / phenyl | <1.57 | <1.57 | 25 | 25 | 3.13 |
| 28 | CH₃CH=CHCH₂N—[ring]—NCONHCHCONH—[β-lactam]—S—C(CH₃)₂—COONa / phenyl (trans-) | <1.57 | <1.57 | 25 | 25 | 3.13 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 29 | CH₃(CH₂)₄CH₂N-...-NCONHCHCONH-...-phenyl, S, CH₃, CH₃, COONa | 3.13 | <1.57 | 12.5 | 3.13 | 3.13 |
| 30 | CH₃(CH₂)₆CH₂N-...-NCONHCHCONH-...-phenyl, S, CH₃, CH₃, COONa | <1.57 | <1.57 | 25 | 6.25 | 3.13 |
| 31 | CH₃(CH₂)₁₀CH₂N-...-NCONHCHCONH-...-phenyl, S, CH₃, CH₃, COONa | <1.57 | <1.57 | 12.5 | 6.25 | <1.57 |
| 32 | cyclopentyl-NH-...-NCONHCHCONH-...-phenyl, S, CH₃, CH₃, COONa | <1.57 | <1.57 | 12.5 | 12.5 | 6.25 |
| 33 | phenyl-NHCON-...-NCONHCHCONH-...-phenyl, S, CH₃, CH₃, COONa | <1.57 | <1.57 | 50 | 6.25 | 3.13 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 34 | | 1.57 | 3.13 | 100 | 50 | 50 |
| 35 | | 1.57 | 6.25 | 100 | 25 | 25 |
| 36 | | <1.57 | <1.57 | 6.25 | <1.57 | <1.57 |
| 37 | | <1.57 | <1.57 | 6.25 | 6.25 | <1.57 |
| 38 | | 0.4 | <0.1 | 6.25 | 3.13 | 0.4 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 39 | CH₃(CH₂)₂CH₂N-... (penicillin derivative, COONa) | 0.4 | <0.1 | 6.25 | 1.57 | 0.4 |
| 40 | (CH₃)₂CHN-... | 0.4 | <0.1 | 6.25 | 3.13 | 0.4 |
| 41 | CH₃COOCH₂CH₂N-... | <1.57 | <1.57 | 25 | 6.25 | <1.57 |
| 42 | CH₂=CHCH₂N-... | 1.57 | <1.57 | 12.5 | 6.25 | <1.57 |
| 43 | C₆H₅N-... | <1.57 | <1.57 | 6.25 | 1.57 | <1.57 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 44 | ClCH$_2$CH$_2$N-[structure with NCONHCHCONH-phenyl, penicillin nucleus with S, CH$_3$, CH$_3$, COONa] | <1.57 | <1.57 | 6.25 | <1.57 | <1.57 |
| 45 | CH$_3$(CH$_2$)$_3$CH$_2$N-[structure with NCONHCHCONH-phenyl, penicillin nucleus] | 0.79 | <0.1 | 12.5 | 0.79 | 0.4 |
| 46 | CH$_3$(CH$_2$)$_4$CH$_2$N-[structure with NCONHCHCONH-phenyl, penicillin nucleus] | 0.2 | <0.1 | 6.25 | 0.4 | 0.4 |
| 47 | CH$_3$(CH$_2$)$_6$CH$_2$N-[structure with NCONHCHCONH-phenyl, penicillin nucleus] | <1.57 | <1.57 | 6.25 | <1.57 | <1.57 |
| 48 | CH$_3$N-[structure with NCONHCHCONH-phenyl-OH, penicillin nucleus] | 0.4 | <0.4 | 6.25 | 25 | <0.4 |

Table 3-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 49 | (structure) | <0.4 | 0.79 | 12.5 | 12.5 | 1.57 |
| 50 | (structure) | <0.79 | <0.79 | 6.25 | 6.25 | <0.79 |
| 51 | (structure) | <0.4 | <0.4 | 12.5 | <0.4 | <0.4 |
| 52 | (structure) | 0.79 | 0.79 | 25 | 25 | 1.57 |
| 53 | (structure) | 0.79 | <0.4 | 6.25 | 25 | 0.79 |

Table 3-continued

| Compound No. | Compound | Staphylo- coccus aureus 209p | Escherichia coli NIHJ | Pseudomonas aeruginosa I.F.O. | Klebsiella pneumoniae | Proteus vulgaris 3027 |
|---|---|---|---|---|---|---|
| 54 | | 0.79 | 0.4 | 12.5 | 0.79 | 0.79 |
| 55 | | 0.79 | 0.4 | 6.25 | 25 | 0.79 |
| 56 | | <0.4 | <0.4 | 12.5 | 1.57 | 0.79 |
| 57 | | <0.79 | <0.79 | 12.5 | 12.5 | 3.13 |
| 58 | | <1.57 | <1.57 | 12.5 | 25 | 3.13 |

Table 3-continued
| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 59 |  | <1.57 | <1.57 | 25 | 200 | 3.13 |
(Note) Sodium Carbenicillin and Sodium Sulbenicillin are regarded as preferable drugs at the level of this technical field, and hence are described for reference.

Table 4
| Compound No. | Compound | | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|---|
| (Control) | 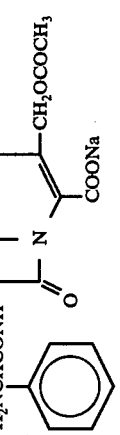 | (Sodium Cephaloglycin) | <1.57 | <1.57 | >200 | 100 | <1.57 |
| | 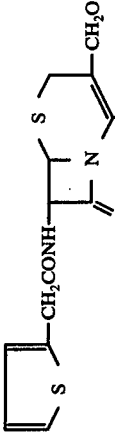 | (Sodium Cephalothin) | <1.57 | <1.57 | >200 | 100 | <1.57 |
| | 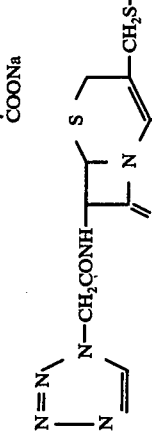 | (Sodium Cephazolin) | <1.57 | <1.57 | >200 | 200 | 1.57 |
| | 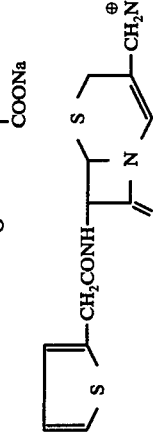 | (Cephaloridine) | <1.57 | >3.13 | 200 | 200 | 3.13 |
| 60 | 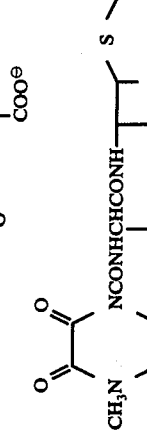 | | 0.79 | <0.1 | 25 | 3.13 | 3.13 |
| 61 | 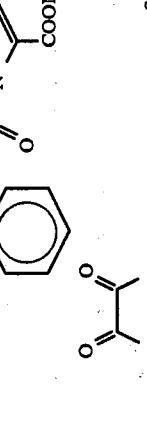 | | <0.79 | <0.79 | 25 | 3.13 | 3.13 |

Table 4-continued

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| 62 | (structure) | 0.79 | <0.1 | 50 | 1.57 | 3.13 |
| 63 | (structure) | <0.79 | <0.79 | 25 | <0.79 | 1.57 |
| 64 | (structure) | 0.79 | <0.1 | 25 | 1.57 | 3.13 |
| 65 | (structure) | 3.13 | 0.79 | 25 | 3.13 | 3.13 |

Table 4-continued

| Compound No. | Compound | Staphylo- coccus aureus 209p | Escherichia coli NIHJ | Pseudomonas aeruginosa I.F.O | Klebsiella pneumoniae | Proteus vulgaris 3027 |
|---|---|---|---|---|---|---|
| 66 | | <0.79 | <0.79 | 25 | 0.79 | <1.57 |
| 67 | | 6.25 | <0.79 | 100 | 3.13 | 12.5 |
| 68 | | 1.57 | <0.79 | 12.5 | <0.79 | 1.57 |
| 69 | | <0.79 | <0.79 | 12.5 | <0.4 | <0.79 |

Table 4-continued

| Compound No. | Compound | Staphylo-coccus aureus 209p | Escherichia coli NIHJ | Pseudomonas aeruginosa I.F.O | Klebsiella pneumoniae | Proteus vulgaris 3027 |
|---|---|---|---|---|---|---|
| 70 | (structure with NCONHCHCONH, phenyl, CH₃CH₂N, CH₂S-pyridine N→O, COONa) | <0.79 | 1.57 | 100 | 1.56 | <0.79 |
| 71 | (structure with NCONHCHCONH, phenyl, CH₃N, CH₂S-methylthiadiazole, COONa) | <0.79 | <0.79 | 50 | 1.56 | <0.79 |

(Note)
Sodium Cephalothin, Sodium Cephazolin and Cephaloridine are regarded as preferable drugs at the level of this technical field, and hence are set forth for reference.

(2) The minimum inhibitory concentrations (MIC) of the compounds against clinical isolates of bacteria are shown in Tables 5 and 6.

MIC was determined in the same manner as in the preceding paragraph (1).

Table 5-1

| Compound | Staphylococcus aureus | | | | | | | | | |
|---|---|---|---|---|---|---|---|---|---|---|
| | MS 8619 | MS 8588 | MS 8713 | MS 8596 | MS 8684 | F-1 | F-2 | F-3 | F-4 | F-5 |
| Control | | | | | | | | | | |
| Sodium Ampicillin | <0.4 | 6.25 | 3.13 | 1.56 | 1.56 | 12.5 | 0.79 | | 12.5 | 50 |
| Sodium Carbenicillin | 0.79 | 6.25 | 6.25 | 6.25 | 6.25 | 6.25 | 3.13 | 3.13 | 12.5 | >200 |
| Sodium Sulbenicillin | 3.13 | 3.13 | 3.13 | 3.13 | 3.13 | 6.25 | 3.13 | 6.25 | 6.25 | >200 |
| Compound No. 1 | 1.57 | 6.25 | 3.13 | 3.13 | 3.13 | 12.5 | 3.13 | | 6.25 | >200 |
| Compound No. 13 | 0.79 | 3.13 | 3.13 | 3.13 | 3.13 | 12.5 | 1.57 | | 6.25 | 200 |
| Compound No. 14 | 0.79 | 3.13 | 3.13 | 3.13 | 3.13 | 12.5 | 1.57 | | 6.25 | 200 |
| Compound No. 16 | <0.4 | 3.13 | 3.13 | 3.13 | 3.13 | 6.25 | 0.79 | | 6.25 | 100 |
| Compound No. 30 | <0.4 | 1.57 | 1.57 | 1.57 | 1.57 | 3.13 | 0.79 | 0.79 | 3.13 | 100 |
| Compound No. 36 | 0.79 | 3.13 | 6.25 | 3.13 | 3.13 | 12.5 | 3.13 | 1.57 | 6.25 | >200 |
| Compound No. 37 | 0.79 | 3.13 | 12.5 | 3.13 | 3.13 | 12.5 | 1.57 | 3.13 | 6.25 | >200 |
| Compound No. 38 | 0.79 | 3.13 | 6.25 | 3.13 | 3.13 | 6.25 | 1.57 | 0.79 | 6.25 | >200 |
| Compound No. 39 | 0.79 | 1.57 | 3.13 | 1.57 | 3.13 | 6.25 | 1.57 | 1.57 | 6.25 | >200 |
| Compound No. 40 | 0.79 | 3.13 | 12.5 | 3.13 | 3.13 | 6.25 | 3.13 | 0.79 | 6.25 | >200 |
| Compound No. 45 | 0.79 | 3.13 | 6.25 | 3.13 | 3.13 | 6.25 | 1.57 | 1.57 | 6.25 | >200 |
| Compound No. 46 | <0.4 | 1.57 | 6.25 | 3.13 | 1.57 | 6.25 | 1.57 | 0.79 | 6.25 | >200 |
| Compound No. 47 | <0.4 | 3.13 | 6.25 | 3.13 | 3.13 | 6.25 | 1.57 | 1.57 | 12.5 | >200 |

Table 5-2

| Compound | Escherichia coli | | | | | | | | |
|---|---|---|---|---|---|---|---|---|---|
| | GN 3481 | GN 3435 | GN 3452 | GN 3465 | GN 3611 | K-1 | K-2 | K-3 | K-4 |
| Control | | | | | | | | | |
| Sodium Ampicillin | 6.25 | 3.13 | 6.25 | | >200 | 6.25 | 6.25 | >200 | 12.5 |
| Sodium Carbenicillin | 6.25 | 6.25 | 12.5 | >200 | >200 | 6.25 | 6.25 | >200 | 12.5 |
| Sodium Sulbenicillin | 12.5 | 6.25 | 12.5 | >200 | >200 | 6.25 | 12.5 | >200 | 6.25 |
| Compound No. 1 | 12.5 | 6.25 | 12.5 | 200 | | 6.25 | 25 | >200 | 12.5 |
| Compound No. 13 | 6.25 | 3.13 | 3.13 | 25 | | 3.13 | 6.25 | 100 | 6.25 |
| Compound No. 14 | 6.25 | 6.25 | 6.25 | 50 | | 3.13 | 12.5 | 200 | 6.25 |
| Compound No. 16 | 3.13 | 1.57 | 1.57 | 12.5 | | 1.57 | 3.13 | 50 | 3.13 |
| Compound No. 30 | 25 | 12.5 | 25 | 50 | >200 | 12.5 | 25 | >200 | 12.5 |
| Compound No. 36 | 3.13 | 1.57 | 3.13 | 100 | >200 | 3.13 | 3.13 | >200 | 1.57 |
| Compound No. 37 | 6.25 | 3.13 | 12.5 | 200 | >200 | 12.5 | 6.25 | >200 | 3.13 |
| Compound No. 38 | 3.13 | 0.79 | 3.13 | 50 | >200 | 3.13 | 3.13 | >200 | 0.79 |
| Compound No. 39 | 1.57 | 0.79 | 0.79 | 25 | >200 | 1.57 | 1.57 | >200 | 0.79 |
| Compound No. 40 | 1.57 | 0.79 | 1.57 | 50 | >200 | 1.57 | 3.13 | >200 | 0.79 |
| Compound No. 45 | 1.57 | 0.79 | 1.57 | 25 | >200 | 0.79 | 1.57 | 200 | 0.79 |
| Compound No. 46 | 3.13 | <0.4 | 0.79 | 6.25 | >200 | 0.79 | 0.79 | 50 | <0.4 |
| Compound No. 47 | 1.57 | 0.79 | 1.57 | 6.25 | >200 | 1.57 | 1.57 | 100 | 0.79 |

Table 5-3

| Compound | Pseudomonas aeruginosa | | | | | | | | | |
|---|---|---|---|---|---|---|---|---|---|---|
| | GN 1035 | GN 376 | GN 82 | GN 221 | GN 1091 | GN 2565 | GN 2987 | GN 163 | GN 244 | GN 383 |
| Control | | | | | | | | | | |
| Sodium Ampicillin | >200 | >200 | >200 | >200 | >200 | >200 | >200 | >200 | >200 | >200 |
| Sodium Carbenicillin | >200 | 50 | 100 | 25 | 100 | 200 | 50 | 50 | 50 | 30 |
| Sodium Sulbenicillin | 100 | 50 | 50 | 25 | 50 | 100 | 25 | 50 | 50 | 50 |
| Compound No. 1 | 100 | 25 | 25 | 25 | 25 | 50 | 25 | 25 | 25 | 50 |
| Compound No. 13 | 50 | 50 | 50 | 50 | 25 | 50 | 12.5 | 25 | 50 | 50 |
| Compound No. 14 | 50 | 50 | 25 | 25 | 25 | 50 | 12.5 | 25 | 50 | 50 |
| Compound No. 16 | 25 | 25 | 6.25 | 25 | 12.5 | 12.5 | 3.13 | 12.5 | 12.5 | 25 |
| Compound No. 19 | 100 | 12.5 | 12.5 | 12.5 | 12.5 | 50 | 12.5 | 12.5 | 25 | 12.5 |
| Compound No. 30 | 50 | 50 | 25 | 50 | 25 | 50 | 12.5 | 25 | 50 | 50 |
| Compound No. 36 | 25 | 6.25 | 6.25 | 3.13 | 6.25 | 25 | 12.5 | 6.25 | 12.5 | 6.25 |
| Compound No. 37 | 50 | 12.5 | 6.25 | 6.25 | 12.5 | 25 | 25 | 12.5 | 50 | 25 |
| Compound No. 38 | 12.5 | 3.13 | 3.13 | 6.25 | 3.13 | 12.5 | 6.25 | 3.13 | 6.25 | 6.25 |
| Compound No. 39 | 12.5 | 6.25 | 3.13 | 3.13 | 3.13 | 12.5 | 3.13 | 3.13 | 6.25 | 6.25 |
| Compound No. 40 | 25 | 3.13 | 6.25 | 6.25 | 6.25 | 12.5 | 3.13 | 6.25 | 6.25 | 6.25 |
| Compound No. 45 | 50 | 25 | 12.5 | 3.13 | 12.5 | 25 | 12.5 | 12.5 | 25 | 25 |
| Compound No. 46 | 50 | 25 | 6.25 | 12.5 | 12.5 | 12.5 | 6.25 | 6.25 | 12.5 | 25 |
| Compound No. 47 | 25 | 50 | 12.5 | 25 | 12.5 | 25 | 12.5 | 12.5 | 25 | 25 |

Table 5-4

| Compound | Pseudomonas aeruginosa | | | | Klebsiella pneumoniae | | | |
|---|---|---|---|---|---|---|---|---|
| | S-1 | S-2 | S-3 | S-4 | GN 4117 | GN 4081 | GN 3850 | GN 917 |
| Control | | | | | | | | |
| Sodium Ampicillin | >200 | >200 | >200 | >200 | >200 | >200 | 50 | 25 |
| Sodium Carbenicillin | 200 | 200 | 200 | 200 | >200 | >200 | | >200 |
| Sodium Sulbenicillin | 100 | 100 | 100 | 100 | >200 | >200 | >200 | >200 |
| Compound No. 1 | 50 | 100 | 50 | 50 | 200 | >200 | 25 | 25 |
| Compound No. 13 | 50 | 50 | 100 | 50 | 25 | 25 | 6.25 | 12.5 |
| Compound No. 14 | 50 | 50 | 100 | 50 | 50 | 50 | 12.5 | 25 |
| Compound No. 16 | 12.5 | 25 | 50 | 25 | 25 | 25 | 3.13 | 12.5 |
| Compound No. 19 | 50 | 50 | 50 | 50 | >200 | >200 | 100 | 50 |
| Compound No. 30 | 50 | 50 | 100 | 50 | 100 | 100 | 25 | 25 |
| Compound No. 36 | 50 | 12.5 | 25 | 50 | 100 | 100 | 12.5 | 6.25 |
| Compound No. 37 | 200 | 25 | 50 | 100 | 100 | 200 | 25 | 12.5 |
| Compound No. 38 | 12.5 | 12.5 | 12.5 | 12.5 | 50 | 50 | 6.25 | 3.13 |
| Compound No. 39 | 12.5 | 12.5 | 25 | 12.5 | 25 | 25 | 3.13 | 1.57 |
| Compound No. 40 | 12.5 | 25 | 25 | 12.5 | 50 | 100 | 12.5 | 6.25 |
| Compound No. 45 | 25 | 25 | 50 | 25 | 25 | 25 | 3.13 | 1.57 |
| Compound No. 46 | 50 | 50 | 50 | 50 | 12.5 | 12.5 | 1.57 | 0.79 |
| Compound No. 47 | 50 | 50 | 50 | 50 | 12.5 | 12.5 | 3.13 | 1.57 |

Table 5-5

| Compound | Shigella sonnei | | Shigella flexneri | | Salmonella typhi | | Salmonella typhi-murium | |
|---|---|---|---|---|---|---|---|---|
| | JS 11755 | JS 11232 | JS 11215 | JS 11839 | SL 2169 | SL 819 | SL 2136 | SL 858 |
| Control | | | | | | | | |
| Sodium Ampicillin | 6.25 | >200 | | 1.57 | 0.78 | 1.56 | >200 | 3.13 |
| Sodium Carbenicillum | 12.5 | >200 | >200 | 12.5 | 3.13 | 6.25 | >200 | 12.5 |
| Sodium Sulbenicillum | >200 | >200 | >200 | 12.5 | 1.57 | 6.25 | >200 | 25 |
| Compound No. 1 | 12.5 | >200 | 100 | 3.13 | 6.25 | 6.25 | >200 | 12.5 |
| Compound No. 13 | 3.13 | 12.5 | 12.5 | 1.57 | 3.13 | 6.25 | 200 | 0.79 |
| Compound No. 14 | 6.25 | 25 | 25 | 3.13 | 3.13 | 6.25 | 200 | 1.57 |
| Compound No. 16 | 1.57 | 6.25 | 6.25 | 0.79 | 1.57 | 3.13 | 100 | 1.57 |
| Compound No. 36 | 3.13 | 50 | 100 | 3.13 | 1.57 | 1.57 | >200 | 6.25 |
| Compound No. 37 | 6.25 | 100 | >200 | 6.25 | 3.13 | 6.25 | >200 | 12.5 |
| Compound No. 38 | 3.13 | 50 | 25 | 1.57 | 0.79 | 1.57 | 200 | 3.13 |
| Compound No. 39 | 1.57 | 25 | 25 | 0.79 | 0.79 | 0.79 | 100 | 0.79 |
| Compound No. 40 | 3.13 | 50 | 50 | 3.13 | 1.57 | 1.57 | >200 | 6.25 |
| Compound No. 45 | 1.57 | 25 | 25 | 1.57 | 0.79 | 1.57 | 200 | 0.79 |
| Compound No. 46 | 0.79 | 12.5 | 6.25 | 0.79 | 0.79 | 1.57 | 50 | <0.4 |
| Compound No. 47 | 0.79 | 6.25 | 6.25 | 1.57 | 1.57 | 3.13 | 50 | <0.4 |

Table 5-6

| Compound | Proteus | | | |
|---|---|---|---|---|
| | mirabilis | morganii | vulgaris | rettgeri |
| Control | | | | |
| Sodium Ampicillin | <1.57 | <1.57 | <1.5 | 200 |
| Sodium Carbenicillin | 0.8 | 0.4 | 0.8 | >200 |
| Sodium Sulbenicillin | 0.79 | <0.4 | <0.4 | >200 |
| Compound No. 16 | 1.56 | 1.56 | 0.8 | 6.25 |
| Compound No. 30 | 3.13 | 3.13 | 3.13 | 12.5 |
| Compound No. 36 | <0.4 | <0.4 | <0.4 | 12.5 |
| Compound No. 37 | 0.79 | 0.79 | <0.4 | 25 |
| Compound No. 38 | <0.4 | <0.4 | <0.4 | 12.5 |
| Compound No. 39 | <0.4 | <0.4 | <0.4 | 6.25 |
| Compound No. 40 | <0.4 | 0.79 | <0.4 | 6.25 |
| Compound No. 45 | <0.4 | 0.79 | <0.4 | 6.25 |
| Compound No. 46 | <0.4 | <0.4 | <0.4 | 3.13 |
| Compound No. 47 | <0.4 | <0.4 | <0.4 | 0.79 |

Table 6-1

| Compound | Staphylococcus aureus | | | | | | | | | |
|---|---|---|---|---|---|---|---|---|---|---|
| | MS 8619 | MS 8588 | MS 8713 | MS 8596 | MS 8684 | F-1 | F-2 | F-3 | F-4 | F-5 |
| Control | | | | | | | | | | |
| Sodium Cephaloglycin | 1.56 | 3.13 | 3.13 | 1.56 | 1.56 | 3.13 | 1.56 | 1.56 | 3.13 | 25 |
| Sodium Cephalothin | <0.4 | <0.4 | <0.4 | <0.4 | <0.4 | <0.4 | <0.4 | <0.4 | <0.4 | 1.56 |
| Sodium Cephazolin | <0.4 | <0.4 | <0.4 | <0.4 | <0.4 | 0.78 | <0.4 | <0.4 | <0.4 | 0.78 |
| Cephalorizine | <0.4 | <0.4 | <0.4 | <0.4 | <0.4 | <0.4 | <0.4 | <0.4 | <0.4 | 0.78 |
| Compound No. 60 | 0.78 | 1.56 | 0.78 | 0.78 | 1.56 | 3.13 | 0.78 | 1.56 | 1.56 | 50 |
| Compound No. 61 | 1.56 | 1.56 | 1.56 | 1.56 | 1.56 | 3.13 | 1.56 | 1.56 | 3.13 | 50 |
| Compound No. 62 | 0.78 | 1.56 | 1.56 | 0.78 | 1.56 | 3.13 | 0.78 | 1.56 | 1.56 | 12.5 |
| Compound No. 63 | 0.78 | 1.56 | 1.56 | 1.56 | 1.56 | 3.13 | 0.78 | 1.56 | 1.56 | 12.5 |
| Compound No. 68 | 0.78 | 1.56 | 3.13 | 1.56 | 1.56 | 1.56 | 1.56 | 0.78 | 6.25 | 0.78 |
| Compound No. 69 | 0.78 | 1.56 | 1.56 | 1.56 | 1.56 | 3.13 | 1.56 | 0.78 | 3.13 | 0.78 |

Table 6-2

| | Compound | *Escherichia coli* | | | | | | | | |
|---|---|---|---|---|---|---|---|---|---|---|
| | | GN 3481 | GN 3435 | GN 3452 | GN 3465 | GN 3611 | K-1 | K-2 | K-3 | K-4 |
| Control | Sodium Cephaloglycin | 3.13 | 1.56 | 3.13 | 12.5 | 25 | 1.56 | 1.56 | 25 | 12.5 |
| | Sodium Cephalothin | 12.5 | 6.25 | 12.5 | 25 | 50 | 6.25 | 6.25 | 100 | 25 |
| | Sodium Cephazolin | 1.56 | 1.56 | 1.56 | 6.25 | 25 | 1.56 | 1.56 | >200 | 3.13 |
| | Cephalorizine | 3.13 | 3.13 | 3.13 | 50 | 100 | 3.13 | 3.13 | 200 | 6.25 |
| | Compound No. 60 | 6.25 | 6.25 | 12.5 | 100 | >200 | 6.25 | 12.5 | 200 | 25 |
| | Compound No. 61 | 3.13 | 3.13 | 6.25 | 50 | 200 | 3.13 | 6.25 | 100 | 6.25 |
| | Compound No. 62 | 6.25 | 6.25 | 6.25 | 25 | 200 | 6.25 | 12.5 | 200 | 12.5 |
| | Compound No. 63 | 3.13 | 3.13 | 12.5 | 25 | 100 | 3.13 | 6.25 | 50 | 6.25 |

Table 6-3

| | Compound | *Pseudomonas aeruginosa* | | | | | | | | |
|---|---|---|---|---|---|---|---|---|---|---|
| | | GN 1035 | GN 376 | GN 82 | GN 221 | GN 1091 | GN 2565 | GN 2987 | GN 163 | GN 244 | GN 383 |
| Control | Sodium Cephaloglycin | >200 | >200 | >200 | >200 | >200 | >200 | >200 | >200 | >200 | >200 |
| | Sodium Cephalothin | >200 | >200 | >200 | >200 | >200 | >200 | >200 | >200 | >200 | >200 |
| | Sodium Cephazolin | >200 | >200 | >200 | >200 | >200 | >200 | >200 | >200 | >200 | >200 |
| | Cephalorizine | >200 | >200 | >200 | >200 | >200 | >200 | >200 | >200 | >200 | >200 |
| | Compound No. 60 | 200 | 50 | 50 | 12.5 | 50 | 100 | 50 | 50 | 50 | 50 |
| | Compound No. 61 | 100 | 12.5 | 25 | 6.25 | 25 | 50 | 25 | 25 | 25 | 12.5 |
| | Compound No. 62 | 200 | 100 | 100 | 50 | 100 | 100 | 50 | 50 | 100 | 100 |
| | Compound No. 63 | 100 | 50 | 50 | 25 | 50 | 50 | 25 | 25 | 50 | 25 |
| | Compound No. 68 | 50 | 12.5 | 6.25 | 3.13 | 12.5 | 50 | 12.5 | 12.5 | 25 | 12.5 |
| | Compound No. 69 | 50 | 12.5 | 12.5 | 6.25 | 12.5 | 50 | 12.5 | 12.5 | 25 | 25 |

Table 6-4

| | Compound | *Pseudomonas aeruginosa* | | | | *Klebsiella pneumoniae* | | |
|---|---|---|---|---|---|---|---|---|
| | | S-1 | S-2 | S-3 | S-4 | GN 4117 | GN 4081 | GN 917 |
| Control | Sodium Cephaloglycin | >200 | >200 | >200 | >200 | 3.13 | 3.13 | 1.56 |
| | Sodium Cephalothin | >200 | >200 | >200 | >200 | 6.25 | 12.5 | 3.13 |
| | Sodium Cephazolin | >200 | >200 | >200 | >200 | 3.13 | 3.13 | 1.56 |
| | Cephalorizine | >200 | >200 | >200 | >200 | 12.5 | 12.5 | 3.13 |
| | Compound No. 60 | 200 | 100 | 100 | 100 | 25 | 25 | 6.25 |
| | Compound No. 61 | 50 | 50 | 50 | 50 | 12.5 | 12.5 | 6.25 |
| | Compound No. 62 | 200 | 200 | 200 | 200 | 25 | 12.5 | 6.25 |
| | Compound No. 63 | 100 | 100 | 100 | 100 | 6.25 | 6.25 | 3.13 |
| | Compound No. 68 | 25 | 25 | 25 | 25 | — | — | 1.56 |
| | Compound No. 69 | 25 | 25 | 50 | 50 | — | — | 0.78 |

Table 6-5

| Compound | *Proteus* | | | |
|---|---|---|---|---|
| | mirabilis | morganii | vulgaris | rettgeri |
| Sodium Cephaloglycin | 3.13 | 1.56 | 50 | 50 |
| Compound No. 60 | 3.13 | 3.13 | 1.56 | 6.25 |
| " 61 | 1.56 | 1.56 | 0.8 | 3.13 |
| " 62 | 6.25 | 3.13 | 3.13 | 6.25 |
| " 63 | 3.13 | 3.13 | 1.56 | 3.13 |

(3) Resistant activity against β-lactamase, *Pseudomonas aerugionan* GN 238:

The resistant activity of each compound against β-lactamase was measured in the manner described below.

β-Lactamase was prepared from *Pseudomonas aeruginosa* GN 238. This microorganism was cultured in 100 ml of a medium containing 2 g of yeast extract, 10 g of polypeptone, 2 g of glucose, 7 g of disodium hydrogen phosphate, 2 g of potassium dihydrogen phosphate, 1.2 g of ammonium sulfate and 0.4 g of magnesium sulfate, per liter, in a 500-ml Erlenmeyer flask for 6 hrs. at 37° C with shaking. The resulting cells were collected by centrifugation (5,000 r.p.m. × 10 min.), washed three times with 0.1 M phosphate buffer (pH 7.0). Subsequently, the cells were subjected to sonication (20 KH$_z$, 20 min.) and then centrifuged at 15,000 r.p.m. for 60 min. By using the supernatant of enzyme fluid, the resistance of each compound against β-lactamase was determined by the iodometric assay method. The results obtained were as set forth in Table 7. Each numeral shown in Table 7 is a relative activity value calculated by assuming as 100 the activity of the control Potassium Penicillin G.

Table 7

| | Comparison of resistant activity against β-lactamase | |
|---|---|---|
| | Compound | Relative activity (%) |
| Control | Potassium Penicillin G | 100. |
| | Sodium Ampicillin | 115 |
| | Sodium carbenicillin | 116 |
| | Sodium Sulbenicillin | 50 |
| Compound No. | 30 | 3 |
| " | 36 | 14 |
| " | 37 | 15 |
| " | 38 | 15 |
| " | 39 | 15 |
| " | 40 | 15 |
| " | 45 | 16 |
| " | 46 | 12 |
| " | 47 | 1 |

From Tables 3 to 6, it is understood that the compounds of the present invention have a broader antibacterial spectrum and more excellent antibacterial activity against not only *Pseudomonas aeruginosa, Klebsiella pneumonia,* and *Proteus* species but also many drug-resistant bacteria than the control ampicillin and cephaloglycin, i.e. compounds having an amino group at the α-position of the acyl group. It is also understood from Table 7 that the compounds of the present invention are far higher in resistance to β-lactamase than the control drugs.

As is clear from the above results, the compounds represented by the formula (Ie), among the compounds of the present invention, show prominent effects, and particularly preferable compounds are those of the formula (Ie), in which A represents a hydrogen atom, or an unsubstituted or substituted alkyl, alkenyl, aryl or aralkyl group; and $R^2$ and $R^3$ represent individually a hydrogen atom or an alkyl group.

The present penicillins and cephalosporins have generally low toxicity. For example, 6-[D(−)-α-(4-methyl-2,3-dioxo-1-piperazinocarbonylamino)-phenylacetamido]penicillanic acid and 6-[D(−)-α-(4-ethyl-2,3-dioxo-1-piperazinocarbonylamino)-phenylacetamido]penicillanic acid have LD$_{50}$ (i.v. in mouse having a weight of 19 ± g) greater than 5 g/kg.

The compounds of formula (I) of the present invention may be administered not only in the form of free acids but also in the form of non-toxic salts or physiologically acceptable esters. Further, the compounds, which are in the form of physiologically unacceptable esters, are ordinarily put into uses after bringing them to the form of free acids or non-toxic salts by removing the ester-forming group according to a conventional procedure known in this technical field.

The compounds of the present invention can be administered to humans and animals after formulating them into a physiological form such as tablet, capsule, syrup, injection or the like which is usually adopted in the case of penicillin and cephalosporin type drugs.

Procedures for producing the compounds of the present invention are shown below with reference to examples.

EXAMPLE 1

(1) To a mixture comprising 2.5 g of 1-acetyl-3-oxopiperazine, 3.45 g of triethylamine and 20 ml of anhydrous dioxane was added a solution of 3.71 g of trimethylchlorosilane in 10 ml of anhydrous dioxane. The resulting mixture was refluxed for 17 hours and cooled to deposit triethylamine hydrochloride, which was then removed by filtration. The filtrate was dropped at −40° to −30° C into a solution of 1.8 g of phosgene in 30 ml of anhydrous methylene chloride. After the dropping, the resulting mixture was elevated in temperature, and reacted at room temperature for 30 minutes. Subsequently, the excess phosgene and the solvent were removed by distillation under reduced pressure to obtain 3.5 g of pale brown, oily 4-acetyl-2-oxo-1-piperazinocarbonyl chloride.

IR (film) cm$^{-1}$: $\nu_{C=O}$ 1790, 1710, 1640

(2) A suspension of 1.0 g of 6-[D(−)-α-aminophenylacetamido]penicillanic acid in 20 ml of tetrahydrofuran containing 20% by volume of water was adjusted to a pH of 8.0 to 8.5 by gradual addition of triethylamine with stirring, and then cooled to 0° C. Into the thus treated suspension was dropped a solution of 900 mg of the aforesaid 4-acetyl-2-oxo-1-piperazinocarbonyl chloride in 5 ml of tetrahydrofuran at said temperature over a period of 30 minutes. During this period, the pH of the suspension was maintained at 7.5 to 8.0 by gradual addition of triethylamine. Subsequently, the temperature of resulting mixture was elevated to 5° to 10° C, and the mixture was reacted at said temperature for 1 hour while maintaining the pH thereof at 7.5 to 8.0 by addition of triethylamine. After the reaction, the tetrahydrofuran was removed by reduced pressure distillation, and the residue was dissolved in a mixed solvent comprising 30 ml of ethyl acetate and 10 ml of water. The resulting solution was adjusted to a pH of 1.5 to 2 by addition of dilute hydrochloric acid with ice-cooling, and then the organic layer was separated off. The aqueous layer was re-extracted with 20 ml of ethyl acetate, and the resulting organic layer was combined with the aforesaid organic layer. The combined organic layer was washed with water, dried over anhydrous magnesium sulfate, and then ice-cooled. Into this organic layer was dropped a solution of 470 mg of a sodium salt of 2-ethylhexanoic acid in 20 ml of ethyl acetate to deposit white crystals. The deposited crystals were collected by filtration, washed with ethyl acetate and then dried to obtain 1.4 g of a sodium salt of 6-[D(−)-α-(4-acetyl-2-oxo-1-piperazinocarbonylamino)-phenylacetamido]penicillanic acid, m.p. 205° C (decomp.), yield 94%.

IR (KBr) cm$^{-1}$: $\nu_{C=O}$ 1760 (lactam), 1600 - 1700 (—COO$^{\ominus}$, —CON<)

NRM: [(CD$_3$)$_2$SO + D$_2$O] π values: 2.73 (5H), 4.35 (1H), 4.75 (2H), 5.75 (1H), 5.84 (2H), 6.42 (4H), 8.03 (3H), 8.52 (3H), 8.64 (3H)

The above-mentioned operation was repeated, except that the 4-acetyl-2-oxo-1-piperazinocarbonyl chloride was replaced by each of the rective derivatives of compounds of formula (III) shown in Table 8, to obtain the respective objective compounds as shown in Table 8. The structure of each objective compound was confirmed by IR and NMR.

Table 8
| Reactive derivative of compound of formula (III) | Objective compound |
|---|---|
| 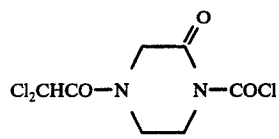 | D(-)-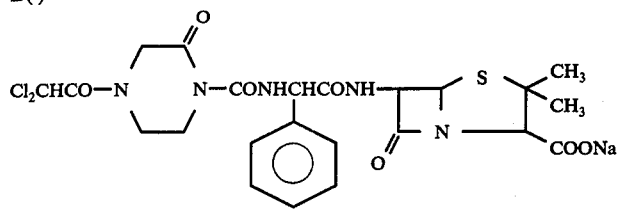
m.p. (decomp.) 203 – 205° C, yield 73 % |
| 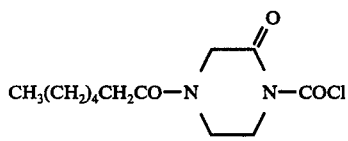 | D(-)-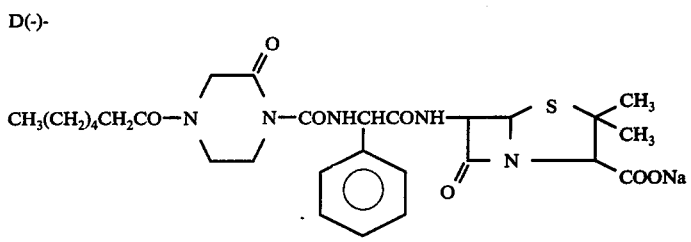
m.p. (decomp.) 202° C, yield 85.5 % |
| 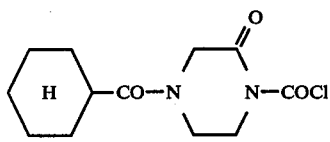 | D(-)-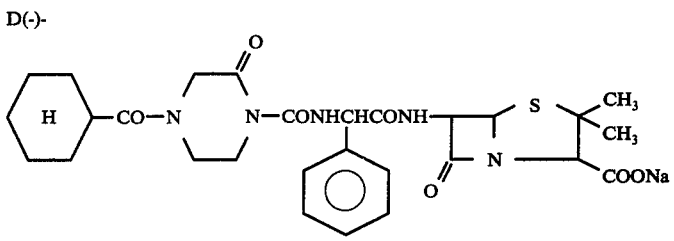
m.p. (decomp.) 203 – 205° C, yield 87.7 % |
| 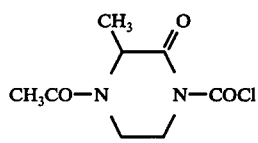 | D(-)-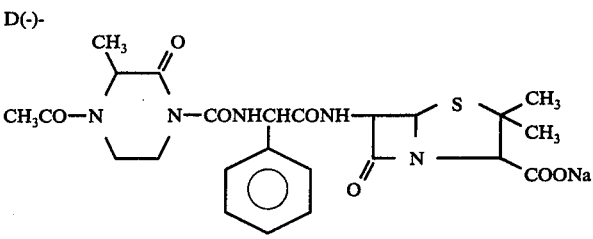
m.p. (decomp.) 199 – 200° C, yield 95 % |
| 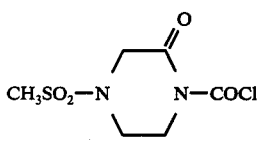 | D(-)-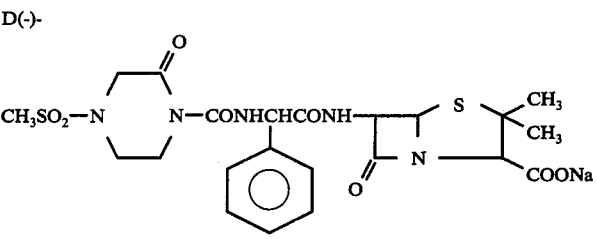
m.p. (decomp.) 199° C, yield 80 % |
| 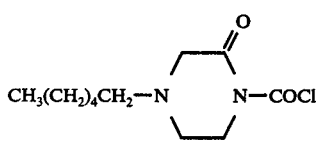 | D(-)-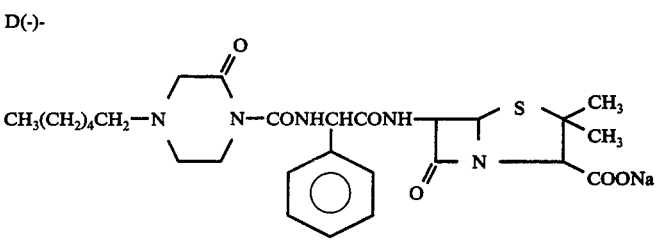
m.p. (decomp.) 171 – 174° C, yield 74 %
D(-)- |

Table 8-continued

| Reactive derivative of compound of formula (III) | Objective compound |
|---|---|
| 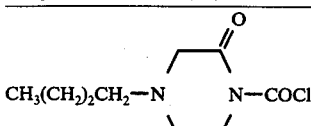 | 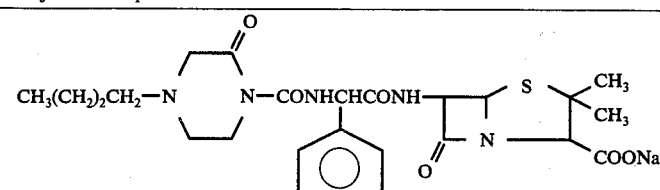<br>m.p. (decomp.) 158 – 161° C, yield 69 %<br>D(-)- |
| 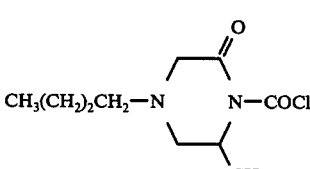 | 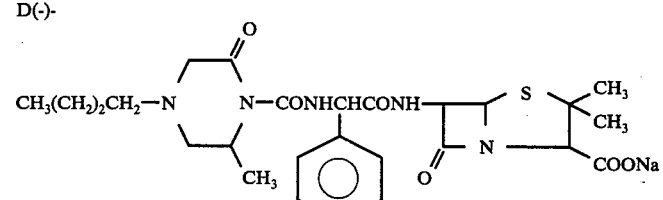<br>m.p. (decomp.) 188 – 190° C, yield 81 %<br>D(-)- |
| 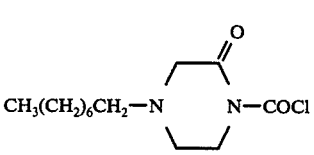 | 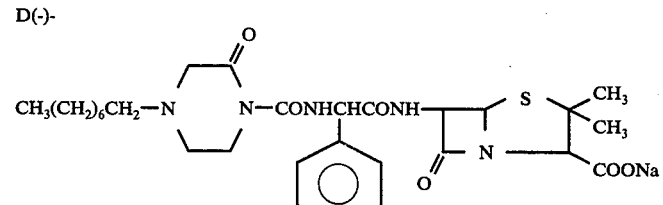<br>m.p. (decomp.) 132 – 134° C, yield 63 %<br>D(-)- |
| 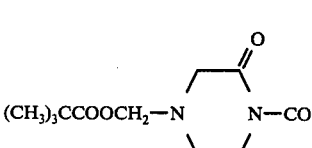 | 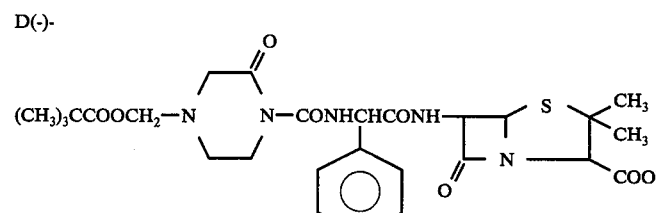<br>m.p. (decomp.) 218° C, yield 80 % |

EXAMPLE 2

(1) Into a solution of 1.74 g of a sodium salt of D(—)-α-aminophenylacetic acid in 30 ml of tetrahydrofuran containing 20% by volume of water which had been cooled to 0° C, a solution of 2.5 g of 4-acetyl-2-oxo-1-piperazinocarbonyl chloride in 5 ml of tetrahydrofuran was dropped at said temperature over a period of 30 minutes. During this period, the pH of the reaction solution was maintained at 11.0 to 12.0 by gradual addition of a 10% aqueous sodium hydroxide solution. Subsequently, the temperature of the resulting mixed solution was elevated to 5° to 10° C, and the solution was reacted at room temperature for 2 hours while maintaining the pH thereof at 10.0 to 11.0 by addition of a 10% aqueous sodium hydroxide solution. After the reaction, the tetrahydrofuran was removed by reduced pressure distillation. The residue was dissolved in a mixed solvent comprising 20 ml of water and 50 ml of ethyl acetate, and the resulting solution was adjusted to a pH of 1.0 to 1.5 by addition of dilute hydrochloric acid with ice-cooling. Subsequently, the organic layer was separated off, washed with water and then dried over anhydrous magnesium sulfate. To this organic layer, a solution of 1.66 g of a sodium salt of 2-ethylhexanoic acid in 20 ml of ethyl acetate was added to deposit white crystals. The deposited crystals were collected by filtration, sufficiently washed with ethyl acetate and then dried to obtain 1.89 g of a sodium salt of D(—)-α-(4-acetyl-2-oxo-1-piperazinocarbonylamino)phenylacetic acid, m.p. 115° C (decomp.), yield 52%.

IR (KBr) cm$^{-1}$: $\nu_{C=O}$ 1690, 1650 – 1600

(2) To a suspension in 15 ml of anhydrous acetone of 833 mg of the above-mentioned sodium salt of D(—)-α-(4-acetyl-2-oxo-1-piperazinocarbonylamino)phenylacetic acid was added 10 mg of N-methylmorpholine. The resulting mixture was colled to —20° to —15° C, and a solution of 286 mg of ethyl chlorocarbonate in 5 ml of anhydrous acetone was dropped into said mixture over a period of 5 minutes. Subsequently, the mixture was stirred at said temperature for 60 minutes. Into the thus treated mixture, a solution of 646 mg of a triethylamine salt of 6-aminopenicillanic acid in 30 ml of anhydrous methylene chloride was dropped at —40° to —30° C over a period of 10 minutes. Thereafter, the mixture was reacted with stirring at —30° to —20° C for 60 minutes, at —20° to —10° C for 30 minutes, and at —10° to 0° C for 30 minutes. After the reaction, the organic solvent was removed by reduced pressure distillation. The residue was dissolved in a mixed solvent comprising 50 ml of ethyl acetate and 20 ml of water, and the resulting solution was adjusted to a pH of 1.5 to 2.0 by addition of dilute hydrochloric acid with ice-cooling. Subsequently, the organic layer was separated off, sufficiently washed with water and then dried over anhydrous magnesium sulfate, and the ethyl acetate was removed by reduced pressure distillation. The residue was dissolved in 50 ml of acetone, and the resulting solution was mixed with a solution of 340 mg of a sodium salt of 2-ethylhexanoic acid in 20 ml of acetone with ice-cooling to deposit white crystals. The deposited crystals were collected by filtration, sufficiently washed with acetone and then dried to obtain 1.16 g of a sodium salt of 6-[D(−)-α-(4-acetyl-2-oxo-1-piperazinocarbonylamino)phenylacetamido]penicillanic acid, m.p. 205° C (decomp.), yield 94 %.

EXAMPLE 3

(1) To a mixture comprising 1.0 g of 1-palmitoyl-3-oxo-piperazine, 0.6 g of triethylamine and 20 ml of anhydrous dioxane was added a solution of 0.65 g of trimethylchlorosilane in 10 ml of anhydrous dioxane. The resulting mixture was refluxed for 16 hours and cooled to deposit triethylamine hydrochloride, which was then removed by filtration. The filtrate was dropped at −40° to −30° C into a solution of 0.6 g of phosgene in 30 ml of anhydrous methylene chloride. After the dropping, the temperature of the resulting mixture was elevated and the mixture was reacted at room temperature for 30 minutes. Subsequently, the excess phosgene and the solvent were removed by reduced pressure distillation to obtain 1.1 g of pale yellow, oily 4-palmitoyl-2-oxo-1-piperazinocarbonyl chloride.

IR (film) cm$^{-1}$: $\nu_{C=O}$ 1740, 1660, 1640

(2) A suspension of 1.0 g of 6-[D(−)-α-aminophenylacetamido]penicillanic acid in 20 ml of tetrahydrofuran containing 20 % by volume of water was adjusted to a pH of 8.0 to 8.5 by gradual addition of triethylamine with stirring, and then cooled to 0° C.

Into the thus treated suspension, a solution of 1.27 g of the aforesaid 4-palmitoyl-2-oxo-1-piperazinocarbonyl chloride in 5 ml of tetrahydrofuran was dropped at said temperature over a period of 30 minutes. During this period, the pH of the suspension was maintained at 7.5 to 8.0 by gradual addition of triethylamine. Subsequently, the temperature of the resulting mixture was elevated to 5° to 10° C, and the mixture was reacted at said temperature for 1 hour while maintaining the pH thereof at 7.5 to 8.0 by addition of triethylamine. After the reaction, the tetrahydrofuran was removed by reduced pressure distillation, and the residue was dissolved in a mixed solvent comprising 30 ml of ethyl acetate and 10 ml of water. The resulting solution was adjusted to a pH of 1.0 to 2.0 by addition of dilute hydrochloric acid with ice-cooling, and then the organic layer was separated off. The aqueous layer was re-extracted with 20 ml of ethyl acetate, and the resulting organic layer was combined with the aforesaid organic layer. The combined organic layer was washed with water, and dried over anhydrous magnesium sulfate. This organic layer was concentrated under reduced pressure to remove the solvent, and the concentrate was charged into 10 ml of diisopropyl ether to deposit crystals. Thereafter, the crystals were collected by filtration to obtain 1.65 g of white crystals of 6-[D(−)-α-(4-palmitoyl-2-oxo-1-piperazinocarbonylamino)-phenylacetamido]penicillanic acid, m.p. 121° − 123° C (decomp.), yield 80 %.

IR (KBr) cm$^{-1}$: $\nu_{C=O}$ 1770 (lactam), 1730 (—COOH), 1660 − 1630 (—CON<).

The above-mentioned operation was repeated, except that the 4-palmitoyl-2-oxo-1-piperazinocarbonyl chloride was replaced by each of the reactive derivatives of compounds of formula (III) shown in Table 9, to obtain respective objective compounds as shown in Table 9. The structure of each objective compound was confirmed by IR and NMR.

Table 9

| Reactive derivative of compound of formula (III) | Objective compound |
|---|---|
| CH₃(CH₂)₅CH₂CO—N⟩N—COCl | D(-)- CH₃(CH₂)₅CH₂CO—N⟩N—CONHCHCONH—[penicillin]  m.p. (decomp.) 151 – 153° C, yield 82 % |
| CH₃(CH₂)₃CH₂CO—N⟩N—COCl | D(-)- CH₃(CH₂)₃CH₂CO—N⟩N—CONHCHCONH—[penicillin]  m.p. (decomp.) 157 – 158° C, yield 83.3 % |
| | D(-)- |

Table 9-continued
| Reactive derivative of compound of formula (III) | Objective compound |
|---|---|
| 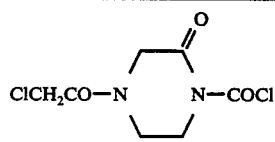 | 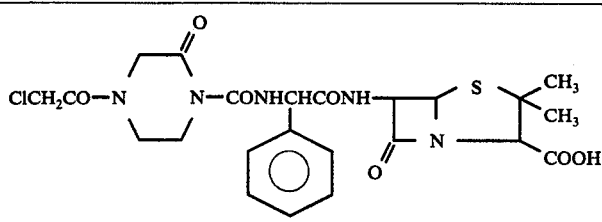 |
| | m.p. (decomp.) 215° C, yield 82.6 % |
| 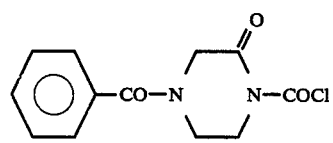 | 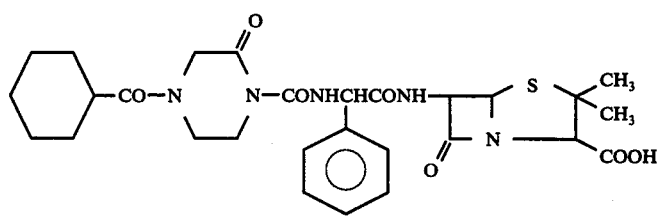 |
| | m.p. (decomp.) 120 – 124° C, yield 80 % |
| | D(-)- |
| 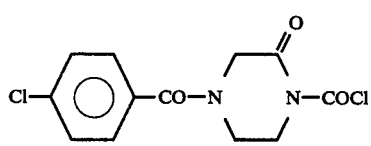 | 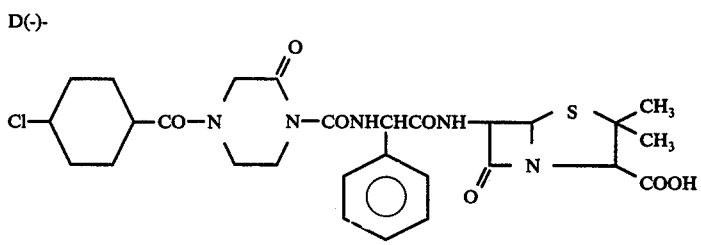 |
| | m.p. (decomp.) 120 – 123° C, yield 91 % |
| | D(-)- |
| 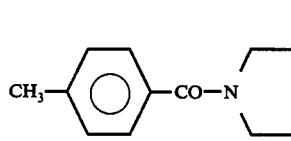 | 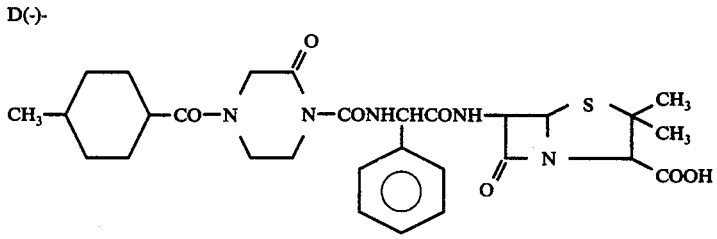 |
| | m.p. (decomp.) 105 – 108° C, yield 88.6 % |
| | D(-)- |
| 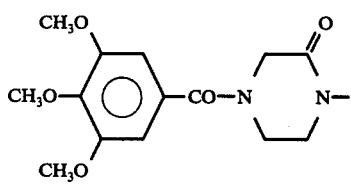 | 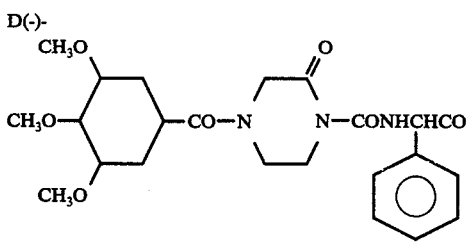 |
| | m.p. (decomp.) 120 – 124° C, yield 86.1 % |
| | D(-)- |
| 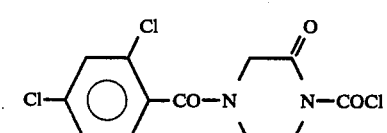 | 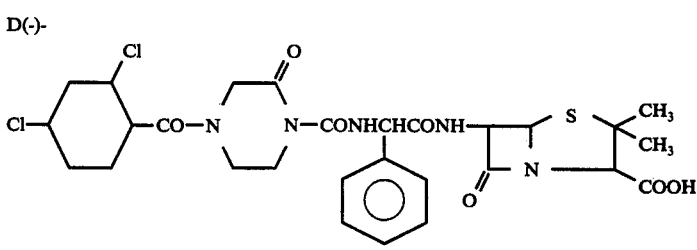 |
| | m.p. (decomp.) 130 – 133° C, yield 92 % |
| | D(-)- |

Table 9-continued

| Reactive derivative of compound of formula (III) | Objective compound |
|---|---|
| CH₃CONHCO—N( )N—COCl | CH₃CONHCO—N( )N—CONHCHCONH—[β-lactam]—S, CH₃, CH₃, COOH (phenyl on CH) <br> m.p. (decomp.) 172 –176° C, yield 79.2 % |
| D(-)- <br> (phenyl)—NHCO—N( )N—COCl | D(-)- <br> (cyclohexyl)—NHCO—N( )N—CONHCHCONH—[β-lactam]—S, CH₃, CH₃, COOH (phenyl on CH) <br> m.p. (decomp.) 168 – 170° C, yield 83.3 % |
| D(-)- <br> CH₃CH₂OCO—N( )N—COCl | D(-)- <br> CH₃CH₂OCO—N( )N—CONHCHCONH—[β-lactam]—S, CH₃, CH₃, COOH (phenyl on CH) <br> m.p. (decomp.) 86° C, yield 91 % |

EXAMPLE 4

(1) To a solution of 6.4 g of 1-formyl-3-oxopiperazine in 10 ml of anhydrous dimethylformamide was added 2.7 g of a sodium hydride (purity 53%) with ice-cooling, and the resulting mixture was reacted at room temperature for 1 hour. Subsequently, the mixture was incorporated with 7.1 g of methyl iodide and reacted for 10 hours. After the reaction, the dimethylformamide was removed by reduced pressure distillation to obtain 1-formyl-4-methyl-3-oxopiperazine. This piperazine was dissolved in 70 ml of a 50 % aqueous acetone solution containing 2.2 g of sodium hydroxide, and the resulting solution was reacted at room temperature for 3 hours. Thereafter, the solvent was removed by distillation under reduced pressure, and the residue was charged into acetone to deposit insolubles. The insolubles were separated by filtration, and the acetone was removed from the filtrate by distillation under reduced pressure. Subsequently, the residue was subjected to reduced pressure distillation to obtain 5.2 g of 1-methyl-2-oxo-piperazine, b.p. 104° C/4 mmHg, yield 91 %.

(2) Into a solution of 1.9 g of phosgene in 20 ml of anhydrous dioxane was dropped at 10° C 20 ml of an anhydrous dioxane solution containing 2.0 g of 1-methyl-2-oxo-piperazine and 1.95 g of triethylamine, upon which reaction took place to deposit white crystals of triethylamine hydrochloride. The deposited crystals were removed by filtration, and the filtrate was concentrated to dryness to obtain 3.0 g of pale yellow, oily 4-methyl-3-oxo-1-piperazinocarbonyl chloride.

IR (film) cm⁻¹: $\nu_{C=O}$ 1740, 1630

(3) A suspension of 4.0 g of 6-[D(—)-α-aminophenylacetamido]penicillanic acid in 40 ml of tetrahydrofuran containing 20 % by volume of water was adjusted to a pH of 8.0 to 8.5 by gradual addition of triethylamine with stirring, and then cooled to 0° C. Into the thus treated suspension, 10 ml of a tetrahydrofuran solution containing 2.2 g of the aforesaid 4-methyl-3-oxo-1-piperazinocarbonyl chloride was dropped. During this period, the pH of the suspension was maintained at 7.5 to 8.5 by gradual addition of triethylamine. Subsequently, the resulting mixture was reacted at said temperature for 30 minutes, and the temperature thereof was elevated to 10° to 15° C, after which the mixture was further reacted at said temperature for 90 minutes while maintaining the pH thereof at 7.5 to 8.0 by addition of triethylamine. After the reaction, the tetrahydrofuran was removed by distillation under reduced pressure, and the residue was dissolved in 30 ml of water. The resulting solution was washed with ethyl acetate, and then the aqueous layer was separated off. This aqueous layer was ice-cooled and then adjusted to a pH of 1.5 by addition of dilute hydrochloric acid to deposit white crystals. The deposited crystals were collected by filtration, washed several times with a small amount of water, dried, and then dissolved in 100 ml of acetone. To the resulting solution was added 1.9 g of a sodium salt of 2-ethylhexanoic acid with ice-cooling to deposit white crystals, which were then collected by filtration to obtain 5.4 g of a sodium salt of 6-[D(—)-α-(4-methyl-3-oxo-1-piperazinocarbonylamino)phenylacetamido]penicillanic acid, m.p. 195° C (decomp.), yield 92 %.

IR (KBr) cm⁻¹: $\nu_{C=O}$ 1760 (lactam), 1600 - 1660 (—CON<, —COO⁻)

NMR [(CD₃)₂SO + D₂O] π values: 2.62 (5H), 4.48 (1H), 4.56 (2H), 5.97 (3H), 6.63 - 6.39 (4H), 7.13 (3H), 8.46 (3H), 8.55 (3H)

The above-mentioned operation was repeated, except that the 4-methyl-3-oxo-1-piperazinocarbonyl chloride was replaced by each of the reactive derivatives of compounds of formula (III) shown in Table 10, to obtain respective objective compounds as shown in Table 10. The structure of each objective compound was confirmed by IR and NMR.

Table 10

| Reactive derivative of compound of formula (III) | Objective compound |
|---|---|
| 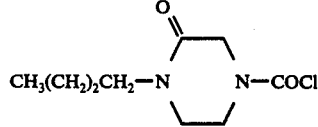 | D(-)- 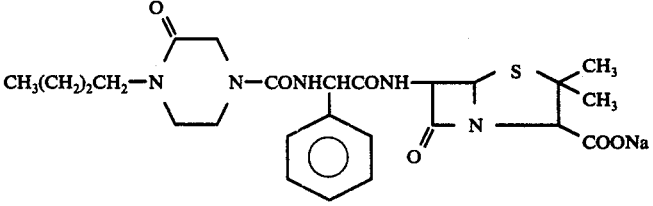<br>m.p. (decomp.) 206 – 207° C, yield 90% |
| 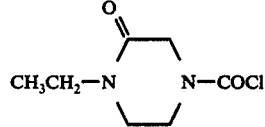 | D(-)- 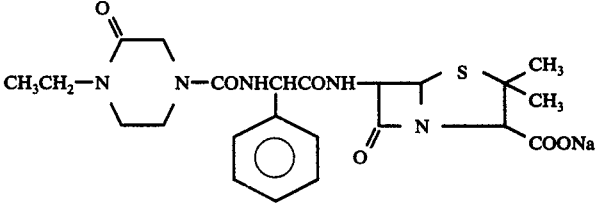<br>m.p. (decomp.) 207° C, yield 96% |
| 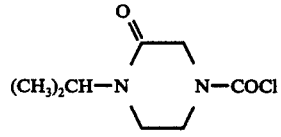 | D(-)- 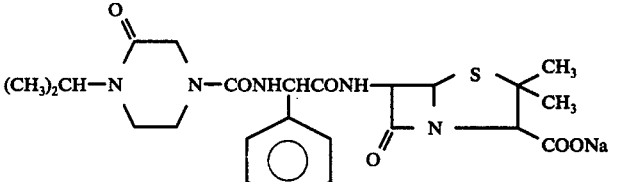<br>m.p. (decomp.) 208° C, yield 87% |
| 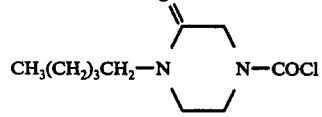 | D(-)- 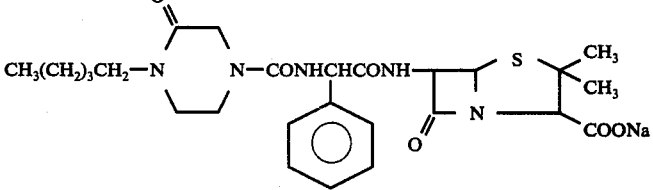<br>m.p. (decomp.) 200° C, yield 96% |
| 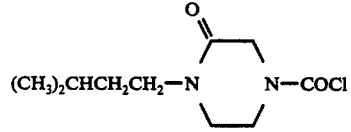 | D(-)- 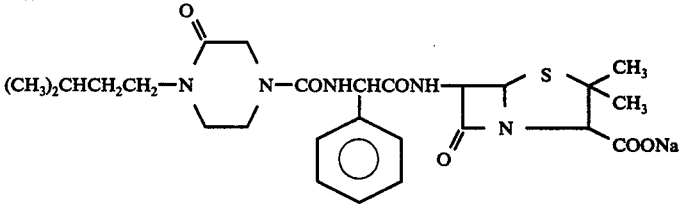<br>m.p. (decomp.) 185° C, yield 90% |
| 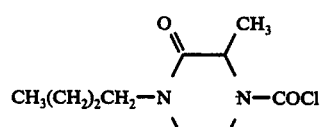 | D(-)- 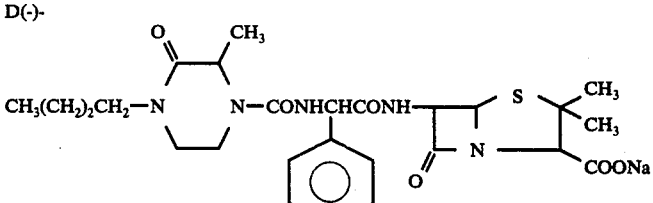<br>m.p. (decomp.) 193 – 197° C, yield 74% |

D(-)-

Table 10-continued
| Reactive derivative of compound of formula (III) | Objective compound |
|---|---|
| 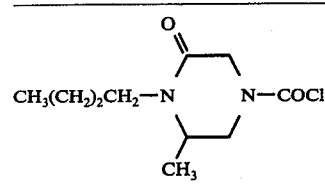 | 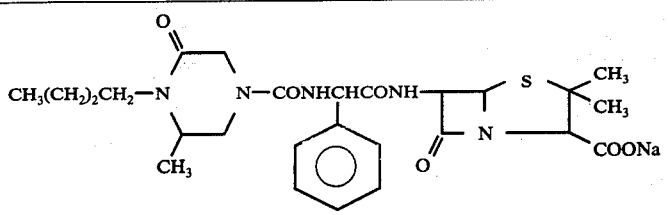<br>m.p. (decomp.) 199 – 202° C, yield 93% |
| 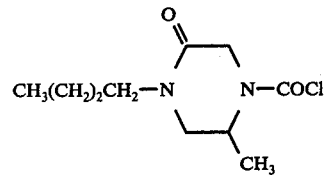 | D(-)-<br>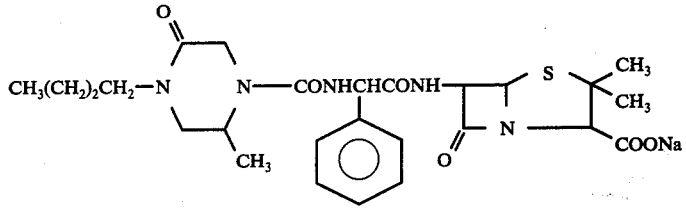<br>m.p. (decomp.) 191 – 194° C, yield 88% |
| 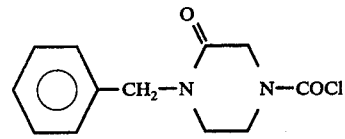 | D(-)-<br>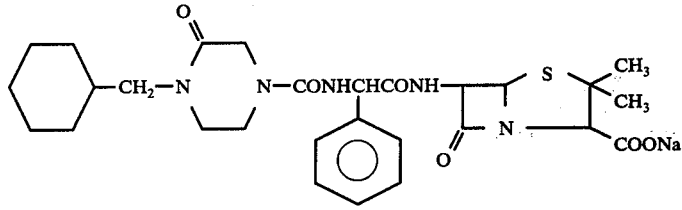<br>m.p. (decomp.) 100 – 105° C, yield 90% |
| 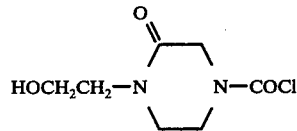 | D(-)-<br>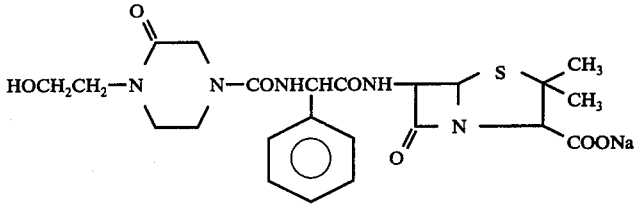<br>m.p. (decomp.) 100 – 105° C, yield 67% |
| 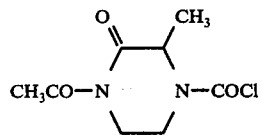 | D(-)-<br>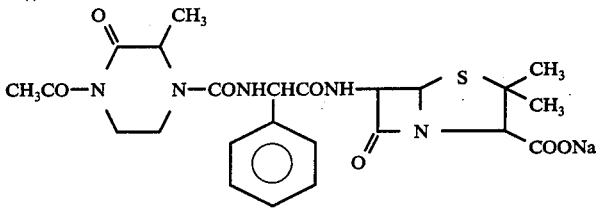<br>m.p. (decomp.) 202° C, yield 66% |
| 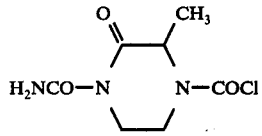 | D(-)-<br>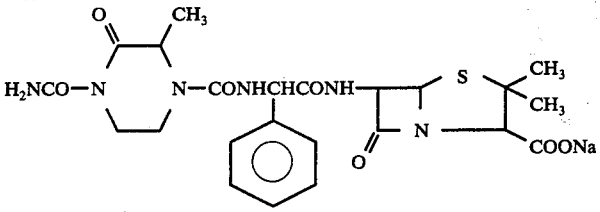<br>m.p. (decomp.) 215° C, yield 65% |

Table 10-continued

| Reactive derivative of compound of formula (III) | Objective compound |
|---|---|
| (structure: 3-oxopiperazine-1-carbonyl chloride) | (structure: penicillin derivative) m.p. (decomp.) 213° C, yield 70% |
| (structure: 2-methyl-3-oxopiperazine-1-carbonyl chloride) | D(-)- ... m.p. (decomp.) 203 – 206° C, yield 82% |
| (structure: 5-methyl-3-oxopiperazine-1-carbonyl chloride) | D(-)- ... m.p. (decomp.) 216 – 218° C, yield 87% |
| (structure: 2-ethoxycarbonylmethyl-3-oxopiperazine-1-carbonyl chloride) | D(-)- ... m.p. (decomp.) 200° C, yield 98% |
| (structure: 2-methyl-3-oxopiperazine-1-carbonyl chloride) | D(-)- ... m.p. (decomp.) 208° C, yield 75% |

EXAMPLE 5

(1) A solution of 1.0 g of a sodium salt of D(−)-α-aminophenyl acetic acid in 20 ml of tetrahydrofuran containing 20% by volume of water was cooled to 0° to 5° C. To this solution was added 1.2 g of 2-methyl-3-oxo-1-piperazinocarbonyl chloride over a period of 10 minutes. During this period the pH of the solution was maintained at 11.0 to 12.0 by gradual addition of a 10% aqueous sodium hydroxide solution. The solution was reacted at said temperature for 1 hour, and the temperature thereof was elevated to 5° to 10° C, after which the mixture was further reacted at said temperature for 2 hours, while maintaining the pH thereof at 10.0 to 11.0 by addition of a 10% aqueous sodium hydroxide solution. After the reaction, tetrahydrofuran was removed by distillation under reduced pressure, and the residue was dissolved in a mixed solvent comprising 20 ml of water and 50 ml of ethyl acetate. The resulting solution was adjusted to a pH of 1.5 by addition of dilute hydrochloric acid with ice-cooling, and then the organic layer was separated off. The aqueous layer was further extracted with 50 ml of ethyl acetate, and the resulting organic layer was combined with the aforesaid organic layer. The combined organic layer was washed with water and then dried over anhydrous magnesium sulfate. To this organic layer was added 0.9 g of a sodium salt of 2-ethylhexanoic acid to deposit white crystals. The deposited crystals were collected by filtration and then dried to obtain 1.26 g of white crystals of a sodium salt of D(—)-α-(2-methyl-3-oxo-1-piperazinocarbonylamino)phenylacetic acid, m.p. 215° C (decomp.), yield 70%.

IR (KBr) cm$^{-1}$: $\nu_{C=O}$ 1650 — 1590

(2) To a suspension in 15 ml of anhydrous acetone of 1.0 g of the above-mentioned sodium salt of D(—)-α-(2-methyl-3-oxo-1-piperazinocarbonylamino)phenylacetic acid was added 10 mg of N-methylmorpholine. The resulting mixture was cooled to —20° to —15° C, and a solution of 380 mg of ethyl chlorocarbonate in 5 ml of anhydrous acetone was dropped into said mixture over a period of 5 minutes. Subsequently, the mixture was stirred at said temperature for 60 minutes, and then cooled to —40° to —30° C. Into the thus treated mixture was dropped a solution of 960 mg of a triethylamine salt of 6-aminopenicillanic acid in 10 ml of anhydrous methylene chloride over a period of 10 minutes. Thereafter, the mixture was reacted with stirring at —30° to —20° C for 60 minutes, at —20° to —10° C for 30 minutes, and at —10° to 0° C for 30 minutes. After the reaction, the organic solvent was removed by distillation under reduced pressure. The residue was dissolved in a mixed solvent comprising 20 ml of water and 50 ml of ethyl acetate, and the resulting solution was adjusted to a pH of 1.5 by addition of dilute hydrochloric acid with ice-cooling. Subsequently, the organic layer was separated off, sufficiently washed with water and then dried over anhydrous magnesium sulfate. To this organic layer was added 0.5 g of a sodium salt of 2-ethylhexanoic acid with ice-cooling to deposit white crystals. The deposited crystals were collected by filtration, and then dried to obtain 1.39 g of a sodium salt of 6-[D(—)-α-(2-methyl-3-oxo-1-piperazinocarbonylamino)-phenylacetamido]penicillanic acid, m.p. 208° C (decomp.), yield 90%.

In the same manner as above, 2.0 g of a sodium salt of 6-[D(—)-α-(4-ethyl-3-oxo-1-piperazinocarbonylamino)-propionamido]penicillanic acid, m.p. 195° C (decomp.), yield 86%, was obtained from 1.59 g of a sodium salt of D(—)-α-(4-ethyl-3-oxo-1-piperazinocarbonylamino)-propionic acid and 1.59 g of a triethylamine salt of 6-aminopenicillanic acid.

IR (KBr) cm$^{-1}$: $\nu_{C=O}$ 1760 (lactam), 1680 — 1600 (—CON<, —COO$^\ominus$)

EXAMPLE 6

(1) Into a solution of 0.5 g of phosgene in 10 ml of anhydrous dioxane was dropped at 10° C 10 ml of anhydrous dioxane containing 0.56 g of 1-allyl-2-oxo-piperazine and 0.5 g of triethylamine, upon which reaction took place to deposit white crystals of triethylamine hydrochloride. Subsequently, the deposited crystals were collected by filtration, and the filtrate was concentrated to dryness to obtain 800 mg of pale yellow, oily 4-allyl-3-oxo-1-piperazinocarbonyl chloride.

IR (film) cm$^{-1}$: $\nu_{C=O}$ 1720, 1640

(2) A suspension of 1.4 g of 6-[D(—)-α-aminophenylacetamido]penicillanic acid in tetrahydrofuran containing 20% by volume of water was adjusted to a pH of 8.0 to 8.5 by gradual addition of triethylamine with stirring, and then cooled to 0° C. Into the thus treated suspension was dropped 10 ml of a tetrahydrofuran solution containing 800 mg of the aforesaid 4-allyl-3-oxo-1-piperazinocarbonyl chloride. During this period, the pH of the suspension was maintained at 7.5 to 8.5 by gradual addition of triethylamine. Subsequently, the resulting mixture was reacted at said temperature for 30 minutes, and the temperature thereof was then elevated to 10° to 15° C, after which the mixture was further reacted at said temperature for 90 minutes while maintaining the pH thereof at 7.5 to 8.0 by addition of triethylamine. After the reaction, the tetrahydrofuran was removed by distillation under reduced pressure, and the residue was dissolved in 20 ml of water. The resulting solution was washed with ethyl acetate, and the aqueous layer was then separated off. This aqueous layer was ice-cooled and adjusted to a pH of 1.5 by addition of dilute hydrochloric acid to deposit white crystals. The deposited crystals were collected by filtration, sufficiently washed with water and then dried to obtain 1.8 g of 6-[D(—)-α-(4-allyl-3-oxo-1-piperazinocarbonylamino)phenylacetamido]penicillanic acid, m.p. 92° C (decomp.), yield 90%.

IR (KBr) cm$^{-1}$: $\nu_{C=O}$ 1760 (lactam), 1720 — 1620 (—COOH, —CON<)

The above-mentioned operation was repeated, except that the 4-allyl-3-oxo-1-piperazinocarbonyl chloride was replaced by each of the reactive derivatives of compounds of formula (III) shown in Table 11, to obtain respective objective compounds as shown in Table 11. The structure of each objective compound was confirmed by IR and NMR.

Table 11

| Reactive derivative of compound of formula (III) | Objective compound D(-)- |
|---|---|
| CH$_2$=CHCH(CH$_3$)—N\_\_/N—COCl | CH$_2$=CHCH(CH$_3$)—N\_\_/N—CONHCHCONH—[β-lactam-penicillin structure]—COOH<br>m.p. (decomp.) 102° C, yield 80 % |

Table 11-continued
| Reactive derivative of compound of formula (III) | Objective compound |
|---|---|
| 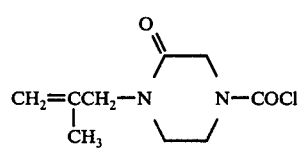 | D(-)- 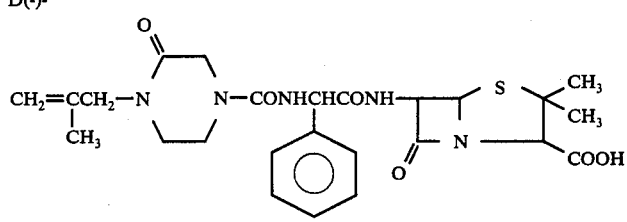<br>m.p. (decomp.) 90° C, yield 85 % |
| 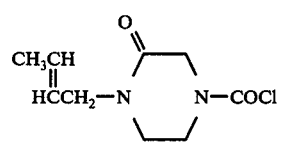<br>(trans-) | D(-)- 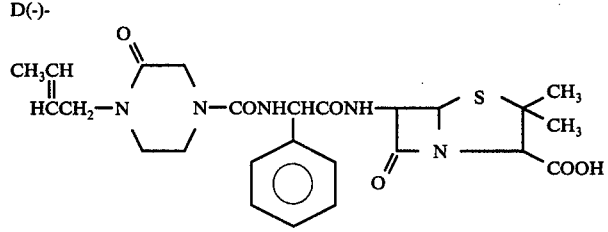<br>(trans-)<br>m.p. (decomp.) 95° C, yield 84 % |
| 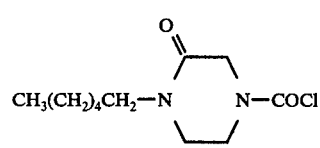 | D(-)- 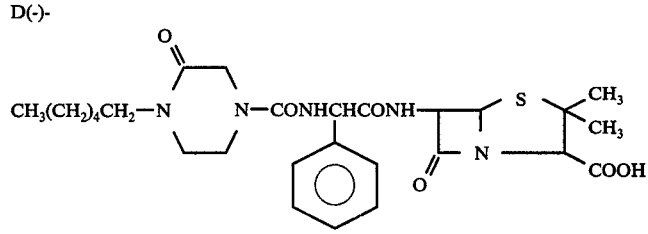<br>m.p. (decomp.) 128 – 130° C, yield 97 % |
| 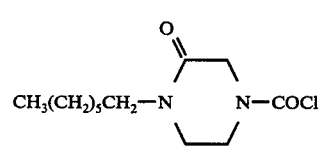 | D(-)- 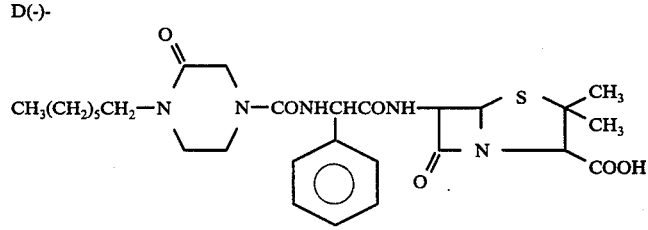<br>m.p. (decomp.) 120° C, yield 94 % |
| 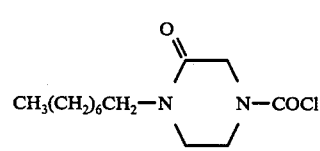 | D(-)- 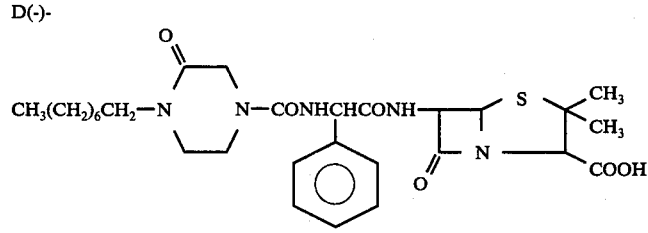<br>m.p. (decomp.) 110° C, yield 98 % |
| 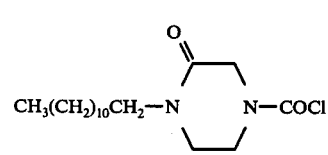 | D(-)- 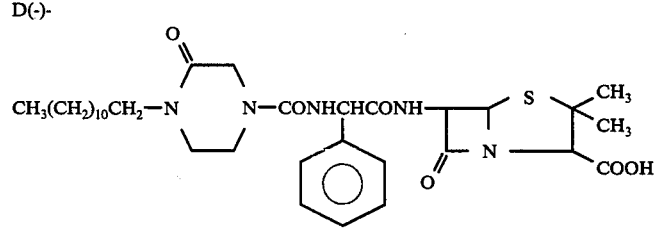<br>m.p. (decomp.) 106° C, yield 96 % |

Table 11-continued

| Reactive derivative of compound of formula (III) | Objective compound |
|---|---|
| [structure: cyclopentyl-NH attached to piperazinone N—COCl] | D(-)- [structure with penicillanic acid moiety] m.p. (decomp.) 134° C, yield 87 % |
| [structure: phenyl-NHCO-N piperazinone N—COCl] | D(-)- [structure: cyclohexyl-NHCO-N piperazinone N—CONHCHCONH- penicillanic] m.p. (decomp.) 150 - 153° C, yield 76 % |
| [structure: phenyl-CO-CH(NH)- piperazine N—COCl] | D(-)- [structure with penicillanic acid moiety] m.p. (decomp.) 125 - 128° C, yield 79.5 % |

EXAMPLE 7

Using 0.63 g of 6-[D(−)-α-aminophenylacetamido]-penicillanic acid and 600 mg of a hydrochloride of 4-(N-morpholinomethyl)-3-oxo-1-piperazinocarbonyl chloride, the same operation as in Example 6 was repeated to obtain 0.63 g of 6-[D(−)-α-[4-(N-morpholinomethyl)-3-oxo-1-piperazinocarbonylamino]-phenylacetamido]penicillanic acid, m.p. 85° C (decomp.), yield 60%.

IR (KBr) cm$^{-1}$: $\nu_{C=O}$: 1770 (lactam), 1600 − 1680 (—COO$^\ominus$—CON<)

EXAMPLE 8

Using 5.0 g of a hydrochloride of pivaloyloxymethyl ester of 6-[D(−)-α-aminophenylacetamido]-penicillanic acid and 1.94 g of 2-methyl-3-oxo-1-piperazinocarbonyl chloride, the same operation as in Example 6 was repeated to obtain 5.2 g of a pivaloyloxymethyl ester of 6-[D(−)-α-(2-methyl-3-oxo-1-piperazinocarbonylamino)phenylacetamido]penicillanic acid, m.p. 140° C (decomp.), yield 80%.

IR (KBr) cm$^{-1}$: $\nu_{C=O}$ 1740 − 1770 (lactam, ester) 1630 − 1670 (—CON<)

EXAMPLE 9

(1) Into a mixture comprising 8.0 g of 4-acetyl-2,5-dioxo-piperazine, 5.0 g of triethylamine and 100 ml of anhydrous tetrahydrofuran was dropped 6.0 g of trimethylchlorosilane with stirring at room temperature. After the dropping, the resulting mixture was reacted at said temperature for 2 hours to deposit triethylamine hydrochloride. The deposited hydrochloride was separated by filtration, and the filtrate was dropped at 0° to 5° C into 100 ml of an anhydrous tetrahydrofuran solution containing 10.0 g of phosgene. After completion of the dropping, the resulting mixture was stirred at 10° to 15° C for 3 hours to terminate the reaction. Subsequently, the tetrahydrofuran and the excess phosgene were removed by distillation under reduced pressure to obtain 11.0 g of oily 4-acetyl-2,5-dioxo-1-piperazinocarbonyl chloride.

(2) A suspension of 17.5 g of 6-[D(−)-α-aminophenylacetamido]penicillanic acid in 200 ml of tetrahydrofuran containing 20% by volume of water was adjusted to a pH of 8.0 to 8.5 by gradual addition of triethylamine with stirring at 10° to 15° C to form a homogeneous solution. Into this solution was dropped a solution of 11.0 g of the aforesaid 4-acetyl-2,5-dioxo-1-piperazinocarbonyl chloride in 30 ml of tetrahydrofuran at 0° C over a period of 30 minutes. During this period, the pH of the reaction solution was maintained at 7.5 to 8.0 by gradual addition of triethylamine. Subsequently, the temperature of the resulting mixed solution was elevated to 5° to 10° C and the solution was further reacted for 1 hour while maintaining the pH thereof at 7.5 to 8.0 by addition of triethylamine. After completion of the reaction, the tetrahydrofuran was removed by distillation under reduced pressure. To the residue was added 100 cc of N hydrochloric acid at 0° to 10° C, and the resulting mixture was stirred for 30 minutes to deposit white crystals. The deposited crystals were collected by filtration, and again suspended in water. The resulting aqueous suspension was adjusted to a pH of 8.0 by gradual addition of triethylamine at 5° to 10° C, and then freed from insolubles by filtration. The filtrate was adjusted to a pH of 1.5 by gradual addition of N hydrochloric acid to deposit crystals. The deposited crystals were collected by filtration, washed with water and then dried to obtain 21.2 g of 6-[D(−)-α-(4-acetyl-2,5-dioxo-1-piperazinocarbonylamino)phenylacetamido]-penicillanic acid, m.p. 162°–164° C (decomp.), yield 80%.

IR (KBr) cm $^{-1}$: $\nu_{C=O}$ 1770 (lactam), 1730 − 1660 (—COOH, —CON<)

NMR ((CD$_3$)$_2$CO)τ values: 0.23 (1H), 2.65 (5H), 4.26 (1H), 4.33 − 4.63 ( 2H), 5.38 (4H), 5.68 (1H), 7.55 (3H), 8.47 ( 3H), 8.53 (3H)

The above-mentioned operation was repeated, except that the 4-acetyl-2,5-dioxo-1-piperazinocarbonyl chloride was replaced by each of the reactive derivatives of compounds of formula (III) shown in Table 12, to obtain respective objective compounds as shown in Table 12. The structure of each objective compound was confirmed by IR and NMR.

Table 12

| Reactive derivative of compound of formula (III) | Objective compound |
|---|---|
| [structure: phenyl-CO-N(piperazine-2,5-dione)-N-COCl] | D(-)- [structure with penicillanic acid] m.p. (decomp.) 88° C, yield 60 % |
| [structure: CH$_3$-N(piperazine-2,5-dione)-N-COCl] | D(-)- [structure with penicillanic acid] m.p. (decomp.) 179 – 181° C, yield 83 % |
| [structure: phenyl-CH$_2$-N(piperazine-2,5-dione)-N-COCl] | D(-)- [structure with penicillanic acid] m.p. (decomp.) 88° C, yield 82 % |
| D(-)- [structure: cyclohexyl-HN(piperazinone)-N-COCl] | [structure with penicillanic acid] m.p. 214 – 215° C, yield 89.6 % |
| [structure: HN(piperazine-2,5-dione)-N-COCl] | D(-)- [structure with penicillanic acid] m.p. (decomp.) 176 – 181° C, yield 84.4 % |

Table 12-continued

| Reactive derivative of compound of formula (III) | Objective compound |
|---|---|
| D(-)- 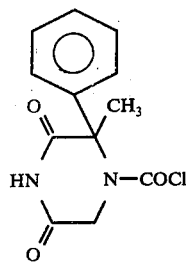 | 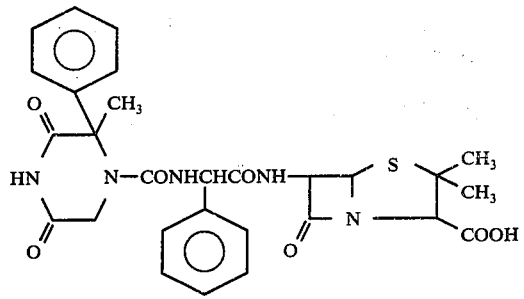<br>m.p. (decomp.) 148 - 151° C, yield 92 % |
| D(-)- 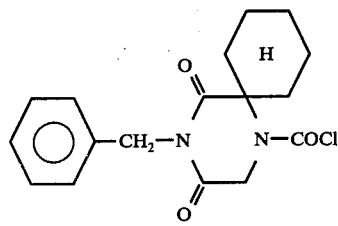 | D(-)-<br>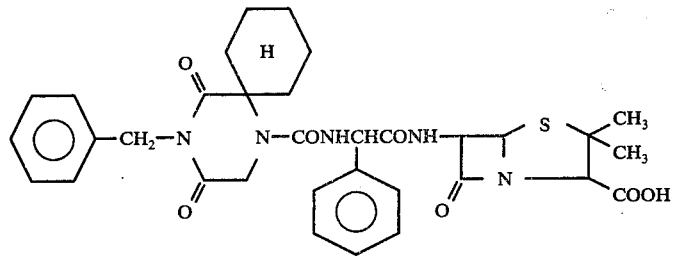<br>m.p. (decomp.) 95 - 100° C, yield 91 % |
| D(-)- 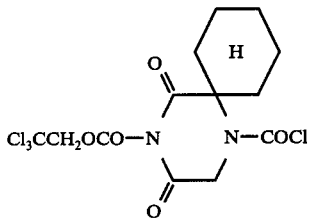 | 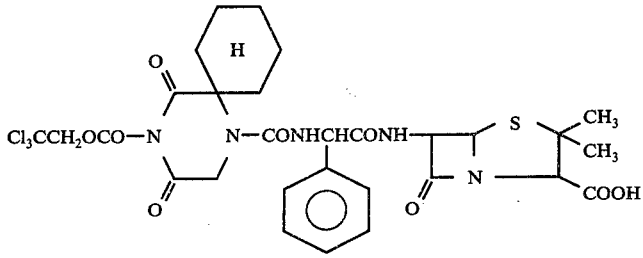<br>m.p. (decomp.) 120 - 125° C, yield 92 % |
| D(-)- 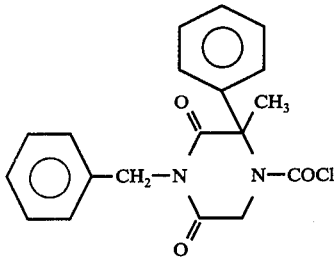 | 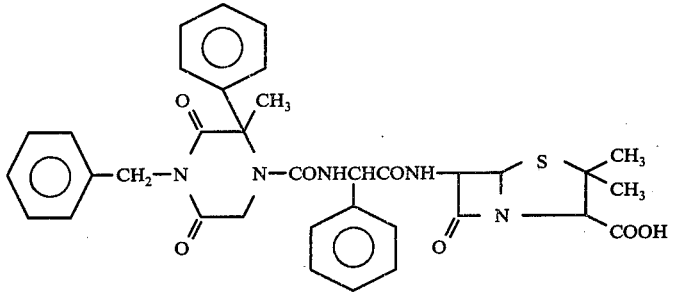<br>m.p. (decomp.) 147 - 149° C, yield 89 % |

EXAMPLE 10

(1) A suspension of 8.0 g of D(—)-α-aminophenyl acetic acid in 80 ml of tetrahydrofuran was adjusted to a pH of 11.5 by gradual addition of a N sodium hydroxide solution with stirring to form a homogeneous solution. This solution was cooled to 0° C, and 15 ml of a tetrahydrofuran solution containing 11 g of 4-acetyl-2,5-dioxo-1-piperazinocarbonyl chloride was dropped at said temperature into said solution over a period of 30 minutes. During this period, the pH of the reaction solution was maintained at 10.5 to 11.0 by a gradual addition of a N sodium hydroxide solution. Subsequently, the temperature of the resulting mixed solution was elevated to 5° to 10° C, and the mixture was further reacted for 1 hour, upon which D(—)-α-aminophenylacetic acid deposited. After completion of the reaction, the deposited acid was separated by filtration, and the filtrate was concentrated under reduced pressure to remove tetrahydrofuran. The residue was dissolved in a mixed solvent comprising 10 ml of water and 80 ml of ethyl acetate, and the resulting solution was adjusted to a pH of 1.0 by addition of dilute hydrochloric acid with ice-cooling. Subsequently, the organic layer was separated off, dried over anhydrous magnesium sulfate, and then charged into 100 ml of an ethyl acetate solution containing 8.3 g of sodium 2-ethylhexanoate to deposit crystals. The deposited crystals were collected by filtration, washed with acetone, and then dried over $P_2O_5$ to obtain 7.9 g of a sodium salt of D(—)-α-(4-acetyl-2,5-dioxo-1-piperazinocarbonylamino)phenylacetic acid, m.p. 104° C (decomp.), yield 42%.

IR (KBr) $cm^{-1}$: $\nu_{C=O}$ 1690 — 1650, 1600 — 1590

(2) To a suspension in 25 ml of anhydrous acetone of 1.75 g of the aforesaid sodium salt of D(—)-α-(4-acetyl-2,5-dioxo-1-piperazinocarbonylamino)phenyl acetic acid was added 20 mg of N-methylmorpholine, and the resulting mixture was cooled to —20° to —15° C. Into this mixture was dropped a solution of 0.57 g of ethyl chlorocarbonate in 5 ml of anhydrous acetone over a period of 5 minutes, and the mixture was stirred at said temperature for 60 minutes. Subesequently, a solution of 1.29 g of a triethylamine salt of 6-aminopenicillanic acid in 30 ml of anhydrous methylene chloride was dropped into said mixture at —40° to —30° C over a period of 10 minutes. The temperature of the resulting mixture was elevated from —30° C to 0° C, and the mixture was then reacted at said temperature for about 2 hours. After the reaction, the solvent was removed by distillation under reduced pressure. The residue was charged into 30 ml of water, and the resulting mixture was freed from insolubles by filtration with ice-cooling. The filtrate was adjusted to a pH of 1.5 to 2.0 by addition of dilute hydrochloric acid to deposit crystals. The deposited crystals were collected by filtration, sufficiently washed with water, and then dried to obtain 2.34 g of 6-[D(—)-α-(4-acetyl-2,5-dioxo-1-piperazinocarbonylamino)-phenylacetamido]penicillanic acid, m.p. 162° – 164° C (decomp.), yield 90%.

In the same manner as above, 530 mg of 6-[D(—)-α-(4-benzyl-2,2-pentamethylene-3,5-dioxo-1-piperazinocarbonylamino)phenylacetamido]penicillanic acid, m.p. 95° – 100° C, yield 82.68%, was obtained from 450 mg of D(—)-α-(4-benzyl-2,2-pentamethylene-3,5-dioxo-1-piperazinocarbonylamino)-phenylacetic acid and 320 mg of a triethylamine salt of 6-aminopenicillanic acid.

IR (KBr) $cm^{-1}$: $\nu_{C=O}$ 1770 (lactam), 1700 — 1660 (—COOH, —CON<)

EXAMPLE 11

(1) Into a mixture comprising 8 g of a diethyl ester of oxalic acid and 8 ml of ethanol was dropped at room temperature 4.4 g of N-ethyl ethylenediamine. The resulting mixture was allowed to react for 3 hours, and then heated to remove the ethanol. Subsequently, the residue was recrystallized from 10 ml of dioxane to obtain 5.4 g of 1-ethyl-2,3-dioxopiperazine, m.p. 124° C, yield 76.0%.

(2) To a suspension of 0.71 g of the abovementioned 1-ethyl-2,3-dioxo-piperazine in 15 ml of anhydrous dioxane were added with stirring 0.70 g of trimethylsilyl chloride and 0.83 ml of triethylamine. The resulting mixture was stirred at room temperature for 20 hours to deposit triethylamine hydrochloride. This hydrochloride was separated by filtration, and the filtrate was dropped at 5° to 10° C into a solution of 0.70 g of phosgene in 10 ml of anhydrous tetrahydrofuran. Subsequently, the resulting mixture was reacted at 5° to 10° C for 30 minutes and at room temperature for 2 hours, and then the solvent was removed by distillation under reduced pressure to obtain 1.0 g of pale yellow crystals of 4-ethyl-2,3-dioxo-1-piperazinocarbonyl chloride.

IR (KBr) $cm^{-1}$: $\nu_{C=O}$ 1780, 1660

(3) A suspension of 1.75 g of 6[D(—)-α-aminophenylacetamido]penicillanic acid in 30 ml of tetrahydrofuran containing 20% by volume of water was adjusted to a pH of 8.0 by addition of triethylamine with stirring to form a solution. This solution was cooled to 0° to 5° C, and then 7 ml of an anhydrous tetrahydrofuan solution containing 1.0 g of the aforesaid 4-ethyl-2,3-dioxo-1-piperazinocarbonyl chloride was dropped into the solution. During this period, the pH of the reaction solution was maintained at 7.5 to 8.0 by gradual addition of triethylamine. The resulting mixed solution was reacted at said temperature for 30 minutes and then at 5° to 10° C for 1 hour, while maintaining the pH thereof at 7.5 to 8.0. After the reaction, the tetrahydrofuran was removed by distillation under reduced pressure, and the residue was dissolved in 20 ml of water and then washed two times with 20 ml of ethyl acetate. To the aqueous layer was again added 50 ml of ethyl acetate, and the resulting mixture was adjusted to a pH of 1.5 by gradual addition of dlute hydrochloric acid with ice-cooling. Subsequently, the ethyl acetate layer was separated off, sufficiently washed with water, and then dried over anhydrous magnesium sulfate. Into the thus treated layer was dropped 10 ml of an ethyl acetate solution containing 0.83 g of sodium 2-ethylhexanoate to deposit white crystals. The deposited crystals were collected by filtration, sufficiently washed with ethyl acetate, washed with diethyl ether, and then dried to obtain 2.4 g of a sodium salt of 6-[D(—)-α-(4-ethyl-2,3-dioxo-1-piperazinocarbonylamino)phenylacetamido]-penicillanic acid, m.p. 183° – 185° C (decomp.), yield 89%.

IR (KBr) $cm^{-1}$: $\nu_{C=O}$ 1765 (lactam), 1720 — 1670 (—CON<), 1600 (—COO$^{\ominus}$)

NMR $(CD_3)_2SO + D_2O)$ τ values: 2.62 (5H), 4.31 (1H), 4.50 (1H), 4.70 (1H), 6.05 (1H), 6.35 – 6.65 (6H), 8.49 (3H), 8.60 (3H), 8.91 (3H)

The above-mentioned operation was repeated, except that the 4-ethyl-2,3-dioxo-1-piperazinocarbonyl chloride was replaced by each of the reactive derivatives of compounds of formula (III) shown in Table 13, to obtain respective objective compounds as shown in Table 13. The structure of each objective compound was confirmed by IR and NMR.

Table 13

| Reactive derivative of compound of formula (III) | Objective compound |
| --- | --- |
| ![CH3-N piperazine N-COCl structure] | D(-)- ![CH3-N piperazine N-CONHCHCONH-phenyl-penicillin-COONa structure] m.p. (decomp.) 170° C, yield 84 % |

Table 13-continued

| Reactive derivative of compound of formula (III) | Objective compound |
|---|---|
| CH₃CH₂CH₂—N(piperazine-2,3-dione)—N—COCl | D(-)- CH₃CH₂CH₂—N(piperazine-2,3-dione)—N—CONHCHCONH—(penicillin with phenyl) COONa<br>m.p. (decomp.) 170° C, yield 86 % |
| CH₃(CH₂)₂CH₂—N(piperazine-2,3-dione)—N—COCl | D(-)- CH₃(CH₂)₂CH₂—N(piperazine-2,3-dione)—N—CONHCHCONH—(penicillin with phenyl) COONa<br>m.p. (decomp.) 190° C, yield 87 % |
| (CH₃)₂CH—N(piperazine-2,3-dione)—N—COCl | D(-)- (CH₃)₂CH—N(piperazine-2,3-dione)—N—CONHCHCONH—(penicillin with phenyl) COONa<br>m.p. (decomp.) 186° C, yield 85 % |
| CH₃COOCH₂CH₂—N(piperazine-2,3-dione)—N—COCl | D(-)- CH₃COOCH₂CH₂—N(piperazine-2,3-dione)—N—CONHCHCONH—(penicillin with phenyl) COONa<br>m.p. (decomp.) 175° C, yield 79 % |
| CH₂=CHCH₂—N(piperazine-2,3-dione)—N—COCl | D(-)- CH₂=CHCH₂—N(piperazine-2,3-dione)—N—CONHCHCONH—(penicillin with phenyl) COONa<br>m.p. (decomp.) 198 – 200° C, yield 75 % |
| C₆H₅—N(piperazine-2,3-dione)—N—COCl | D(-)- C₆H₅—N(piperazine-2,3-dione)—N—CONHCHCONH—(penicillin with phenyl) COONa<br>m.p. (decomp.) 185 – 187° C, yield 88 % |

Table 13-continued

| Reactive derivative of compound of formula (III) | Objective compound |
|---|---|
| 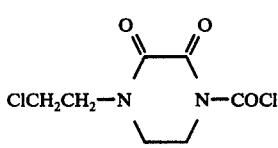 ClCH₂CH₂—N⟩N—COCl | D(-)- 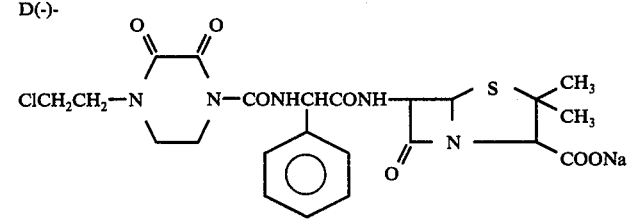 ClCH₂CH₂—N⟩N—CONHCHCONH—[penicillin]—COONa<br>m.p. (decomp.) 210° C, yield 83 % |
| 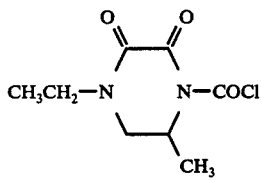 CH₃CH₂—N⟩N—COCl (with CH₃) | D(-)- 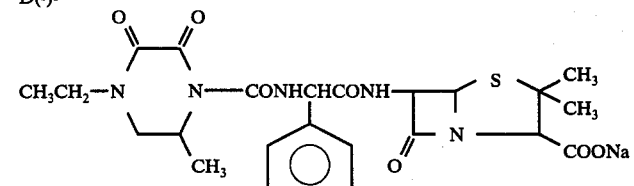 CH₃CH₂—N⟩N—CONHCHCONH—[penicillin]—COONa<br>m.p. (decomp.) 175 – 177° C, yield 76 % |
| 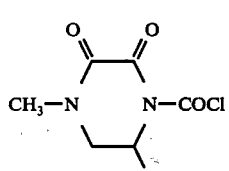 CH₃—N⟩N—COCl (with CH₃) | D(-)- 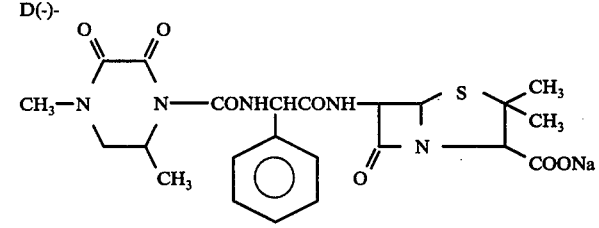 CH₃—N⟩N—CONHCHCONH—[penicillin]—COONa<br>m.p. (decomp.) 177 – 178° C, yield 79 % |

EXAMPLE 12

A suspension of 1.4 g of 6[D(—)-α-aminophenylacetamido]penicillanic acid in 30 ml of tetrahydrofuran containing 20% by volume of water was adjusted to a pH of 8.0 to 8.5 by addition of triethylamine with stirring to form a solution. This solution was cooled to 0° to 5° C, and 10 ml of a tetrahydrofuran solution containing 1.2 g of 4-n-pentyl-2,3-dioxo-1-piperazinocarbonyl chloride was dropped into said solution. During this period, the pH of the reaction solution was maintained at 7.5 to 8.5 by gradual addition of triethylamine. Subsequently, the resulting mixed solution was reacted at said temperature for 30 minutes and then at 10° to 15° C for 90 minutes, while maintaining the pH thereof at 7.5 to 8.5. After the reaction, the tetrahydrofuran was removed by distillation under reduced pressure, and the residue was dissolved in 20 ml of water and then washed two times with 20 ml of ethyl acetate. To the aqueous layer was further added 30 ml of ethyl acetate, and the resulting mixture was adjusted to a pH of 1.5 by addition of dilute hydrochloric acid with ice-cooling. Thereafter, the ethyl acetate layer was separated off, sufficiently washed with water, dried over magnesium sulfate, and then freed from the solvent by distillation under reduced pressure. The residue was crystallized by addition of diisopropyl ether to obtain 1.8 g of crystals of 6-[D(—)-α-(4-n-pentyl-2,3-dioxo-1-piperazinocarbonylamino)phenylacetamido]penicillanic acid, m.p. 96° C (decomp.), yield 80.5%.

IR (KBr) cm$^{-1}$: $\nu_{C=O}$ 1770 (lactam), 1720 — 1660 (—CON<, —COOH)

NMR ((CD₃)₂SO + D₂O) τ values: 2.62 (5H), 4.31 (1H), 4.51 – 4.69 (2H), 6.04 (1H), 6.20 – 6.90 (6H), 8.50 (3H), 8.60 (3H), 8.75 (6H), 8.90 (3H)

The above-mentioned operation was repeated, except that the 4-n-pentyl-2,3-dioxo-1-piperazinocarbonyl chloride was replaced by each of the reactive derivatives of compounds of formula (III) shown in Table 14, to obtain respective objective compounds as shown in Table 14. The structure of ech objective compound was confirmed by IR and NMR.

Table 14

| Reactive derivative of compound of formula (III) | Objective compound |
|---|---|
| 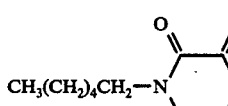 CH₃(CH₂)₄CH₂—N⟩N—COCl | D(—)—  CH₃(CH₂)₄CH₂—N⟩N—CONHCHCONH—[penicillin]—COOH<br>m.p. (decomp.) 107° C, yield 89 % |

Table 14-continued

| Reactive derivative of compound of formula (III) | Objective compound |
|---|---|
| $CH_3(CH_2)_5CH_2-N\text{-piperazinedione}-N-COCl$ | D(−)− $CH_3(CH_2)_5CH_2-N\text{-piperazinedione}-N-CONHCHCONH-$ penicillanic (phenyl) m.p. (decomp.) 92° C, yield 88.5 % |
| $CH_3(CH_2)_6CH_2-N\text{-piperazinedione}-N-COCl$ | D(−)− $CH_3(CH_2)_6CH_2-N\text{-piperazinedione}-N-CONHCHCONH-$ penicillanic (phenyl) m.p. (decomp.) 95° C, yield 79.8 % |
| $CH_3CH_2-N\text{-piperazinedione}-N-CSCl$ | D(−)− $CH_3CH_2-N\text{-piperazinedione}-N-CSNHCHCONH-$ penicillanic (phenyl) m.p. (decomp.) 80–82° C, yield 95 % |

EXAMPLE 13

Using 1.7 g of a triethylamine salt of 6-[D(−)-α-amino-p-hydroxyphenylacetamido]penicillanic acid and 0.7 g of 4-methyl-2,3-dioxo-1-piperazinocarbonyl chloride, the same operation as in Example 12 was repeated to obtain 1.2 g of a sodium salt of 6-[D(−)-α-(4-methyl-2,3-dioxo-1-piperazinocarbonylamino)-p-hydroxyphenylacetamido]penicillanic acid, m.p. 170°–172° C (decomp.), yield 75%.

IR (KBr) cm$^{-1}$: $\nu_{C=O}$ 1760 (lactam), 1710 − 1660 (—CON<), 1600 (—COO$^{\ominus}$)

NMR ((CD$_3$)$_2$SO) τ values: 2.8 − 3.3 (4H), 4.45 (1H), 4.65 (2H), 6.05 (1H), 6.2 (4H), 6.97 (3H), 8.48 (3H), 8.60 (3H)

In the same manner as above, a sodium salt of 6-[D(−)-α-(4-ethyl-2,3-dioxo-1-piperazinocarbonylamino)-p-hydroxyphenylacetamido]penicillanic acid, m.p. 175° C (decomp.), yield 72%, was obtained from 4-ethyl-2,3-dioxo-1-piperazinocarbonyl chloride and a triethylamine salt of 6-[D(−)-α-amino-p-hydroxyphenylacetamido]penicillanic acid.

EXAMPLE 14

To a solution of 0.8 g of a phthalide ester of 6-[D(−)-α-aminophenylacetamido]penicillanic acid in 10 ml of tetrahydrofuran was added 0.25 ml of triethylamine. Into the resulting mixture was dropped 0.32 g of 4-methyl-2,3-dioxo-1-piperazinocarbonyl chloride with ice-cooling, and the mixture was reacted at room temperature for 2 hours. After the reaction, the solvent was removed by distillation under reduced pressure. The residue was dissolved in a mixed solvent comprising 20 ml of ethyl acetate and 20 ml of water, and the resulting solution was adjusted to a pH of 2 by addition of dilute hydrochloric acid. Subsequently, the organic layer was separated off, washed with water, washed with a 2% aqueous sodium hydrogencarbonate solution, washed with water, dried over magnesium sulfate, and then concentrated to a liquid amount of about 2 ml. To the concentrate was added 20 ml of diisopropyl ether to deposit crystals, which were then collected to obtain 0.95 g of crystals of a phthalide ester of 6-[D(−)-α-(4-methyl-2,3-dioxo-1-piperazinocarbonylamino)-phenylacetamido]penicillanic acid, m.p. 157° − 160° (decomp.), yield 90.0%.

IR (KBr) cm$^{-1}$: $\nu_{C=O}$ 1780 (lactam), 1715 (ester), 1680 (—CON<)

NMR ((CD$_3$)$_2$CO + D$_2$O) τ values: 2.12 (4H), 2.40 (1H), 2.58 (5H), 4.25 − 4.60 (3H), 5.45 (1H), 5.85 − 6.42 (4H), 6.90 (3H), 8.50 (6H)

The above-mentioned operation was repeated, except that the 4-methyl-2,3-dioxo-1-piperazinocarbonyl chloride was replaced by each of the reactive derivatives of compounds of formula (III) shown in Table 15, to obtain respective objective compounds as shown in Table 15. The structure of each objective compound was confirmed by IR and NMR.

Table 15

| Reactive derivative of compound of formula (III) | Objective compound |
|---|---|
| $CH_3CH_2-N\text{-piperazinedione}-N-COCl$ | D(−)− $CH_3CH_2-N\text{-piperazinedione}-N-CONHCHCONH-$ penicillanic phthalide ester m.p. (decomp.) 108–110° C, yield 90 % |

Table 15-continued

| Reactive derivative of compound of formula (III) | Objective compound |
|---|---|
| (CH₃)₂CH—N(C=O)(C=O)N—COCl [4-isopropyl-2,3-dioxo-1-piperazinocarbonyl chloride] | D(−)− (CH₃)₂CH—N(C=O)(C=O)N—CONHCHCONH-[penicillin with phthalidyl ester], phenyl side chain; m.p. (decomp.) 128–130° C, yield 92 % |
| CH₃(CH₂)₂CH₂—N(C=O)(C=O)N—COCl | D(−)− CH₃(CH₂)₂CH₂—N(C=O)(C=O)N—CONHCHCONH-[penicillin with phthalidyl ester], phenyl side chain; m.p. (decomp.) 113–115° C, yield 88 % |

EXAMPLE 15

A solution of 0.86 g of a hydrochloride of methoxymethyl ester of 6[D(−)-α-aminophenylacetamido]-penicillanic acid in 15 ml of tetrahydrofuran containing 20 % by volume of water was adjusted to a pH of 8.0 to 8.5 by addition of triethylamine at 0° to 5° C. Into this solution, a solution of 0.38 g of 4-methyl-2,3-dioxo-1-piperazinocarbonyl chloride in 10 ml of tetrahydrofuran was dropped over a period of 10 minutes. During this period, the pH of the reaction solution was maintained at 7.5 to 8.0 by gradual addition of triethylamine. The resulting mixed solution was reacted for 30 minutes, while maintaining the pH thereof at 7.5 to 8.0. After completion of the reaction, the tetrahydrofuran was removed by distillation under reduced pressure. The residue was dissolved in a mixed solvent comprising 50 ml of water and 50 ml of ethyl acetate, and the resulting solution was adjusted to a pH of 1.5 by addition of dilute hydrochloric acid with ice-cooling. Subsequently, the organic layer was separated off, washed with water, dried over anhydrous magnesium sulfate, and then freed from the solvent by distillation under reduced pressure to form crystals. The thus formed crystals were washed with diethyl ether to obtain 0.9 g of a methoxymethyl ester of 6-[D(−)-α-(4-methyl-2,3-dioxo-1-piperazinocarbonylamino)-phenylacetamido]penicillanic acid, m.p. 111° – 115° C (decomp.), yield 82.5%.

IR (KBr) cm⁻¹: $\nu_{C=O}$ 1780 (lactam), 1740 (ester), 1700 – 1660 (—CON<)

NMR ((CD₃)₂CO) τ values: 0.15 (1H), 2.0 (1H), 2.67 (5H), 4.3 – 4.5 (3H), 4.75 (2H), 5.7 (1H), 6.55 (4H), 6.97 (3H), 7.25 (3H), 8.84 (3H), 8.60 (3H).

The above-mentioned operation was repeated, except that the 4-methyl-2,3-dioxo-1-piperazinocarbonyl chloride was replaced by each of the reactive derivatives of compounds of formula (III) shown in Table 16, to obtain respective objective compounds as shown in Table 16. The structure of each objective compound was confirmed by IR and NMR.

Table 16

| Reactive derivative of compound of formula (III) | Objective compound |
|---|---|
| CH₃CH₂—N(C=O)(C=O)N—COCl | D(−)− CH₃CH₂—N(C=O)(C=O)N—CONHCHCONH-[penicillanate methoxymethyl ester], phenyl side chain; m.p. (decomp.) 83–85° C, yield 80.2 % |
| CH₃(CH₂)₂CH₂—N(C=O)(C=O)N—COCl | D(−)− CH₃(CH₂)₂CH₂—N(C=O)(C=O)N—CONHCHCONH-[penicillanate methoxymethyl ester], phenyl side chain; m.p. (decomp.) 78–80° C, yield 80 % |
| (CH₃)₂CH—N(C=O)(C=O)N—COCl | D(−)− (CH₃)₂CH—N(C=O)(C=O)N—CONHCHCONH-[penicillanate methoxymethyl ester], phenyl side chain; m.p. (decomp.) 93–95° C, yield 82.5 % |

Table 16-continued

| Reactive derivative of compound of formula (III) | Objective compound |
|---|---|
| 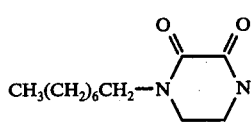 | 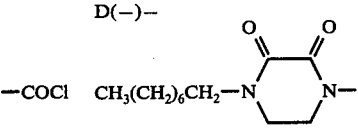 m.p. (decomp.) 70–74° C, yield 74.4 % |

EXAMPLE 16

Using 1.5 g of a hydrochloride of pivaloyloxymethyl ester of 6-[D(—)-α-aminophenylacetamido]-penicillanic acid and 0.6 g of 4-methyl-2,3-dioxo-1-piperazinocarbonyl chloride, the same operation as in Example 15 was repeated to obtain a pivaloyloxymethyl ester of 6-[D(—)-α-(4-methyl-2,3-dioxo-1-piperazinocarbonylamino)phenylacetamido]penicillanic acid, m.p. 108° – 111° C (decomp.), yield 75%.

IR (KBr) cm$^{-1}$: $\nu_{C=O}$ 1780 (lactam), 1750 (ester), 1710 – 1660 (—CON<)

The above-mentioned operation was repeated, except that the 4-methyl-2,3-dioxo-1-piperazinocarbonyl chloride was replaced by each of the reactive derivatives of compounds of formula (III) shown in Table 17, to obtain respective objective compounds as shown in Table 17. The structure of each objective compound was confirmed by IR and NMR.

ride was replaced by 4-n-octyl-2,3-dioxo-1-piperazinocarbonyl chloride, to obtain a β-piperidino ethyl ester of 6-[D(—)-α-(4-n-octyl-2,3-dioxo-1-piperazinocarbonylamino)phenylacetamido]penicillanic acid, m.p. 110° – 115° C (decomp.), yield 73.58%.

EXAMPLE 18

Using 0.93 g of a hydrochloride of β-morpholinoethyl ester of 6-[D(—)-α-aminophenylacetamido]penicillanic acid and 0.39 g of 4-methyl-2,3-dioxo-1-piperazinocarbonyl chloride, the same operation as in Example 15 was repeated to obtain 0.8 g of a β-morpholinoethyl ester of 6-[D(—)-α-(4-methyl2,3-dioxo-1-piperazinocarbonylamino)phenylacetamido]-penicillanic acid, m.p. 150° –153° C (decomp.), yield 73%.

IR (KBr) cm$^{-1}$: $\nu_{C=O}$ 1780 (lactam), 1740 (ester), 1710 – 1680 (—CON<)

NMR (CDCl$_3$) τ values: 2.55 (5H), 4.3 – 4.55 (3H), 5.6 (1H), 5.7 (3H), 6.0 (2H), 6.3 (2H), 7.4 (2H), 7.5 (4H), 8.5 (6H)

Table 17

| Reactive derivative of compound of formula (III) | Objective compound |
|---|---|
| 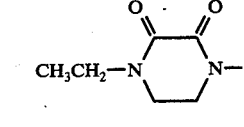 | 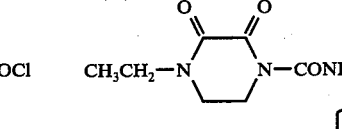 m.p. (decomp.) 94–98° C, yield 77 % |
| 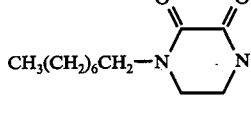 | 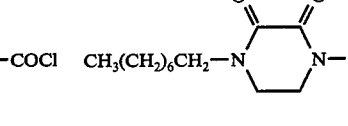 m.p. (decomp.) 72–75° C, yield 72 % |

EXAMPLE 17

Using 0.81 g of a hydrochloride of β-piperidinoethyl ester of 6-[D(—)-α-aminophenylacetamido]penicillanic acid and 0.3 g of 4 methyl2,3-dioxo-1-piperazinocarbonyl chloride, the same operation as in Example 15 was repeated to obtain 0.75 g of a β-piperidinoethyl ester of 6-[D(—)-α-(4-methyl-2,3dioxo-1-piperazinocarbonylamino)phenylacetamido]penicillanic acid, m.p. 166° –169° C (decomp.), yield 78 %.

IR (KBr) cm$^{-1}$: $\nu_{C=O}$ 1780 (lactam), 1740 (ester), 1710 –1670 (—CON<)

NMR (CDCl$_3$) τvalues: 2.7 (5H), 4.3 – 4.6 (3H), 5.7 (1H), 5.75 (2H), 6.0 (2H), 6.4 (2H), 6.9 (3H), 7.45 (2H), 7.6 (4H), 8.5 (12H)

The above-mentioned operation was repeated, except that the 4-methyl-2,3-dioxo-1-piperazinocarbonyl chloride was replaced by 4-n-octyl-2,3-dioxo1-piperazinocarbonyl chloride, to obtain a β-morpholinoethyl ester of 6-[D(—)-α-(4n-octyl-2,3-dioxo-1-piperazinocarbonylamino)phenylacetamido]penicillanic acid, m.p. 103° – 105° C (decomp.), yield 70%.

EXAMPLE 19

(1) To a solution of 8.7 g of a sodium salt of D(—)-α-phenylglycine in 50 ml of water were added 50 ml of ethyl acetate and 5.05 g of triethylamine. To the resulting mixture was gradually added 9.5 g of 4-methyl-2,3-dioxo-1-piperazinocarbonyl chloride at 0° to 5° C over a period of 15 minutes, and then the mixture was reacted at 5° to 15° C for 30 minutes. After the reaction, the aqueous layer was separated off, washed with diethyl ether, and then adjusted to a pH of 1.5 by addition of dilute hydrochloric acid to deposit crystals. The deposited crystals were collected by filtration, washed with water and dried to obtain 14.1 g of D(—)-α-(4-methyl-2,3-dioxo-1-piperazinocarbonylamino)phenylacetic acid, m.p. 138°–141° C (decomp.), yield 87%. Recrystallization from hydrous butanol gave white crystals, m.p. 140° –142° C (decomp.).

Elementary analysis (for $C_{14}H_{15}N_3O_5 \cdot H_2O$):
Calculated (%) C: 52.01; H: 5.30; N: 13.00.
Found (%) C: 52.24; H: 5.32; N: 12.87.
IR (KBr) cm$^{-1}$: $\nu_{C=O}$ 1710, 1700, 1660

(2) Into a solution of 10 g of the above-mentioned D(-)-α-(4-methyl-2,3-dioxo-1-piperazinocarbonylamino)-phenylacetic acid in 200 ml of acetone was dropped a solution of 5.2 g of a sodium salt of 2-ethylhexanoic acid of 50 ml of acetone with stirring to deposit crystals. The deposited crystals were collected by filtration and then washed with acetone to obtain 9.6 g of a sodium salt of D(—)-α-(4-methyl-2,3-dioxo-1-piperazinocarbonylamino)-phenylacetic acid, m.p. 165° C (decomp.), yield 95%.

(3) To a suspension of 8.8 g of the abovementioned sodium salt of D(—)-α-(4-methyl-2,3-dioxo-1-piperazinocarbonylamino)phenylacetic acid in 80 ml of methylene chloride was added 20 mg of N-methylmorpholine. Into the resulting mixture was dropped a solution of 3.1 g of ethyl chlorocarbonate in 20 ml of methylene chloride at —20° to —15° C over a period of 5 minutes, and the mixture was reacted at said temperature for 1 hour. Into this reaction liquid was dropped a solution of 9.4 g of a triethylamine salt of 6-aminopenicillanic acid in 40 ml of methylene chloride at —40° to —30° C over a period of 10 minutes. and the resulting mixture was reacted at —40° to —20° C over a period of 1 hour. After the reaction, the temperature of the reaction liquid was gradually elevated to 0° C over a period of 1 hour, and the mixture was then subjected to extraction with 100 ml of water. Subsequently, the aqueous layer was separated off, and the methylene chloride layer was further subjected to extraction with 50 ml of water, and the resulting aqueous layer was combined with the aforesaid aqueous layer. The combined aqueous layer was adjusted to a pH of 2 by addition of dilute hydrochloric acid with ice-cooling to deposit crystals. The deposited crystals were collected by filtration, sufficiently washed with water, dried and then dissolved in 200 ml of acetone. Into the resulting solution was dropped a solution of 4 g of a sodium salt of 2-ethylhexanoic acid in 40 ml of acetone over a period of 10 minutes to deposit crystals. The deposited crystals were collected by filtration, washed with acetone and then dried to obtain 11.4 g of a sodium salt of 6-[D(—)-α-(4-methyl-2,3-dioxo-1-piperazinocarbonylamino)phenylacetamido]penicillanic acid, m.p. 170° C (decomp.), yield 80.8%.

The above-mentioned operation was repeated, except that the D(—)-α-(4-methyl-2,3-dioxo-1-piperazinocarbonylamino)phenylacetic acid was replaced by each of the compounds of formula (V) shown in Table 18, to obtain respective objective compounds as shown in Table 18. The structure of each objective compound was confirmed by IR and NMR.

Table 18

| Compound of formula (V) | Objective compound |
|---|---|
| 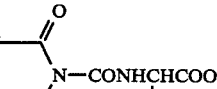 |  |
| 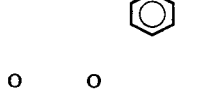 | 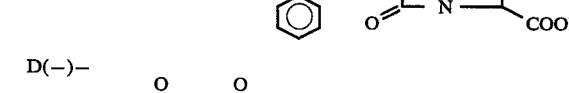 |
| 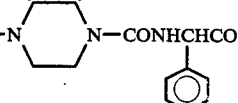 | 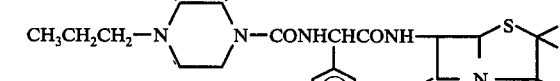 |

EXAMPLE 20

(1) To a solution of 2.28 g of D(—)-α-amino1,4-cyclohexadienylacetic acid in 15 ml of N NaOH were added 20 ml of ethyl acetate and 2.1 ml of triethylamine, and the resulting mixture was cooled to 0° C. To thic mixture was gradually added 1.69 g of 4-methyl-2,3-dioxo-1-piperazinocarbonyl chloride over a period of 10 minutes. Subsequently, the mixture was reacted for 30 minutes with ice-cooling, and then the aqueous layer was separated off. To the aqueous layer was further added 20 ml of ethyl acetate. The resulting mixture was adjusted to a pH of 2 by addition of 2N hydrochloric acid with ice-cooling, and the ethyl acetate layer was separated off. The organic layer was sufficiently washed with water, dried over anhydrous magnesium sulfate, freed from the solvent by distillation under reduced pressure and then incorporated with isopropyl alcohol to deposit crystals. The deposited crystals were collected by filtration to obtain 2.5 g of white crystals of D(—)-α-(4-methyl-2,3-dioxo-1-piperazinocarbonylamino)-1,4-cyclohexadienylacetic acid, m.p. 140°-145° C (decomp.), yield 74%.

IR (KBr) cm$^{-1}$: $\nu_{NH}$ 3300, $\nu_{C=O}$ 1715, 1660

NMR(d$_6$-DMSO) τ values: 0.57 (1H, d), 4.26 (1H, s), 4.36 (2H, s), 5.29 (1H, d), 6.07 - 6.18 (2H, m), 6.38 - 6.49 (2H, m), 7.05 (3H, s), 7.35 (4H,s)

(2) To a suspension of 0.45 g of the above-mentioned D(—)-α-(4-methyl-2,3-dioxo-1-piperazinocarbonylamino)-1,4-cyclohexadienylacetic acid in 15 ml of anhydrous methylene chloride was added 0.24 ml of N-methylmorpholine with stirring to form a solution.

(1H, d), 5.75 (1H, s), 6.05 (2H, bs), 6.40 (2H, bs), 7.03 (3H, s), 7.35 (4H, s), 8.40 (3H, s), 8.52 (3H, s)

The thus obtained product was adjusted to a pH of 7.0 by neutralization with an aqueous sodium hydrogencarbonate solution, and then subjected to filtration and freeze-drying to obtain a sodium salt thereof.

The above-mentioned operation was repeated, except that the D(—)-α-(4-methyl-2,3-dioxo-1-piperazinocarbonylamino)-1,4-cyclohexadienylacetic acid was replaced by each of the compounds of formula (V) shown in Table 19, to obtain respective objective compounds as shown in Table 19. The structure of each objective compound was confirmed by IR and NMR.

Table 19

| Compound of formula (V) | Objective compound |
|---|---|
| D(—)- CH$_3$CH$_2$—N(piperazinedione)N—CONHCHCOOH (phenyl) | D(—)- CH$_3$CH$_2$—N(piperazinedione)N—CONHCHCONH—(penicillin-S-CH$_3$/CH$_3$/COONa) (phenyl) |
| D(—)- CH$_3$CH$_2$CH$_2$—N(piperazinedione)N—CONHCHCOOH (phenyl) | D(—)- CH$_3$CH$_2$CH$_2$—N(piperazinedione)N—CONHCHCONH—(penicillin-S-CH$_3$/CH$_3$/COONa) (phenyl) |
| D(—)- CH$_3$(CH$_2$)$_2$CH$_2$—N(piperazinedione)N—CONHCHCOOH (phenyl) | D(—)- CH$_3$(CH$_2$)$_2$CH$_2$—N(piperazinedione)N—CONHCHCONH—(penicillin-S-CH$_3$/CH$_3$/COONa) (phenyl) |

After cooling the solution of —10° C, 3 ml of an anhydrous methylene chloride solution containing 0.24 g of ethyl chlorocarbonate was dropped into the solution, and the resulting mixture was reacted at said temperature for 90 minutes. Subsequently, the reaction liquid was cooled to —20° C, and 5 ml of a methylene chloride solution containing 0.70 g of a triethylamine salt of 6-aminopenicillanic acid and 0.31 ml of triethylamine was gradually dropped into the reaction liquid. The resulting mixture was reacted at —20° C for 1 hour, at —20° to 0° C for 1 hour, and at 0° to 5°0 C for 1 hour. Thereafter, the reaction liquid was freed from the solvent by distillation under reduced pressure. The residue was dissolved in 10 ml of water and then washed with 10 ml of ethyl acetate. The aqueous layer was again incorporated with 15 ml of ethyl acetate, and then adjusted to a pH of 2.0 by addition of 2N HCl with ice-cooling. Subsequently, the ethyl acetate layer was separated off, washed with water, dried over anhydrous magnesium sulfate, and freed from the solvent by distillation under reduced pressure to obtain 0.74 g of white crystals of 6-[D(—)-α-(4-methyl-2,3-dioxo-1-piperazinocarbonylamino)-1,4-cyclohexadienylacetamido]penicillanic acid, m.p. 84° -87° C (decomp.), yield 87%.

IR (KBr) cm$^{-1}$: $\nu_{C=O}$ 1780 (lactam), 1730 - 1660 (—COOH, —CON<)

NMR (d$_6$-DMSO) τ values: 0.55 (1H, d), 0.95 (1H, d), 4.22 (1H, s), 4.35 (2H, s), 4.41 - 4.61 (2H, s), 4.92

EXAMPLE 21

(1) To a solution of 2.2 g of DL-α-amino-2-thienylacetic acid in 14 ml of a N sodium hydroxide solution was added at 0° C 2.2 g of triethylamine. To the resulting mixture was further added 3.6 g of 4-methyl-2,3-dioxo-1-piperazinocarbonyl chloride little by little at said temperature. Subsequently, the mixture was reacted at 0° C for 30 minutes, and then at room temperature for 30 minutes. After the reaction, the reaction liquid was adjusted to a pH of 1.0 by addition of dilute hydrochloric acid to deposit crystals. The deposited crystals were collected by filtration, washed with water and then dried to obtain 3.5 g of DL-α-(4-methyl-2,3-dioxo-1-piperazinocarbonylamino)-2-thienylacetic acid, m.p. 214° - 215° C (decomp.), yield 80.5%.

IR (KBr) cm$^{-1}$: $\nu_{C=O}$ 1710, 1680 — 1660

(2) Into a solution of 3.5 g of the abovementioned DL-α-(4-methyl-2,3-dioxo-1-piperazinocarbonylamino)-2-thienylacetic acid in 100 ml of acetone was dropped a solution of 1.86 g of a sodium salt of 2-ethylhexanoic acid in 50 ml of acetone, upon which crystals were deposited. The deposited crystals were collected by filtration and then washed with acetone to obtain 3.5 g of a sodium salt of DL-α-(4-methyl-2,3-dioxo-1-piperazinocarbonylamino)-2-thienylacetic acid, m.p. 175° - 176° C (decomp.).

(3) To a suspension of 3.3 g of the abovementioned sodium salt of DL-α-(4-methyl-2,3-dioxo1-piperazinocarbonylamino)-2-thienylacetic acid in 50 ml of methylene chloride was added 30 mg of Nmethylmorpholine, and the resulting mixture was then cooled to −20° to −15° C. Into the resulting mixture was dropped a solution of 1.3 g of ethyl chlorocarbonate in 20 ml of methylene chloride over a period of 5 minutes, and the mixture was stirred at said temperature for 90 minutes. Subsequently, a solution of 3.3 g of a triethylamine salt of 6aminopenicillanic acid in 50 ml of methylene chloride was dropped into the mixture at −50° to −40° C over a period of 20 minutes, and the resulting mixture was reacted with stirring at −40° to −30° C for 30 minutes, at −30° to −20° C for 30 minutes, and then at −20° to 0° C for 30 minutes. After the reaction, the solvent was removed by distillation under reduced pressure, and the residue was dissolved in water. The resulting aqueous solution was adjusted to a pH of 2.0 by addition of dilute hydrochloric acid with ice-cooling to deposit crystals. The deposited crystals were collected by filtration, sufficiently washed with water and then dried to obtain 4.1 g of 6-[DL-α-(4-methyl-2,3-dioxo-1-piperazinocarbonylamino)-2-thienylacetamido]penicillanic acid, m.p. 185° C (decomp.), yield 80.5%.

IR (nujol) cm$^{-1}$: $\nu_{C=O}$ 1780 (lactam), 1715 (—COOH), 1685 − 1675 (—CON<)

NMR ((CD$_3$)$_2$CO) τ values: 0.5 (1H), 1.8 (1H), 2.6 (1H), 2.85 − 3.05 (2H), 4.0 (1H), 4.2 − 4.5 (2H), 5.7 (1H), 5.8 − 6.0 (2H), 6.2 − 6.4 (2H), 6.95 (3H), 8.4 (3H), 8.45 (3H)

The thus obtained product was adjusted to a pH of 7.0 by neutralization with an aqueous sodium hydrogencarbonate solution, and then subjected to filtration and freeze-drying to obtain a sodium salt thereof.

The above-mentioned operation was repeated, except that the sodium salt of DL-α-(4-methyl-2,3-dioxo-1-piperazinocarbonylamino)-2-thienylacetic acid was replaced by each of the compounds of formula (V) shown in table 20, to obtain respective objective compounds as shown in Table 20. The structure of each objective compound was confirmed by IR and NMR.

EXAMPLE 22

To a suspension of 0.9 g of 6-[D(−)-α-aminophenylacetamido]penicillanic acid in 30 ml of anhydrous ethyl acetate were added at 5° to 10° C 0.55 g of triethylamine and 0.6 g of trimethylsilyl chloride. The resulting mixture was reacted at 15° to 20° C for 3 hours to form trimethylsilylated 6-[D (−)-α-aminophenylacetamido]penicillanic acid. To this acid was then added 1 g of 4-ethyl-2,3-dioxo-1-piperazinocarbonyl chloride, and the resulting mixture was reacted at 15° to 20° C for 2 hours. After the reaction, a deposited triethylamine hydrochloride was separated by filtration, and the filtrate was incorporated with 0.4 g of n-butanol to deposit crystals. The deposited crystals were collected by filtration to obtain 1.25 g of white crystals of 6-[D(−)-α-(4-ethyl-2,3-dioxo1-periperzinocarbonylamino)phenylacetamido]penicillanic acid. Into a solution of said crystals in 30 ml of tetrahydrofuran was dropped a solution of 0.38 g of a sodium salt of 2-ethylhexanoic acid in 10 ml of tetrahydrofuran, upon which white crystals were deposited. The deposited crystals were collected by filtration, sufficiently washed with tetrahydrofuran and then dried to obtain 1.25 g of a sodium salt of 6-[D(−)-α-(4-ethyl-2,3-dioxo-1-piperazinocarbonylamino)phenylacetamido]penicillanic acid, m.p. 183°–185° C (decomp.), yield 90%.

EXAMPLE 23

To a suspension of 4 g of a trihydrate of 6-[D(−)-α-aminophenylacetamido]penicillanic acid in 40 ml of water was added 20 ml of ethyl acetate, and the resulting mixture was cooled to 2° C. Subsequently, the mixture was incorporated with 1.37 g of potassium carbonate, and then stirred at 2° to 3° C for 2 minutes. Thereafter, 1.89 g of 4-methyl-2,3-dioxo-1-piperazinocarbonyl chloride was added to the mixture at said temperature over a period of 10 minutes, and the resulting mixture was reacted at said temperature for 15 minutes. After the reaction, slight amounts of insolubles were sepa- Table 20

| Compound of formula (V) | Objective compound |
|---|---|
| DL— CH$_3$CH$_2$—N(piperazinedione)N—CONHCHCOONa (thienyl) | DL— CH$_3$CH$_2$—N(piperazinedione)N—CONHCHCONH—(penicillin, CH$_3$, CH$_3$, COONa) (thienyl) |
| DL— CH$_3$CH$_2$CH$_2$—N(piperazinedione)N—CONHCHCOONa (thienyl) | DL— CH$_3$CH$_2$CH$_2$—N(piperazinedione)N—CONHCHCONH—(penicillin, CH$_3$, CH$_3$, COONa) (thienyl) |
| DL— CH$_3$(CH$_2$)$_2$CH$_2$—N(piperazinedione)N—CONHCHCOONa (thienyl) | DL— CH$_3$(CH$_2$)$_2$CH$_2$—N(piperazinedione)N—CONHCHCONH—(penicillin, CH$_3$, CH$_3$, COONa) (thienyl) | rated by filtration, and the filtrate was charged into 80 ml of ethyl acetate. Into the resulting mixture was dropped 5 ml of 2N HCl at 20° to 22° C over a period of 5 minutes, and the mixture was stirred at said temperature for 5 hours to deposit crystals. The deposited crystals were collected by filtration, washed two times with 4 ml of water, further washed two times with 4 ml of isopropanol, and then dried to obtain 4.0 g of a dihydrate of 6-[D(—)-α-(4-methyl-2,3-dioxo-1-piperazinocarbonylamino)phenylacetamido]penicillanic acid, m.p. 156°–157° C (decomp.), yield 75.4%.

IR (KBr) cm$^{-1}$: $\nu_{C=O}$ 1775, 1740, 1695, 1670

NMR (d$_6$-DMSO) τ values: 0.18 (1H, d), 0.77 (1H, d), 2.66 (5H, s), 4.30 (1H, d), 4.40 (3H, br), 4.48 (1H, g), 4.65 (1H, d), 5.80 (1H, s), 6.12 (2H, bs), 6.45 (2H, bs), 7.06 (3H, s), 8.48 (3H, s), 8.60 (3H, s)

The above-mentioned operation was repeated, except that the 4-methyl-2,3-dioxo-1-piperazinocarbonyl chloride was replaced by 4-ethyl-2,3-dioxo-1-piperazinocarbonyl chloride, to obtain a monohydrate of 6-[D(—)-α-(4-ethyl-2,3-dioxo-1-piperazinocarbonylamino)-phenylacetamido]penicillanic acid, m.p. 154°–156° C (decomp.), yield 84.8%.

IR (KBr) cm$^{-1}$: $\nu_{C=O}$ 1775, 1735, 1705, 1680, 1665

NMR (d$_6$-DMSO) τ values: 0.20 (1H, d), 0.76 (1H, d), 2.69 (5H, s), 4.32 (1H, d), 4.53 (1H, q), 4.64 (1H, d), 5.00 (3H, br), 5.83 (1H, s), 6.13 (2H, bs), 6.49 (2H, bs), 6.62 (2H, q), 8.44 (3H, s), 8.58 (3H, s), 8.91 (3H, t)

The thus obtained monohydrate was neutralized with an aqueous sodium hydrogencarbonate solution, and then subjected to filtration and freeze-drying to obtain a sodium salt of 6-[D(—)-α-(4-ethyl-2,3-dioxo-1-piperazinocarbonylamino)phenylacetamido]penicillanic acid.

Further, a solution in 10 ml of nitromethane of 2 g of the aforesaid dihydrate of 6-[D(—)-α-(4-methyl-2,3-dioxo-1-piperazinocarbonylamino)phenylacetamido]-penicillanic acid was allowed to stand overnight to deposit crystals, which were then collected by filtration to obtain 2 g of a monohydrate of a nitromethane addition product of 6-[D(—)-α-(4methyl-2,3-dioxo-1-piperazinocarbonylamino)phenylacetamido]penicillanic acid, m.p. 128°–130° C (decomp.), yield 92.2%.

Elementary analysis (for C$_{22}$H$_{25}$N$_5$O$_7$S.CH$_3$NO$_2$.-H$_2$O): Calculated (%) C: 47.42; H: 5.19; N: 14.43. Found (%) C: 47.94; H: 5.13; N: 14.53.

IR (KBr) cm$^{-1}$: $\nu_{C=O}$ 1770, 1735, 1700, 1680

NMR (d$_6$-DMSO) τ values: 0.22 (1H, d), 0.80 (1H, d), 2.69 (5H, s), 3.30 (3H, br), 4.30 (1H, d), 4.46 – 4.70 (2H), 5.67 (3H, s), 5.81 (1H, s), 6.13 (2H, bs), 6.46 (2H, bs), 7.07 (3H, s), 8.45 (3H, s), 8.58 (3H, s)

EXAMPLE 24

To a suspension of 1.6 g of a trihydrate of D(—)-α-aminobenzyl penicillin in 20 ml of water was added at 2° to 3° C 0.54 g of potassium carbonate, and the resulting mixture was stirred for 3 minutes. To the mixture was gradually added 0.81 g of 4-ethyl-2,3-dioxo-1-piperazinocarbonyl chloride at said temperature over a period of 10 minutes, and the mixture was reacted for 15 minutes. After the reaction, slight amounts of insolubles formed were separated by filtration, and the filtrate was charged into 10 ml of methyl n-propyl ketone. Into the resulting mixture was dropped 1.98 ml of 2N HCl at 15° to 20° C over a period of 2 minutes, and the mixture was stirred at said temperature for 1 hour to deposit crystals. The deposited crystals were collected by filtration, washed two times with 2 ml of water, further washed two times with 2 ml of methyl n-propyl ketone, and then dried to obtain 1.7 g of a monohydrate of D(—)-α-(4-ethyl-2,3-dioxo-1-piperazinocarbonylamino)benzylpenicillin, m.p. 152°–154° C (decomp.), yield 80.2%.

The thus obtained product was neutralized with an aqueous sodium hydrogencarbonate solution, and then subjected to filtration and freeze-drying to obtain a sodium salt of the said product.

EXAMPLE 25

A suspension of 4.0 g of a monohydrate of 7-(D(—)-α-aminophenylacetamido]-3-methyl-Δ$^3$-cephem4-carboxylic acid in 60 ml of tetrahydrofuran containing 20% by volume of water was adjusted to a pH of 8.0 to 8.5 by gradual addition of triethylamine with stirring to form a solution, which was then cooled to 0° C. To this solution were gradually added 2.5 g of crystals of 4-methyl-2,3-dioxo-1-piperazinocarbonyl chloride over a period of 10 minutes. During this period, the pH of the reaction solution was maintained at 7.5 to 8.0 by gradual addition of triethylamine. Subsequently, the resulting mixture was reacted at 0° to 5° C for 15 minutes while maintaining the pH thereof at 7.5 to 8.0. After the reaction, the reaction liquid was stirred together with 60 ml of diethyl ether and 70 ml of water, and then the aqueous layer was separated off. The thus obtained aqueous layer was washed with 30 ml of ethyl acetate, cooled to 0° to 5° C, and then adjustd to a pH of 1.5 by addition of dilute hydrochloric acid to deposit white crystals. The deposited crystals were collected by filtration, sufficiently washed with water and then dried to obtain 4.7 g of white crystals of 7-[D(—)-α-(4-methyl-2,3-dioxo-1-piperazinocarbonylamino)phenylacetamido]-3-methyl-Δ$^3$-cephem-4-carboxylic acid, m.p. 185°–186° C (decomp.), yield 86%.

IR (KBr) cm$^{-1}$: $\nu_{C=O}$ 1770 — 1760 (lactam), 1720 — 1660 (—CON<, —COOH)

NMR (d$_6$-DMSO) τ values: 0.1 (1H, d), 0.56 (1H, d) 2.62 (5H, s), 4.26 – 4.37 (2H, dd), 5.05 (1H, d), 6.1 (2H, bs), 6.47 (2H, bs), 6.63 (2H, s), 7.05 (3H, s), 8.02 (3H, s)

The above-mentioned operation was repeated, except that the 4-methyl-2,3-dioxo-1-piperazinocarbonyl chloride was replaced by each of the reactive derivatives of compounds of formula (III) shown in Table 21, to obtain respective objective compounds as shown in Table 21. The structure of each objective compound was confirmed by IR and NMR.

Table 21

| Reactive derivative of compound of formula (III) | Objective compound |
|---|---|
| 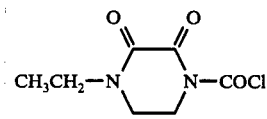 | D(−)− 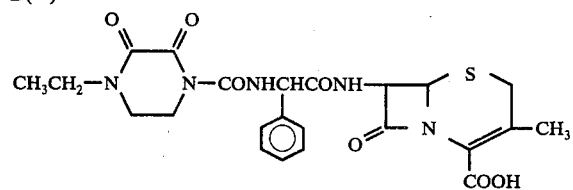<br>m.p. (decomp.) 168° C, yield 80 % |
| 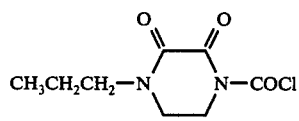 | D(−)− 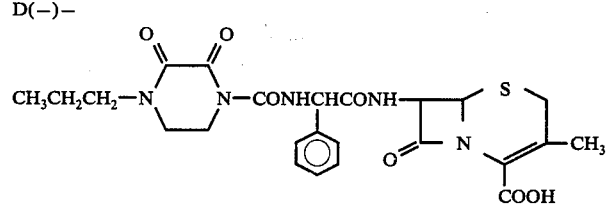<br>m.p. (decomp.) 160° C, yield 80.5 % |
| 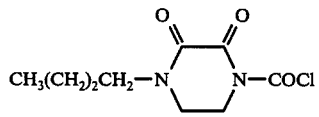 | 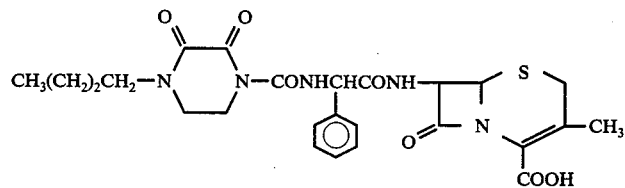<br>m.p. (decomp.) 150° C, yield 76 % |

EXAMPLE 26

(1) To a solution of 0.92 g of 1-n-pentyl-2,3-dioxo-piperazine in 15 ml of anhydrous dioxane were added 1.1 ml of triethylamine and 1.08 g of trimethylsilyl chloride. The resulting mixture was stirred at room temperature for 20 hours to form triethylamine hydrochloride. This hydrochloride was separated by filtration, and the filtrate was dropped at 0° to 5° C into a solution of 0.6 g of phosgene in 10 ml of anhydrous tetrahydrofuran. Subsequently, the resulting mixture was reacted at 5° to 10° C for 30 minutes and then at room temperature for 2 hours. Thereafter, the solvent was removed by distillation under reduced pressure to obtain 1.21 g of pale yellow, oily 4-n-pentyl-2,3-dioxo-1-piperazinocarbonyl chloride.

IR (film) cm$^{-1}$: $\nu_{C=O}$ 1790, 1720 − 1665

(2) A suspension of 1.70 g of a monohydrate of 7-[D(−)-α-aminophenylacetamido]-3-methyl-Δ$^3$-cephem4-carboxylic acid in 50 ml of tetrahydrofuran containing 20% by volume of water was adjusted to a ph of 8.0 to 8.5 by addition of triethylamine with stirring to form a solution. This solution was cooled to 0° to 5° C, and 7 ml of an anhydrous tetrahydrofuran solution containing 1.21 g of the 4-n-pentyl-2,3-dioxo-1-piperazinocarbonyl chloride obtained in (1) was dropped into the solution. During this period, the pH of the solution was maintained at a pH of 7.5 to 8.0 by addition of triethylamine. Subsequently, the resulting mixed solution was reacted at 0° to 5° C for 1 hour and then at 5° to 10° C for 2 hours while maintaining the pH thereof at 7.5 to 8.0. After the reaction, the tetrahydrofuran was removed by distillation under reduced pressure, and the residue was dissolved in 20 ml of water and then washed two times with 20 ml of ethyl acetate. The aqueous layer was again charged with 40 ml of ethyl acetate, and then adjusted to a pH of 1.5 by gradual addition of dilute hydrochloric acid with ice-cooling. Subsequently, the ethyl acetate layer was separated off, washed with water, and then dried over anhydrous magnesium sulfate. Thereafter, 10 ml of an ethyl acetate solution containing 0.75 g of sodium 2-ethylhexanoate was dropped into the layer at 0° to 5° C to deposit white crystals. The deposited crystals were collected by filtration, and washed with ethyl acetate and then with diethyl ether to obtain 1.95 g of a sodium salt of 7[D(−)-α-(4-n-pentyl-2,3-dioxo-1-piperazinocarbonylamino)-phenylacetamido]-3-methyl-Δ$^3$-cephem-4-carboxylic acid, m.p. 164°−166° C (decomp.), yield 75%.

IR (KBr) cm$^{-1}$: $\nu_{C=O}$ 1750 (lactam), 1720 − 1660 (—CON<), 1590 (—COO$^\ominus$)

NMR (d$_6$-DMSO + D$_2$O) τ values: 2.58 (5H, s), 4.33 (1H, s), 4.49 (1H, d), 5.17 (1H, d), 6.10 (2H, bs), 6.42 − 6.87 (6H, m), 8.09 (3H, s), 8.60 − 8.90 (6H, bs), 9.12 (3H, t)

The above-mentioned operation was repeated, except that the 4-n-pentyl-2,3-dioxo-1-piperazinocarbonyl chloride was replaced by each of the reactive derivatives of compounds of formula (III) shown in Table 22, to obtain respective objective compounds as shown in Table 22. The structure of each objective compound was confirmed by IR and NMR.

Table 22

| Reactive derivative of compound of formula (III) | Objective compound |
|---|---|
| 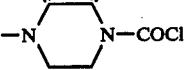 | D(−)−<br>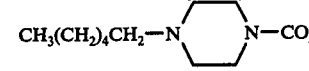<br>m.p. (decomp.) 160° C, yield 77.7 % |
| 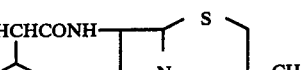 | D(−)−<br>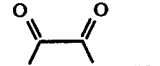<br>m.p. (decomp.) 158° C, yield 78 % |
| 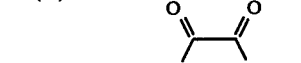 | D(−)−<br><br>m.p. (decomp.) 154° C, yield 78 % |
| 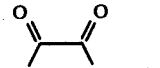 | D(−)−<br>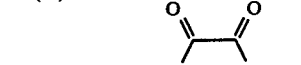<br>m.p. (decomp.) 185 – 188° C, yield 77% |
|  | D(−)−<br>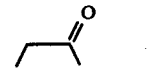<br>m.p. (decomp.) 135 – 137° C, yield 79.2 % |

EXAMPLE 27

Using 1.5 g of a hydrochloride of methoxymethyl ester of 7-[D(−)-α-aminophenylacetamido]-3-methyl-Δ³-cephem-4-carboxylic acid and 0.65 g of 4-methyl-2,3-dioxo-1-piperazinocarbonyl chloride, the same operation as in Example 25 was repeated to obtain 1.6 g of a methoxymethyl ester of 7-[D(−)-α-(4methyl-2,3-dioxo-1-piperazinocarbonylamino)phenylacetamido]-3-methyl-Δ³-cephem-4-carboxylic acid, m.p. 146°–148° C (decomp.), yield 86%.

IR (KBr) cm⁻¹: $\nu_{C=O}$ 1770 (lactam), 1710 (ester), 1680 − 1600 (—CON<)

EXAMPLE 28

To a suspension of 0.20 g of 7-[D(−)-αaminophenylacetamido]-3-acetoxymethyl-Δ³-cephem-4carboxylic acid in 15 ml of anhydrous chloroform was added 0.17 ml of triethylamine with stirring to form a solution, which was then cooled to 0° C. To this solution was added 0.11 g of 4-methyl-2,3-dioxo-1-piperazinocarbonyl chloride, and the resulting mixture was reacted at room temperature for 2 hours. After the reaction, the reaction liquid was evaporated under reduced pressure, and the residue was dissolved in 15 ml of water. The resulting solution was washed with 10 ml of ethyl acetate. The aqueous layer was again charged with 20 ml of ethyl acetate, and then adjusted to a pH of 1.5 by addition of 2N hydrochloric acid with ice-cooling. Subsequently, the ethyl acetate layer was separated off, successively washed with water and a saturated aqueous sodium chloride solution, and then dried over magnesium sulfate. Thereafter, the solvent as removed by distillation under reduced pressure to obtain 0.22 g of white crystals of 7-[D(−)-α-(4-methyl-2,3-dioxo-1-piperazinocarbonylamino)phenylacetamido]-3-acetoxymethyl-Δ³-cephem-4-carboxylic acid, m.p. 175° C (decomp.), yield 76%.

IR (KBr) cm⁻¹: $\nu_{C=O}$ 1770 (lactam), 1720 − 1650 (—CON<, —COOH)

NMR (d$_6$-DMSO) $\tau$ values:
0.23 (1H, d), 0.63 (1H, d), 2.66 (5H, s), 4.32 (1H, g), 4.43 (1H, d), 5.05 (1H, d), 5.21 (2H, q), 6.15 (2H, bs), 6.40 (2H, bs), 6.57 (2H, bs), 7.0 (3H, s), 8.0 (3H, s)

The above-mentioned operation was repeated, except that the 4-methyl-2,3-dioxo-1-piperazinocarbonyl chloride was replaced by each of the reactive derivatives of compounds of formula (III) shown in Table 23, to obtain respective objective compounds as shown in Table 23. The structure of each objective compound was confirmed by IR and NMR.

EXAMPLE 29

(1) To a solution of 28.2 g of a sodium salt of D(−)-phenylglycine in 150 ml of water were added 200 ml of ethyl acetate and 18.2 g of triethylamine, and the resulting mixture was cooled to 0° C. To this mixture was added 34.3 g of 4-methyl-2,3-dioxo-1-piperazinocarbonyl chloride over a period of 15 minutes, and the mixture was reacted at 5° to 10° C for 15 minutes. Thereafter, the aqueous layer was separated off and adjusted to a pH of 0.5 by addition of 2N hydrochloric acid with Table 23

| Reactive derivative of compound of formula (III) | Objective compound |
|---|---|
| CH$_3$CH$_2$CH$_2$—N(piperazinedione)—COCl | D(−)- CH$_3$CH$_2$CH$_2$—N(piperazinedione)—CONHCHCONH—(cephem with S, CH$_2$OCOCH$_3$, COOH, phenyl) <br> m.p. (decomp.) 150° C, yield 83.4 % |
| CH$_3$CH$_2$—N(piperazinedione)—COCl | D(−)- CH$_3$CH$_2$—N(piperazinedione)—CONHCHCONH—(cephem) <br> m.p. (decomp.) 165° C, yield 83 % |
| (CH$_3$)$_2$CH—N(piperazinedione)—COCl | D(−)- (CH$_3$)$_2$CH—N(piperazinedione)—CONHCHCONH—(cephem) <br> m.p. (decomp.) 146° C, yield 82 % |
| CH$_3$CH$_2$—N(piperazinedione)—CSCl | D(−)- CH$_3$CH$_2$—N(piperazinedione)—CSNHCHCONH—(cephem) <br> m.p. (decomp.) 112° C, yield 95 % |
| CH$_3$—N(piperazinedione)—CSCl | D(−)- CH$_3$—N(piperazinedione)—CSNHCHCONH—(cephem) <br> m.p. (decomp.) 134° C, yield 90.2 % |

The aforesaid 7-[D(−)-α-(4-methyl-2,3-dioxo-1-piperazinocarbonylamino)phenylacetamido]-3-acetoxymethyl-Δ$^3$-cephem-4-carboxylic acid, m.p. 175° C (decomp.), was recrystallized from hydrous acetone to obtain white crystals showing a melting point of 198° to 200° C (decomp.)

ice-cooling to deposit crystals. The deposited crystals were collected by filtration and then dried to obtain 42 g of white crystals of D(−)-α-(4-methyl-2,3-dioxo-1-piperazinocarbonylamino)phenylacetic acid, m.p. 195° C (decomp.).

IR (KBr) cm$^{-1}$: $\nu_{C=O}$ 1700, 1660

NMR (d$_6$-DMSO) $\tau$ values: 0.1 (1H, d), 2.65 (5H, s), 4.60 (1H, d), 6.10 (2H, bs), 6.50 (2H, bs), 7.0 (3H, s)

(2) To a suspension in 15 ml of anhydrous methylene chloride of 0.31 g of the D(—)-α-(4-methyl-2,3-dioxo-1-piperazinocarbonylamino)phenylacetic acid obtained in the above-mentioned item (1) was added 0.11 g of N-methylmorpholine with stirring to form a solution, which was then cooled to −20° C. To this solution was added 3 ml of an anhydrous methylene chloride solution containing 0.13 g of ethyl chlorocarbonate, and the resulting mixture was reacted at −10° to −20° C for 60 minutes to form a mixed acid anhydride. Into the thus formed acid anhydride was dropped a solution formed by adding 0.50 ml of triethylamine to a suspension in 5 ml of methanol of 0.41 g of 7-amino-3-[2-(5-methyl-1,3,4-thiadiazolyl)-thiomethyl]-Δ³-cephem-4-carboxylic acid. After the dropping, the resulting mixture was reacted at −50° to −30° C for 30 minutes, at −30° to −20° C for 30 minutes, at −20° to 0° C for 60 minutes, and then at room temperature for 30 minutes. Thereafter, the reaction liquid was concentrated under reduced pressure, and the concentrate was dissolved in 10 ml of water, washed with 5 ml of ethyl acetate, again charged with 15 ml of ethyl acetate, and then adjusted to a pH of 1.5 by addition of 2N hydrochloric acid with ice-cooling. Subsequently, insolubles were separated by filtration, and the ethyl acetate layer was separated off, successively washed with water and a saturated sodium chloride solution, dried over magnesium sulfate, and then freed from the solvent by distillation under reduced pressure to obtain 0.58 g of pale yellow crystals of 7-[D(—)-α-(4-methyl-2,3-dioxo-1-piperazinocarbonylamino)phenylacetamido]-3-[2-(5-methyl-1,3,4-thiadiazolyl)-thiomethyl]-Δ³-cephem-4-carboxylic acid, m.p. 160° C (decomp.), yield 91%.

IR (KBr) cm⁻¹: $\nu_{C=O}$ 1780 (lactam), 1650 - 1720 (—CON<, —COOH)

NMR (d₆-DMSO) τ values: 0.2 (1H, d), 0.6 (1H, d), 2.60 (5H, s), 4.35 (1H, q), 4.40 (1H, d), 5.0 (1H, d), 5.70 (2H, q), 6.10 (2H, bs), 6.25 - 6.55 (2H, 2H, bs), 7.0 (3H, s), 7.30 (3H, s)

The above-mentioned operation was repeated, except that the D(—)-α-(4-methyl-2,3-dioxo-1-piperazinocarbonylamino)phenylacetic acid was replaced by each of the compounds of formula (V) shown in Table 24, to obtain respective objective compounds as shown in Table 24. The structure of each objective compound was confirmed by IR and NMR.

Table 24

| Compound of formula (V) | Objective compound |
|---|---|
| D(—)-α-(4-ethyl-2,3-dioxo-1-piperazinocarbonylamino)phenylacetic acid (CH₃CH₂–piperazine) | Corresponding 7-acylamino cephem; m.p. (decomp.) 150° C, yield 91% |
| D(—)-α-(4-n-propyl-2,3-dioxo-1-piperazinocarbonylamino)phenylacetic acid (CH₃CH₂CH₂–piperazine) | Corresponding 7-acylamino cephem; m.p. (decomp.) 147° C, yield 85.4% |
| D(—)-α-(4-n-butyl-2,3-dioxo-1-piperazinocarbonylamino)phenylacetic acid (CH₃(CH₂)₂CH₂–piperazine) | Corresponding 7-acylamino cephem; m.p. (decomp.) 144° C, yield 84.3% |
| D(—)-α-(4-phenyl-2,3-dioxo-1-piperazinocarbonylamino)cyclohexylacetic acid | Corresponding 7-acylamino cephem; m.p. (decomp.) 167° C, yield 93% |

EXAMPLE 30

Using 0.3 g of D(—)-α-(4-methyl-2,3-dioxo-1-piperazinocarbonylamino)phenylacetic acid and 0.33 g of 7-amino-3-[5-(1-methyl-1,2,3,4-tetrazolyl)-thiomethyl]-Δ$^3$-cephem-4-carboxylic acid, the same operation as in Example 29 was repeated, to obtain 0.5 g of 7-[D(—)-α-(4-methyl-2,3-dioxo-1-piperazinocarbonylamino)phenylacetamido]-3-[5-(1-methyl-1,2,3,4-tetrazolyl)-thiomethyl]-Δ$^3$-cephem-4-carboxylic acid, m.p. 161° – 163° C (decomp.), yield 76%.

IR (nujol) cm$^{-1}$: $\nu_{C=O}$ 1775 (lactam), 1720 – 1660 (—CON<, —COOH)

NMR (d$_6$-DMSO) τ values: 0.02 (1H, d), 0.34 (1H, d), 2.48 (5H, s), 4.17 (1H, q), 4.26 (1H, d), 4.92 (1H, d), 5.66 (2H, s), 6.01 (5H, s), 6.35 (4H, s), 7.0 (3H, s)

The above-mentioned operation was repeated, except that the D(—)-α-(4-methyl-2,3-dioxo-1-piperazinocarbonylamino)phenylacetic acid was replaced by each of the compounds of formula (V) shown in Table 25, to obtain respective objective compounds as shown in Table 25. The structure of each objective compound was confirmed by IR and NMR.

EXAMPLE 31

Using 0.30 g of D(—)-α-(4-methyl-2,3-dioxo-1-piperazinocarbonylamino)phenylacetic acid and 0.34 g of 7-amino-3-[5-(1,3,4-thiadiazolyl)-thiomethyl]-Δ$^3$-cephem-4-carboxylic acid, the same operation as in Example 29 was repeated, to obtain 0.47 g of 7-[D(—)-α-(4-methyl-2,3-dioxo-1-piperazinocarbonylamino)phenylacetamido]-3-[5-(1,3,4-thiadiazolyl)-thiomethyl]-Δ$^3$-cephem-4-carboxylic acid, m.p. 158° – 159° C (decomp.), yield 71.5%.

IR (nujol) cm$^{-1}$: $\nu_{C=O}$ 1775 (lactam), 1720 – 1660 (—CON<, —COOH)

The above-mentioned operation was repeated, except that the D(—)-α-(4-methyl-2,3-dioxo-1-piperazinocarbonylamino)phenylacetic acid was replaced by D(—)-α-(4-ethyl-2,3-dioxo-1-piperazinocarbonylamino)phenylacetic acid, to obtain 7-[D(—)-α-(4-ethyl-2,3-dioxo-1-piperazinocarbonylamino)phenylacetamido]-3-[5-(1,3,4-thiadiazolyl)-thiomethyl]-Δ$^3$-cephem-4-carboxylic acid, m.p. 123° C (decomp.), yield 64.5%.

EXAMPLE 32

Using 0.31 g of D(—)-α-(4-methyl-2,3-dioxo-1-piperazinocarbonylamino)phenylacetic acid and 0.39 g of 7-amino-3-[2-(1-methyl-1,3,4-triazolyl)-thiomethyl]-Δ$^3$-cephem-4-carboxylic acid, the same operation as in Example 29 was repeated, except that the methanol was replaced by anhydrous methylene chloride, to obtain 0.43 g of 7-[D(—)-α-(4-methyl-2,3-dioxo-1-piperazinocarbonylamino)phenylacetamido]-3-[2-(1-methyl-1,3,4-triazolyl)-thiomethyl]-Δ$^3$-cephem-4-carboxylic acid, yield 70%.

Table 25

| Compound of formula (V) | Objective compound |
|---|---|
| D(—)-, CH$_3$CH$_2$-piperazinedione-CH$_3$-CONHCHCOOH-phenyl | D(—)-, CH$_3$CH$_2$-piperazinedione-CH$_3$-CONHCHCONH-phenyl-cephem-CH$_2$S-(1-methyl-tetrazolyl); m.p. (decomp.) 170° C, yield 63.6 % |
| D(—)-, CH$_3$-piperazinedione-CH$_3$-CONHCHCOOH-phenyl | D(—)-, CH$_3$-piperazinedione-CH$_3$-CONHCHCONH-phenyl-cephem-CH$_2$S-(1-methyl-tetrazolyl); m.p. (decomp.) 173° C, yield 68 % |
| D(—)-, phenyl-piperazinedione-CONHCHCOOH-phenyl | D(—)-, phenyl-piperazinedione-CONHCHCONH-phenyl-cephem-CH$_2$S-(1-methyl-tetrazolyl); m.p. (decomp.) 163° C, yield 74.8 % |

\* Anhydrous methylene chloride was substituted for the methanol used in Example 29.

IR (nujol) cm⁻¹: $\nu_{C=O}$ 1780 (lactam), 1720 - 1650 (—CON<, —COOH)

The above-mentioned operation was repeated, except that the D(—)-α-(4-methyl-2,3-dioxo-1-piperazinocarbonylamino)phenylacetic acid was replaced by each of the compounds of formula (V) shown in Table 26, to obtain respective objective compounds as shown in Table 26. The structure of each objective compound was confirmed by IR and NMR.

EXAMPLE 33

The procedure of Example 29 was repeated, except that the D(—)-α-(4-methyl-2,3-dioxo-1-piperazinocarbonylamino)phenylacetic acid was replaced by each of the compounds of formula (V) shown in Table 27, to obtain respective objective compounds shown in Table 27. The structure of each objective compound was confirmed by IR and NMR.

Table 26

| Compound of formula (V) | Objective compound |
|---|---|
|  |  m.p. (decomp.) 147° C, yield 68.5 % |
|  | 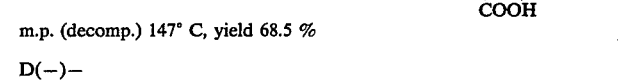 m.p. (decomp.) 158° C, yield 74.5 % |

Table 27

| Compound of formula (V) | Objective compound |
|---|---|
| 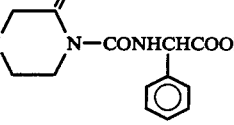 |  |
| 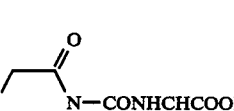 |  |
| 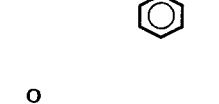 | 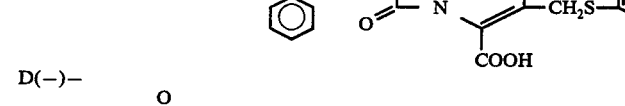 |
|  | 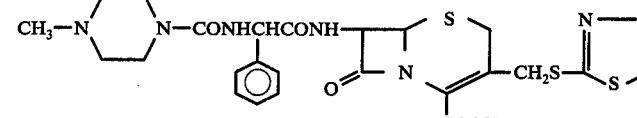 |

Table 27-continued

| Compound of formula (V) | Objective compound |
|---|---|
| D(−)− CH₃CONHCO−N(piperazin-3-one)N−CONHCHCOOH(phenyl) | D(−)− CH₃CONHCO−N(piperazin-3-one)N−CONHCHCONH−[β-lactam]−S−CH₂S−(thiadiazole)−CH₃, COOH, phenyl |
| D(−)− CH₃−N(piperazin-3-one)N−CONHCHCOOH(phenyl) | D(−)− CH₃−N(piperazin-3-one)N−CONHCHCONH−[β-lactam]−S−CH₂S−(thiadiazole)−CH₃, COOH, phenyl |
| D(−)− CH₃CH₂−N(piperazin-3-one)N−CONHCHCOOH(phenyl) | D(−)− CH₃CH₂−N(piperazin-3-one)N−CONHCHCONH−[β-lactam]−S−CH₂S−(thiadiazole)−CH₃, COOH, phenyl |
| D(−)− HN(2,5-dioxopiperazine)N−CONHCHCOOH(phenyl) | D(−)− HN(2,5-dioxopiperazine)N−CONHCHCONH−[β-lactam]−S−CH₂S−(thiadiazole)−CH₃, COOH, phenyl |
| D(−)− CH₃CO−N(2,5-dioxopiperazine)N−CONHCHCOOH(phenyl) | D(−)− CH₃CO−N(2,5-dioxopiperazine)N−CONHCHCONH−[β-lactam]−S−CH₂S−(thiadiazole)−CH₃, COOH, phenyl |

EXAMPLE 34

The procedure of Example 30 was repeated, except that the D(−)-α-(4-methyl-2,3-dioxo-1-piperazinocarbonylamino)phenylacetic acid was replaced by each of the compounds of formula (V) shown in Table 28, to obtain respective objective compounds shown in Table 28. The structure of each objective compound was confirmed by IR and NMR.

Table 28

| Compound of formula (V) | Objective compound |
|---|---|
| D(−)− CH₃CO−N(piperazin-3-one)N−CONHCHCOOH(phenyl) | D(−)− CH₃CO−N(piperazin-3-one)N−CONHCHCONH−[β-lactam]−S−CH₂S−(N-methyltetrazole), COOH, phenyl |
| D(−)− CH₃SO₂−N(piperazin-3-one)N−CONHCHCOOH(phenyl) | D(−)− CH₃SO₂−N(piperazin-3-one)N−CONHCHCONH−[β-lactam]−S−CH₂S−(N-methyltetrazole), COOH, phenyl |

Table 28-continued

| Compound of formula (V) | Objective compound |
|---|---|
| D(−)− structure with CH₃–N(piperazinone)–CONHCHCOOH–phenyl | D(−)− same acyl group coupled to cephem: –CONHCHCONH–[β-lactam]–CH₂S–(1-methyltetrazol-5-yl), COOH |
| D(−)− with CH₃CH₂–N(piperazinone)–CONHCHCOOH–phenyl | D(−)− corresponding cephem conjugate |
| D(−)− with CH₃CONHCO–N(piperazinone)–N–CONHCHCOOH–phenyl | D(−)− corresponding cephem conjugate |
| D(−)− with CH₃–N(3-oxopiperazine)–N–CONHCHCOOH–phenyl | D(−)− corresponding cephem conjugate |
| D(−)− with CH₃CH₂–N(3-oxopiperazine)–N–CONHCHCOOH–phenyl | D(−)− corresponding cephem conjugate |
| D(−)− with HN(2,5-dioxopiperazine)–N–CONHCHCOOH–phenyl | D(−)− corresponding cephem conjugate |
| D(−)− with CH₃CO–N(2,5-dioxopiperazine)–N–CONHCHCOOH–phenyl | D(−)− corresponding cephem conjugate |

EXAMPLE 35

(1) To a suspension of 0.9 g of D(−)-α-alanine in 15 ml of water was added 2.05 g of triethylamine to dissolve D(−)-α-alanine in water, and the resulting solution was cooled to 0° C. To the solution was added 2.3 g of 4-methyl-2,3-dioxo-1-piperazinocarbonyl chloride over 15 minutes, after which reaction was effected for 30 minutes with ice-cooling. Dilute hydrochloric acid was then added to the reaction product to adjust the pH thereof to 2.0. The water was removed by distillation under reduced pressure, and 30 ml of acetone was added to the residue, after which insolubles were filtered off. To the resulting acetone solution was added 10 ml of an acetone solution of 1.6 g of a sodium salt of 2-ethylhexanoic acid, and the deposited crystals were collected by filtration, and dried to obtain 2.1 g of a sodium salt of D(−)-α-(4-methyl-2,3-dioxo-1-piperazinocarbonylamino)propionic acid having a melting point of 115° − 8° C (decomp.), yield 78.5%.

IR (KBr) cm$^{-1}$: $\nu_{C=O}$ 1700, 1680, 1600 (—CON<, —COO$^\ominus$)

(2) In the same manner as in Example 32, 7-[D(—)-α-(4-methyl-2,3-dioxo-1-piperazinocarbonylamino)propionamido]-3-acetoxymethyl-Δ$^3$-cephem-4-carboxylic acid was obtained from a sodium salt of D(—)-α-(4-methyl-2,3-dioxo-1-piperazinocarbonylamino)propionic acid and 7-amino-3-acetoxymethyl-Δ$^3$-cephem-4-carboxylic acid. The thus obtained product was dissolved in 20 ml of acetone, and a solution of 0.65 g of a sodium salt of 2-ethylhexanoic acid in 5 ml of acetone was added to the resulting solution. The deposited crystals were collected by filtration and dried to obtain 1.2 g of sodium salt of 7-[D(—)-α-(4-methyl-2,3-dioxo-1-piperazinocarbonylamino)propionamido]-3-acetoxymethyl-Δ$^3$-cephem-4-carboxylic acid having a melting point of 195° C (decomp.), yield 67.7%.

IR (KBr) cm$^{-1}$: $\nu_{C=O}$ 1780 (lactam), 1710 - 1660 (—CON<), 1600 (—COO$^\ominus$)

EXAMPLE 36

In the same manner as in Example 32, 7-[D(—)-α-(4-methyl-2,3-dioxo-1-piperazinocarbonylamino)-p-hydroxyphenylacetamido]-3-[5-(1-methyl-1,2,3,4-tetrazolyl)-thiomethyl]-Δ$^3$-cephem-4-carboxylic acid was obtained from 7-amino-3-[5-(1-methyl-1,2,3,4-tetrazolyl)-thiomethyl]-Δ$^3$-cephem-4-carboxylic acid and D(—)-α-(4-methyl-2,3-dioxo-1-piperazinocarbonylamino)-p-hydroxyphenylacetic acid.

Melting point (decomp.), 147° - 9° C; yield, 62.0%

IR (KBr) cm$^{-1}$: $\nu_{C=O}$ 1765 (lactam), 1720 - 1660 (—CON<, —COOH)

EXAMPLE 37

In the same manner as in Example 29, 7-[D(—)-α-(4-methyl-2,3-dioxo-1-piperazinocarbonylamino)-phenylacetamido]-3-azidomethyl-Δ$^3$-cephem-4-carboxylic acid was obtained from D(—)-α-(4-methyl-2,3-dioxo-1-piperazinocarbonylamino)phenylacetic acid and 7-amino-3-azidomethyl-Δ$^3$-cephem-4-carboxylic acid.

Melting point (decomp.), 185°- 8° C; yield, 68.0%

IR (KBr) cm$^{-1}$: $\nu_{C=O}$ 1775 (lactam), 1720 - 1660; (—CON<, —COOH) $\nu_{N_3}$ 2090

EXAMPLE 38

In 10 ml of a phosphoric acid buffer solution of a pH of 6.3 was suspended 0.57 g of 7-[D(—)-α-(4-ethyl-2,3-dioxo-1-piperazinocarbonylamino)phenylacetamido]-3-acetoxymethyl-Δ$^3$-cephem-4-carboxylic acid, and 0.07 g of sodium hydrogencarbonate was dissolved therein. To the solution was then added 0.12 g of 1-methyl-5-mercapto-1,2,3,4-tetrazole to dissolve the latter in the former, and the solution was subjected to reaction for 24 hours while maintaining the pH of the solution at 6.5 - 6.7 by using dilute hydrochloric acid and sodium hydrogencarbonate. After the reaction, the reaction liquid was cooled, and then adjusted to a pH of 5.0 by adding dilute hydrochloric acid. The reaction liquid was sufficiently washed with ethyl acetate, after which the aqueous layer was separated off and then adjusted to a pH of 1.5 by adding dilute hydrochloric acid thereto. The deposited crystals were collected by filtration and dried, after which the dried crystals were washed with ethyl acetate to obtain 0.40 g of 7-[D(—)-α-(4-ethyl-2,3-dioxo-1-piperazinocarbonylamino)phenylacetamido]-3-[5-(1-methyl-1,2,3,4-tetrazolyl)thiomethyl]-Δ$^3$-cephem-4-carboxylic acid, m.p. 163°- 165° C (decomp.), yield 74.5%.

IR (KBr) cm$^{-1}$: $\nu_{C=O}$ 1775 (lactam), 1720 - 1660 (—CON<, —COOH)

NMR (d$_6$-DMSO) τ values: 0.18 (1H, d), 0.55 (1H, d), 2.64 (5H, s), 4.3 (1H, q), 4.4 (1H, d), 5.0 (1H, d), 5.75 (2H, s), 6.05 (5H, s), 6.3 - 6.8 (6H), 8.92 (3H, t)

In the same manner as above, the objective compounds shown in Table 29 were obtained from 7-[D(—)-α-(4-methyl-2,3-dioxo-1-piperazinocarbonyl)-phenylacetamido]-3-acetoxymethyl-Δ$^3$-cephem-4-carboxylic acid or 7-[D(—)-α-(4-ethyl-2,3-dioxo-1-piperazioncarbonylamino)phenylacetamido]-3-acetoxymethyl-Δ$^3$-cephem-4-carboxylic acid and the compounds of formula (VII) shown in Table 29. All the objective compounds were D(—) isomers, and the structure of each objective compound was confirmed by IR and NMR.

Table 29

| Compound of formula (VII) | Objective compound |
|---|---|
| N—N, N with SH, CH₃ (1-methyl-tetrazole-5-thiol) | CH₃—N(piperazinedione)N—CONHCHCONH—(phenyl)—cephem—CH₂S—tetrazole-N-CH₃ <br> m.p. (decomp.) 168 - 170° C, yield 83 % |
| N—N, CH₃—S—SH (5-methyl-1,3,4-thiadiazole-2-thiol) | CH₃CH₂—N(piperazinedione)N—CONHCHCONH—(phenyl)—cephem—CH₂S—thiadiazole—CH₃ <br> m.p. (decomp.) 150° C, yield 73.4 % |
| N—N, S—SH (1,3,4-thiadiazole-2-thiol) | CH₃—N(piperazinedione)N—CONHCHCONH—(phenyl)—cephem—CH₂S—thiadiazole <br> m.p. (decomp.) 158 - 159° C, yield 78.5 % |

Table 29-continued

| Compound of formula (VII) | Objective compound |
|---|---|
| 3-mercapto-1,2,4-triazole (N—N / NH / SH) | Structure with CH₃—piperazinedione—CONHCHCONH—(phenyl)—β-lactam—S—CH₂—triazole; m.p. (decomp.) 175 – 180° C, yield 73.4 % |
| 5-mercaptotetrazole (NH) | Structure with CH₃—piperazinedione—CONHCHCONH—(phenyl)—β-lactam—S—CH₂—tetrazole (NH); m.p. (decomp.) 163 – 165° C, yield 72.5 % |
| 5-mercaptotetrazole (NH) | Structure with CH₃CH₂—piperazinedione—CONHCHCONH—(phenyl)—β-lactam—S—CH₂—tetrazole (NH); m.p. (decomp.) 159 – 160° C, yield 66 % |
| 2-mercapto-5-methyl-1,3,4-oxadiazole | Structure with CH₃—piperazinedione—CONHCHCONH—(phenyl)—β-lactam—S—CH₂—oxadiazole—CH₃; m.p. (decomp.) 128 – 129° C, yield 67.7 % |
| 3-mercapto-2,5-dimethyl-6-oxo-1,2,4-triazine | Structure with CH₃—piperazinedione—CONHCHCONH—(phenyl)—β-lactam—S—CH₂—triazinone(CH₃, N—CH₃); m.p. (decomp.) 95 – 98° C, yield 66.6 % |
| 2-mercapto-4-methyl-1,3-oxazole | Structure with CH₃CH₂—piperazinedione—CONHCHCONH—(phenyl)—β-lactam—S—CH₂—oxazole-CH₃; m.p. (decomp.) 175 – 180° C, yield 78.0 % |
| 2-mercapto-4-methyl-1,3-thiazole | Structure with CH₃—piperazinedione—CONHCHCONH—(phenyl)—β-lactam—S—CH₂—thiazole-CH₃; m.p. (decomp.) 156 – 157° C, yield 67.0 % |
| 2-mercaptopiperidine-N-oxide | Structure with CH₃CH₂—piperazinedione—CONHCHCONH—(phenyl)—β-lactam—S—CH₂—piperidine-N-oxide |

Table 29-continued

| Compound of formula (VII) | Objective compound |
|---|---|
| [2-mercapto-4,5-dihydro-1,3-thiazole] | m.p. (decomp.) 177 – 180° C, yield 70.3 %<br>[cephem product with CH$_2$S-(4,5-dihydrothiazol-2-yl) substituent, 7-[D-α-(4-methyl-2,3-dioxo-1-piperazinocarbonylamino)phenylacetamido]] |
| [1-methyl-2-mercaptoimidazole] | m.p. (decomp.) 180 – 182° C, yield 68.7 %<br>[cephem product with CH$_2$S-(1-methylimidazol-2-yl) substituent] |
| [2-mercapto-1,3-diazacyclohexene] | m.p. (decomp.) 182 – 184° C, yield 68 %<br>[cephem product with corresponding CH$_2$S-heterocycle substituent] |
| [3-methyl-6-mercapto-tetrahydropyridazine] | m.p. (decomp.) 192 – 194° C, yield 72.3 %<br>[cephem product, 7-[D-α-(4-ethyl-2,3-dioxo-1-piperazinocarbonylamino)phenylacetamido], with CH$_2$S-(6-methyltetrahydropyridazin-3-yl) substituent] |
| NaN$_3$ | m.p. (decomp.) 175 – 178° C, yield 63.0 %<br>[cephem product with CH$_2$N$_3$ substituent] |
| CH$_3$—N[piperazine]N—C(=S)—SNa | m.p. (decomp.) 185 – 188° C, yield 78 %<br>[cephem product with CH$_2$SC(=S)—N(piperazine)N—CH$_3$ substituent] |
| [4-methylisoxazole-5-C(=O)—SNa] | m.p. (decomp.) 189° C, yield 64.6 %<br>[cephem product with CH$_2$SC(=O)-(4-methylisoxazol-5-yl) substituent] |
| CH$_3$CH$_2$OC(=S)—SNa | m.p. (decomp.) 183° C, yield 69.1 %<br>[cephem product with CH$_2$SC(=S)OCH$_2$CH$_3$ substituent] |
| | m.p. (decomp.) 181 – 183° C, yield 64.3 % |

EXAMPLE 39

In 10 ml of water was suspended 1.15 g of 7-[D(—)-α-(4-ethyl-2,3-dioxo-1-piperazinocarbonylamino)-phenylacetamido]-3-acetoxymethyl-Δ$^3$-cephem-4-carboxylic acid, and 0.17 g of sodium hydrogencarbonate was then dissolved therein, after which 0.48 g of pyridine and 4.1 g of potassium thiocyanate were added thereto. The resulting mixture was subjected to reaction at 60° C for 5 hours while maintaining the pH of the mixture at 6.0 to 6.5 by adding dilute hydrochloric acid or sodium hydrogencarbonate. After the reaction, 20 ml of water was added to dilute the reaction mixture, which was then sufficiently washed with chloroform. The aqueous layer was then separated off and then adjusted to a pH of 1.5 by adding dilute hydrochloric acid. The deposited crystals were collected by filtration, dried, and then washed with acetone to obtain 1.04 g (yield, 79.6%) of a thiocyanic acid salt of 7-[D(—)-α-(4-ethyl-2,3-dioxo-1-piperazinocarbonylamino)-phenylacetamido]-3-pyridinomethyl-Δ³-cephem-4-carboxylic acid betaine having a melting point (decomp.) of 155°- 160° C, said product having the formula

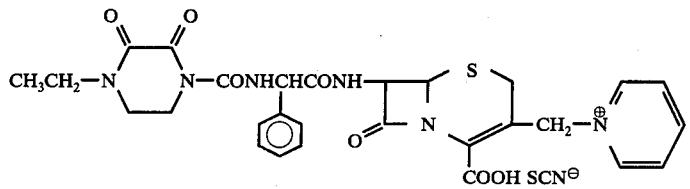

IR (KBr) cm⁻¹: ν<sub>C=O</sub> 1780 (lactam), 1720 — 1660 (—CON<) ν<sub>SCN</sub> 2040

In the same manner as above, a thiocyanic acid salt of 7-[D(—)-α-(4-methyl-2,3-dioxo-1-piperazinocarbonylamino)phenylacetamido]-3-pyridinomethyl-Δ³-cephem-4-carboxylic acid betaine was obtained from 7-[D(—)-(4-methyl-2,3-dioxo-1-piperazinocarbonylamino)phenylacetamido]-3-acetoxymethyl-Δ³-cephem-4-carboxylic acid and pyridine, said product having the formula,

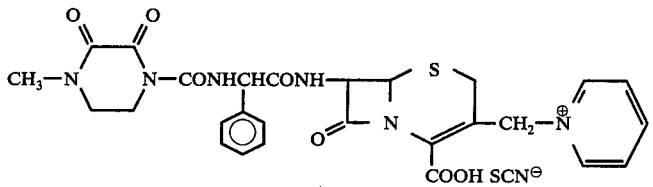

Melting point (decomp.), 180°- 185° C; yield, 82.0%

In a conventional manner, the above two products were treated with an ion exchange resin to obtain the desired 7-[D(—)-α-(4-ethyl-2,3-dioxo-1-piperazinocarbonylamino)phenylacetamido]- 3-pyridinomethyl-Δ³-cephem-4-carboxylic acid betaine and 7-[D(—)-α-(4-methyl-2,3-dioxo-1-piperazinocarbonylamino)-phenylacetamido]-3-pyridinomethyl-Δ³-cephem-4-carboxylic acid betaine.

EXAMPLE 40

In 85 ml of anhydrous methanol as dissolved 1.5 g of a sodium salt of 7-[D(—)-α-(4-ethyl-2,3-dioxo1-piperazinocarbonylamino)phenylacetamido]-3-[2-(pyridyl1-oxide)thiomethyl]-Δ³-cephem-4-carboxylic acid. To the resulting solution was added 0.65 g of anhydrous cupric chloride, and the resulting mixture was stirred at room temperature for 15 minutes and then subjected to reaction at 50° C for 14 hours. After the reaction, hydrogen sulfide gas was passed through the reaction solution with ice-cooling for 20 minutes. The resulting insolubles were filtered off, and the filtrate was concentrated under reduced pressure. To the residue was added 20 ml of a 5% aqueous sodium hydrogencarbonate solution, and the insolubles were filtered off, after which dilute hydrochloric acid was added to the filtrate to adjust the pH to 6.5. The filtrate was then washed with 10-ml portions of ethyl acetate three times, after which the aqueous layer was separated off and then adjusted to a pH of 1.8 by adding dilute hydrochloric acid thereto. The thus deposited crystals were collected by filtration and then dried under reduced pressure and washed with 20 ml of an ethyl acetate-chloroform mixed solvent (1:1 by volume) to obtain 0.40 g of 7-[D(—)-α-(4-ethyl-2,3-dioxo1-piperazinocarbonylamino)phenylacetamido]-3-methoxymethyl-Δ³-cephem-4-carboxylic acid, m.p. 162°- 6° C (decomp.), yield 30.5%.

IR (KBr) cm⁻¹: ν<sub>C=O</sub> 1770 (lactam), 1700 (—COOH), 1666 (—CON<)

NMR (d<sub>6</sub>-DMSO) τ values: 0.13 (1H, d), 0.53 (1H, d), 2.61 (5H, s), 4.31 (1H, q), 4.41 (1H, d), 4.96 (1H, d), 5.82 (2H, s), 6.10 (2H, bs), 6.33 (2H, 2H, 2H, bs), 6.79 (3H, s), 8.89 (3H, t)

What is claimed is:

1. A compound of the formula,

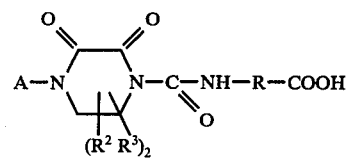

wherein

A is a hydrogen atom or a C<sub>1-12</sub> alkyl, C<sub>2-4</sub> alkenyl, phenyl, naphthyl, benzyl or phenethyl group alone or substituted by halogen, hydroxyl, nitro, cyano, pyrrolidino, piperidino, morpholino and acetoxy;

R² and R³ are linked to the same carbon atom, and R² and R³ individually are hydrogen, methyl, ethyl, propyl, butyl, pentyl, hexyl, heptyl, or octyl, and R is

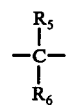

wherein

R<sub>5</sub> is C<sub>1-8</sub> alkyl, C<sub>5-7</sub> cycloalkyl, C<sub>5-6</sub> cycloalkenyl, C<sub>5-6</sub> cycloalkadienyl, phenyl, naphthyl, benzyl, phenethyl, phenoxy, naphthoxy, C<sub>1-2</sub> alkylthio- C<sub>1-2</sub> alkyl, furyl, thienyl, oxazolyl, thiazolyl, isoxazolyl, isothiazolyl, imidazolyl, pyrazolyl, pyridyl, pyrazyl, pyrimidinyl, pyridazinyl, quinolyl, isoquinolyl, quinazolinyl, indolyl, indazolyl, 1,3,4-oxadiazolyl, 1,2,4-oxadiazolyl, 1,3,4-thiadiazolyl or 1,2,4-thiadiazolyl alone or substituted by halogen, hydroxy and nitro; $R_6$ is hydrogen and $R_5$ and $R_6$ together with the common carbon atom to which they are attached may form a $C_{6-7}$ cycloalkyl, $C_{5-6}$ cycloalkenyl or $C_{5-6}$ cycloalkadienyl ring;

a salt thereof selected from the group consisting of alkali metal salts, alkaline earth metal salts, ammonium salts, and salts with trimethylamine or dicyclohexylamine, or a reactive derivative of the carboxyl group thereof, said derivative being conventional in the field of pencillins and cephalosporins for forming acid amides therewith, and said derivative being selected from the group consisting of acid halides, acid anhydrides, mixed acid anhydrides with organic or inorganic acids, active acid amides, acid cyanides and active esters.

2. The compound of claim 1, wherein R is

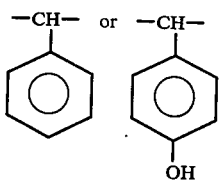

3. The compound of claim 1, wherein A is a $C_{1-12}$ alkyl group and R is

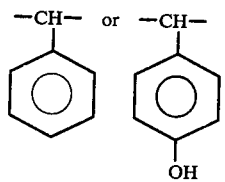

4. The compound of claim 1, wherein A is a methyl or ethyl group and R is

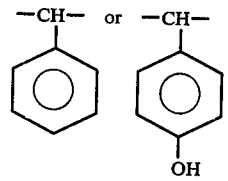

5. The compound of claim 4 which is D(−)-α-(4-ethyl-2,3-dioxo-1-piperazinocarbonylamino)phenylacetic acid or its sodium salt.

6. The compound of claim 4 which is D(−)-α-(4-ethyl-2,3-dioxo-1-piperazinocarbonylamino)-p-hydroxyphenylacetic acid or its sodium salt.

7. The compound of claim 4 which is a mixed acid anhydride of D(−)-α-(4-ethyl-2,3-dioxo-1-piperazinocarbonylamino)phenylacetic acid with ethylchlorocarbonate or is an acid halide of said acid.

8. The compound of claim 4 which is a mixed acid anhydride of D(−)-α-(4-ethyl-2,3-dioxo-1-piperazinocarbonylamino)-p-hydroxyphenylacetic acid with ethyl chlorocarbonate or is an acid halide of said acid.

* * * * *

UNITED STATES PATENT AND TRADEMARK OFFICE
CERTIFICATE OF CORRECTION

PATENT NO. : 4,110,327

DATED : August 29, 1978

INVENTOR(S) : ISAMU SAIKAWA ET AL

It is certified that error appears in the above-identified patent and that said Letters Patent are hereby corrected as shown below:

Front page, left column, last line, delete "50-37027" and insert --50-37207--.

Column 2, lines 13-19, correct the structural formula to read as follows --
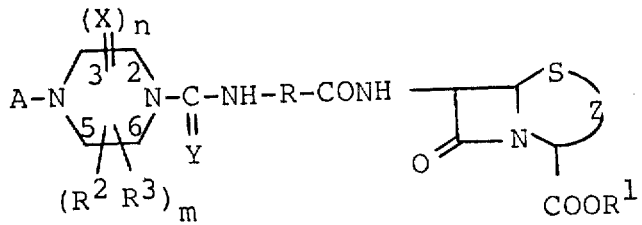
--

Column 2, line 30, delete "carbonyl" and insert --carboxyl--

Column 2, line 64, after "aromatic" insert --,-- (comma)

Column 3, line 11, delete "clopentyl" and insert --clopentenyl--

Column 3, line 14, delete "phenetyl" and insert --phenethyl--

Column 3, line 43, delete "(tert-butyl)" and insert --(tert.-butyl)--

Column 3, line 67, delete "saltforming" and insert --salt-forming--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 4, line 7, delete "N-benzylβ-" and insert --N-benzyl-β- --

Column 6, line 11, delete "n,N-" (both instances and insert --N,N- -- (both instances)

Column 7, lines 23 to 59, structural formulas (Ia), (Ib), (Ic), (Id) and (Ie); Column 8, lines 1 to 8, structural formula; and Column 8, lines 31 to 37, structural formula, delete " 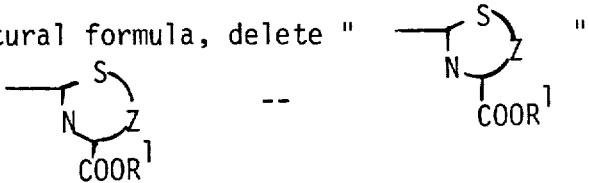 "

(i.e., the bond between the N atom and the adjacent carbon atom in the ring containing N, S and Z should not be a curve but a straight line in each of the structural formulas).

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 9, line 27, after "groups" (first instance) insert --,-- (comma)

Column 10, line 4, after "active" (second instance) insert --acid--

Column 10, line 28, delete "An." and insert --Am.--

Columns 9-10, 11-12, 13-14, 15-16, 17-18, 19-20, 21-22 and 23-24, Table 1 in each instance, delete structural formula (VIII) and insert in each instance -- 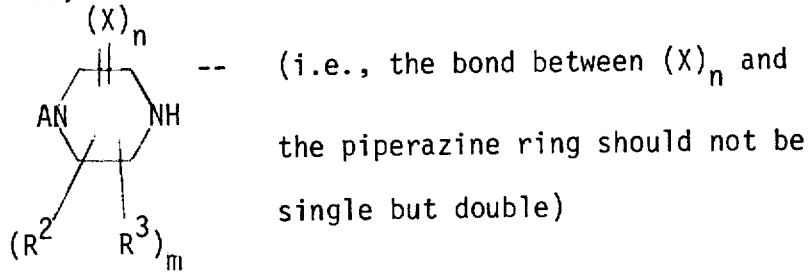 -- (i.e., the bond between $(X)_n$ and the piperazine ring should not be single but double)

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Columns 21-22, the structural formula of the fourth compound from the bottom should be deleted and insert therefore -- 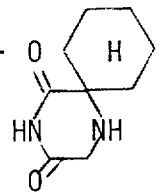 --

Columns 21-22, first, second and third structural formulas from the bottom, delete " ⟩NH " (in each instance) and insert -- ⟩NH -- (in each instance)

Columns 23-24, (Table 1), the structural formulas of the two compounds, delete " ⟩NH " (in each instance) and insert -- ⟩NH -- (in each instance)

UNITED STATES PATENT AND TRADEMARK OFFICE
CERTIFICATE OF CORRECTION

PATENT NO. : 4,110,327          Page 5 of 22

DATED : August 29, 1978

INVENTOR(S) : ISAMU SAIKAWA ET AL

It is certified that error appears in the above-identified patent and that said Letters Patent are hereby corrected as shown below:

Column 40, line 57, delete "2,5dioxo" and insert --2,5-dioxo--

Column 41, line 64, delete "carbonyl" and insert --carboxyl--

Column 42, line 12, delete "N,N-dicyclohexyl" and insert --N,N'-dicyclohexyl"

Column 42, line 49, delete "N.N'-carbonyl" and insert --N,N'-carbonyl bis--

Column 43, line 28, delete "tartarate" and insert --tartrate--

Column 43, line 57, delete "(19, (2) and )3)" and insert --(1), (2) and (3)--

Column 43, line 64, delete "4-enanthoy" and insert --4-enanthoyl--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 44, line 7, delete "hepxyl" and insert --hexyl--

Column 44, line 21, delete "capryloxy" and insert --caryloyl--

Column 44, line 49, delete "phenyolacetamido" and insert --phenylacetamido--

Column 46, line 43, delete "piperazinoar-" and insert --piperazinocar- --

Column 46, line 64, delete "piperazinocarbonlamino" and insert --piperazinocarbonylamino--

Column 47, line 1, delete "trichlorethoxycarbonyl" and insert --trichloroethyoxycarbonyl--

Column 47, line 2, delete "tamethyllene" and insert --tamethylene--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 47, lines 5, 43, 46 and 50, delete "1piperazinocarbonylamino" and insert --1-piperazinocarbonylamino-- (in each instance)

Column 47, line 19, delete "N" and insert --n--

Column 47, line 35, delete "ocytl" and insert --octyl--

Column 47, line 41, after "dioxo-1" insert -- -piperazinocarbonylamino)phenylacetamido]penicillanate,--

Column 47, line 56, delete "1piperazinocarbonylamino" and insert --1-piperazinocarbonylamino--

Column 47, line 56, delete "pen-" and insert --peni- --

Column 48, line 14, delete "phenylacetaido" and insert --phenylacetamido--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 48, line 24, delete "4carboxylic" and insert --4-carboxylic--

Column 48, line 34, delete "methyl:" and insert --methyl- --

Column 48, line 40, delete "thiadiaolyl" and insert --thiadiazolyl)thiomethyl--

Column 48, line 43, delete "triomethyl" and insert --thiomethyl--

Column 48, line 45, delete "ipierazinocar-" and insert --piperazinocar- --

Column 48, line 49, delete "60" and insert --α--

Column 48, line 54, delete in its entirety and insert --bonylamino)phenylacetamido]-3-[5-(1-methyl-1,2,3,4-tetrazolyl)-thiomethyl]-$\Delta^3$-cephem-4-carboxylic acid--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 48, line 57, delete "1m" and insert --1--

Column 48, line 64, delete "-3-[5-[5-(1-" and insert -- -3-[5-(1- --

Column 49, line 9, after "thiomethyl]" insert -- - -- (hyphen)

Column 49, line 11, delete "22" and insert --2--

Column 49, line 37, delete "4methyl" and insert --4-methyl--

Column 49, line 39, delete "triomethyl" and insert --thiomethyl--

Column 49, line 13, delete "thiomeethyl" and insert --thiomethyl--

Column 49, line 50, delete "6" and insert --Δ--

Column 49, line 54, after "dihydro" insert -- - -- (hyphen)

Column 49, line 54, after "triazinyl" insert --)--

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 49, line 68, after "omethyl" insert -- - -- (hyphen)

Column 50, line 1, delete "31" and insert -- - -- (hyphen)

Column 50, line 2, delete "phenyoacetamido]-3-[2-(1me-" and insert --phenylacetamido]-3-[2-(1-me- --

Column 50, line 5, delete "piperzinocar-" and insert --piperazinocar- --

Column 50, line 16, delete "4" (first occurrence) and insert --7--

Column 50, line 16, after "2,3" insert -- - -- (hyphen)

Column 50, line 21, delete "phenkacetamido" and insert --phenylacetamido--

Column 50, line 22, after "bonylthiomethyl" insert -- - -- (hyphen)

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 50, line 23, delete "1piperazinocar-" and insert --1-piperazinocar- --

Column 50, line 35, after "phenylacetamido]-" insert --3-[2-(5-methyl-1,3,4-thiadiazolyl)thiomethyl]- --

Column 50, line 54, delete "1" and insert --2--

Column 51, line 16, after "tetrazolyl" insert --)--

Column 51, line 19, delete "bonylamono)" and insert --bonylamino)--

Column 77, Table 3, delete " 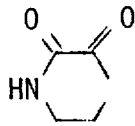 " of the structural formula of Compound No. 59 and insert -- 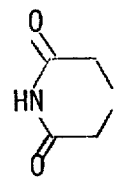 --

UNITED STATES PATENT AND TRADEMARK OFFICE
CERTIFICATE OF CORRECTION

PATENT NO. : 4,110,327                                Page 12 of 22

DATED : August 29, 1978

INVENTOR(S) : ISAMU SAIKAWA ET AL

It is certified that error appears in the above-identified patent and that said Letters Patent are hereby corrected as shown below:

Columns 79 and 80, Table 4, under the heading 'Klebsiella pneumoniae' delete "100", "100", "200" and "200" and insert in each instance --<1.57--, --<1.57--, --1.57-- and --3.13-- respectively.

Columns 79 and 80, Table 4, under the heading 'Proteus vulgaris 3027', delete "<1.57", "<1.57", "1.57" and "3.13" and insert in each instance --100--, --100--, --200-- and --200--, respectively.

Columns 81 to 82, Table 4, delete "  " of the structural formula of Compound 64 and insert --  --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Columns 87 to 88, Table 5-3, under the heading 'GN 383', delete the second value "30" and insert --50--

Columns 87 to 88, Table 5-3, under the heading 'GN 383', delete the last value "25" and insert --50--

Columns 89 to 90, Table 6-1; Columns 91 to 92, Tables 6-2, 6-3 and 6-4, under the heading 'Compound' in each table, delete "Cephalorizine" and insert --Cephaloridine-- in each instance

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 93, line 33, delete "pneumonia" and insert --pneumoniae--

Column 93, line 54, delete "19 ± g)" and insert -- 19 ± 1 g)--

Column 94, line 59, delete "NRM" and insert --NMR--

Column 94, line 59, delete "π" and insert -- τ --

Column 98, line 55, delete "colled" and insert --cooled--

Columns 101 to 102, Table 9, under the heading 'Objective compound' delete "  " in the second, third, fourth, fifth and sixth structural formulae, and insert --  -- in each instance Columns 103 and 104, Table 9, under the heading 'Objective compound' i delete " 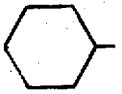 " in the second structural formula and insert --  --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 103, lines 36 and 44, delete "oxopiperazine" and insert --oxo-piperazine-- (in each instance)

Column 104, line 64, delete "π" and insert -- τ --

Columns 107 to 108, Table 10, third structural formula and columns 115 to 116, Table 11, second structural formula, under the heading 'Objective compound' delete "  " in each instance and insert -- 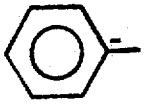 -- in each instance Column 115, line 47, after "(—COO$^\ominus$" insert --,-- (comma)

Columns 117 to 118, under the heading 'Reactive derivative of compound of formula (III)', Table 12, above the fourth formula, delete "D(-)-"

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Columns 117 to 118, Table 12, under the heading 'Reactive derivative of compound of formula (III)', above the fourth structural formula, delete "D(-)-"

Columns 117 to 118, Table 12, under the heading 'Objective compound', above the fourth structural formula, insert --D(-)- --

Columns 119 to 120, Table 12, under the heading 'Reactive derivative of compound of formula (III)', above the first, third and fourth structural formulae, delete "D(-)-" in each instance Columns 119 to 120, Table 12, under the heading 'Objective compound, above the first, third and fourth structural formulae, insert --D(-)- -- in each instance

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 121, line 52, delete "dioxopiperazine" and insert --dioxo-piperazine--

Column 122, line 16, after "8.0" insert --to 8.5--

Column 122, line 14, delete "30" and insert --50--

Column 122, line 19, delete "uan" and insert --uran--

Column 122, line 47, delete "NMR(" and insert --NMR((--

Column 131, line 33, delete in its entirety

Column 131, line 56, delete "methyl" and insert --methyl- --

Column 131, after line 68, insert -- ride was replaced by 4=n-octyl-2,3-dioxo-1- --

Column 132, line 56, delete "dioxol-" and insert --dioxo-1- --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL Page 18 of 22

It is certified that error appears in the above-identified patent and that said Letters Patent are hereby corrected as shown below:

Column 134, line 55, delete "thic" and insert --this--

Column 135, line 66, before "—COOH," insert --(--

Column 137, line 1, delete "Nmethyl-" and insert --N-methyl- --

Column 137, line 8, delete "6aminopenicillanic" and insert --6-aminopenicillanic--

Column 139, line 14, delete "g" and insert --q--

Column 141, line 52, delete "em4-" and insert -- em-4- --

Column 141, line 53, delete "ph" and insert --pH--

Column 142, line 47, delete "7[D(-)-" and insert -- 7-[D(-)- --

Column 143, line 55, delete "4methyl" and insert --4-methyl--

Column 143, line 63, delete "αamino-" and insert --α-amino- --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Column 144, line 61, delete "as" and insert --was--

Column 145, line 2, delete "g" and insert --q--

Column 147, line 9, delete "-20°C" and insert --20°C--

Columns 147 to 148, Table 24, under the heading 'Compound of formula (V)', the fourth structural formula, delete "  " and insert -- 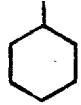 --

Column 158, line 35, delete "piperazinocarbonyl)" and insert --piperazinocarbonylamino)- --

Columns 159 to 160, Table 29, under the heading 'Compound of formula (VII)', delete the eighth structural formula and insert -- 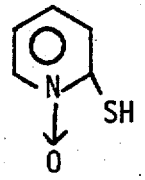 --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above–identified patent and that said Letters Patent are hereby corrected as shown below:

Columns 159 to 160, Table 29, under the heading 'Objective compound', eighth structural formula, delete " 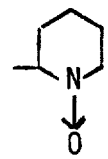 "

and insert -- 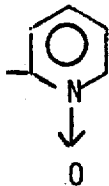 --

Columns 161 to 162, Table 29, under the heading 'Objective compound', first structural formula, delete " 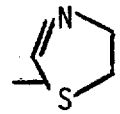 "

and insert -- 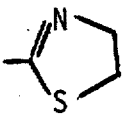 --

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA ET AL It is certified that error appears in the above-identified patent and that said Letters Patent are hereby corrected as shown below:

Columns 161 to 162, Table 29, under the heading 'Compound of formula (VII), delete the third structural formula and insert -- 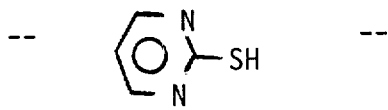 --

Columns 161 to 162, Table 29, under the heading 'Objective compound', third structural formula, delete " 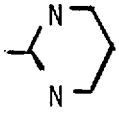 " and insert -- 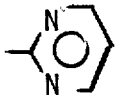 --

Columns 161 to 162, Table 29, under the heading 'Compound of formula (VII), delete the fourth structural formula and insert -- 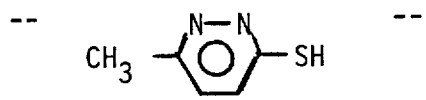 --

UNITED STATES PATENT AND TRADEMARK OFFICE
CERTIFICATE OF CORRECTION

PATENT NO. : 4,110,327

DATED : August 29, 1978

INVENTOR(S) : ISAMU SAIKAWA ET AL

It is certified that error appears in the above-identified patent and that said Letters Patent are hereby corrected as shown below:

Columns 161 to 162, Table 29, under the heading 'Objective compound', fourth structural formula, delete " 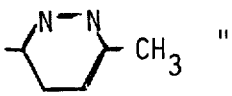 "

and insert -- 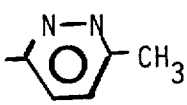 --

Column 163, line 54, delete "as" and insert --was--

Column 163, line 55, delete "dioxol-" and insert --dioxo-1- --

Column 163, line 57, delete "(pyridyl1" and insert --(pyridyl-1 --

Column 165, lines 26 to 34 and Column 166, lines 1 to 9 and 12 to 19, delete the structural formula in each instance and insert -- 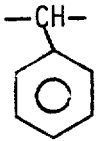 or 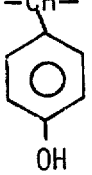 -- in each instance Signed and Sealed this Twenty-second Day of July 1980

[SEAL]

Attest:

SIDNEY A. DIAMOND

Attesting Officer    Commissioner of Patents and Trademarks

UNITED STATES PATENT AND TRADEMARK OFFICE
CERTIFICATE OF CORRECTION

PATENT NO. : 4,110,327
DATED : August 29, 1978
INVENTOR(S) : ISAMU SAIKAWA et al It is certified that error appears in the above—identified patent and that said Letters Patent is hereby corrected as shown below:

Columns 81 to 82, Table 4, delete " " of the structural formula of Compound 65 and insert -- --.

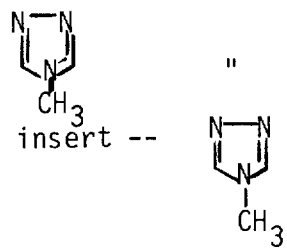

Signed and Sealed this

Thirteenth Day of January 1981

[SEAL]

Attest:

SIDNEY A. DIAMOND

Attesting Officer      Commissioner of Patents and Trademarks